US012508145B2

(12) United States Patent
Zimmer et al.

(10) Patent No.: US 12,508,145 B2
(45) Date of Patent: Dec. 30, 2025

(54) ORTHOPEDIC BRACE AND DONNING METHOD

(71) Applicant: Aspen Medical Products, LLC, Irvine, CA (US)

(72) Inventors: Erik Zimmer, Oceanside, CA (US); Jane Price, Anaheim, CA (US)

(73) Assignee: Aspen Medical Products, LLC, Irvine, CA (US)

( * ) Notice: Subject to any disclaimer, the term of this patent is extended or adjusted under 35 U.S.C. 154(b) by 280 days.

(21) Appl. No.: 18/162,383

(22) Filed: Jan. 31, 2023

(65) Prior Publication Data

US 2023/0240879 A1 Aug. 3, 2023

Related U.S. Application Data

(60) Provisional application No. 63/305,678, filed on Feb. 1, 2022.

(51) Int. Cl.
*A61F 5/02* (2006.01)

(52) U.S. Cl.
CPC .............. *A61F 5/028* (2013.01); *A61F 5/024* (2013.01)

(58) Field of Classification Search
CPC ........ A61F 5/022; A61F 5/028; A61F 5/0193; A61F 5/024; A61F 5/026; A61F 5/02–03; A61F 5/055; A41D 13/0506–0537; A41C 1/00; A41C 1/08; A41C 1/10; A41C 1/12; A41C 1/14
USPC ............... 602/12, 5, 19; 128/96.1, 99.1, 846
See application file for complete search history.

(56) References Cited

U.S. PATENT DOCUMENTS 2,973,030 A 2/1961 Matthewson
5,964,722 A 10/1999 Goralnik et al.
6,500,137 B1 * 12/2002 Molino .................. A61F 5/022 602/19
6,676,620 B2 * 1/2004 Schwenn ................ A61F 5/028 602/19

(Continued)

FOREIGN PATENT DOCUMENTS

FR 2992168 A1 12/2013

OTHER PUBLICATIONS

PCT/US2023/012137 filed Feb. 1, 2023 International Search Report and Written Opinion dated May 9, 2023.

(Continued)

*Primary Examiner* — Rachael E Bredefeld
*Assistant Examiner* — Seth R. Brown
(74) *Attorney, Agent, or Firm* — Rutan & Tucker, LLP

(57) ABSTRACT

An orthopedic brace features a posterior bracing system coupled to an anterior bracing system. The posterior bracing system includes a first plurality of telescopic lateral panels with a first telescopic lateral panel coupled to a first belt member and a second telescopic lateral panel coupled to a second belt member. The anterior bracing system includes a second plurality of telescopic lateral panels such as a third telescopic lateral panel and a fourth telescopic lateral panel. The first telescopic lateral panel and the first belt member are positioned into a curved form to enable the first belt member to attach to the third telescopic lateral panel of the anterior bracing system while the second telescopic lateral panel and the second belt member are positioned into a curved form to enable the second belt member to attach to the fourth telescopic lateral panel of the anterior bracing system.

19 Claims, 53 Drawing Sheets

(56) References Cited

U.S. PATENT DOCUMENTS

| | | | | |
|---|---|---|---|---|
| 7,001,348 | B2 * | 2/2006 | Garth | A61F 5/02 602/5 |
| 7,608,052 | B1 | 10/2009 | Baker | |
| 8,172,779 | B2 | 5/2012 | Ingimundarson et al. | |
| 8,216,167 | B2 | 7/2012 | Garth et al. | |
| 8,556,840 | B2 | 10/2013 | Burke et al. | |
| 8,795,214 | B1 * | 8/2014 | Conti | A61F 5/02 602/5 |
| 9,220,625 | B2 | 12/2015 | Ingimundarson et al. | |
| 9,504,596 | B1 * | 11/2016 | Kozersky | A61F 5/028 |
| 10,070,985 | B2 | 9/2018 | Glazener et al. | |
| 10,231,862 | B2 | 3/2019 | Summit et al. | |
| 10,238,524 | B2 | 3/2019 | Burke et al. | |
| 11,273,065 | B2 * | 3/2022 | Garth | A61F 5/34 |
| 2002/0198481 | A1 | 12/2002 | Humphries | |
| 2003/0208147 | A1 * | 11/2003 | Reinecke | A61F 5/024 602/19 |
| 2004/0077981 | A1 | 4/2004 | Weaver et al. | |
| 2004/0220503 | A1 | 11/2004 | Kozersky | |
| 2010/0168630 | A1 | 7/2010 | Cropper et al. | |
| 2010/0298749 | A1 | 11/2010 | Garth et al. | |
| 2011/0077567 | A1 | 3/2011 | Bledsoe | |
| 2012/0209162 | A1 | 8/2012 | Bar-Natan et al. | |
| 2012/0253251 | A1 * | 10/2012 | Thornton | A61F 5/028 602/19 |
| 2014/0100501 | A1 | 4/2014 | Burke et al. | |
| 2014/0276311 | A1 | 9/2014 | Hollister et al. | |
| 2014/0371646 | A1 | 12/2014 | Kozersky | |
| 2015/0290019 | A1 | 10/2015 | Garth et al. | |
| 2016/0045387 | A1 | 2/2016 | Lee et al. | |
| 2016/0089554 | A1 | 3/2016 | Perner | |
| 2016/0151190 | A1 | 6/2016 | Lurssen et al. | |
| 2016/0206467 | A1 * | 7/2016 | Glace | A61F 5/02 |
| 2016/0324678 | A1 | 11/2016 | Ingimundarson et al. | |
| 2017/0348134 | A1 | 12/2017 | Joseph et al. | |
| 2018/0303699 | A1 | 10/2018 | Romo et al. | |
| 2018/0325184 | A1 | 11/2018 | Roberts | |
| 2018/0353314 | A1 * | 12/2018 | Grim | A61F 5/028 |
| 2019/0070033 | A1 | 3/2019 | Heronen et al. | |
| 2020/0179153 | A1 | 6/2020 | Wang | |
| 2022/0226139 | A1 * | 7/2022 | Poker | A61F 5/022 |

OTHER PUBLICATIONS

U.S. Appl. No. 18/162,328, filed Jan. 31, 2023 Non-Final Office Action dated Mar. 31, 2025.

U.S. Appl. No. 18/162,345, filed Jan. 31, 2023, Non-Final Office Action dated May 20, 2025.

U.S. Appl. No. 18/162,367, filed Jan. 31, 2023, Non-Final Office Action dated Jun. 16, 2025.

* cited by examiner

FIG. 2A
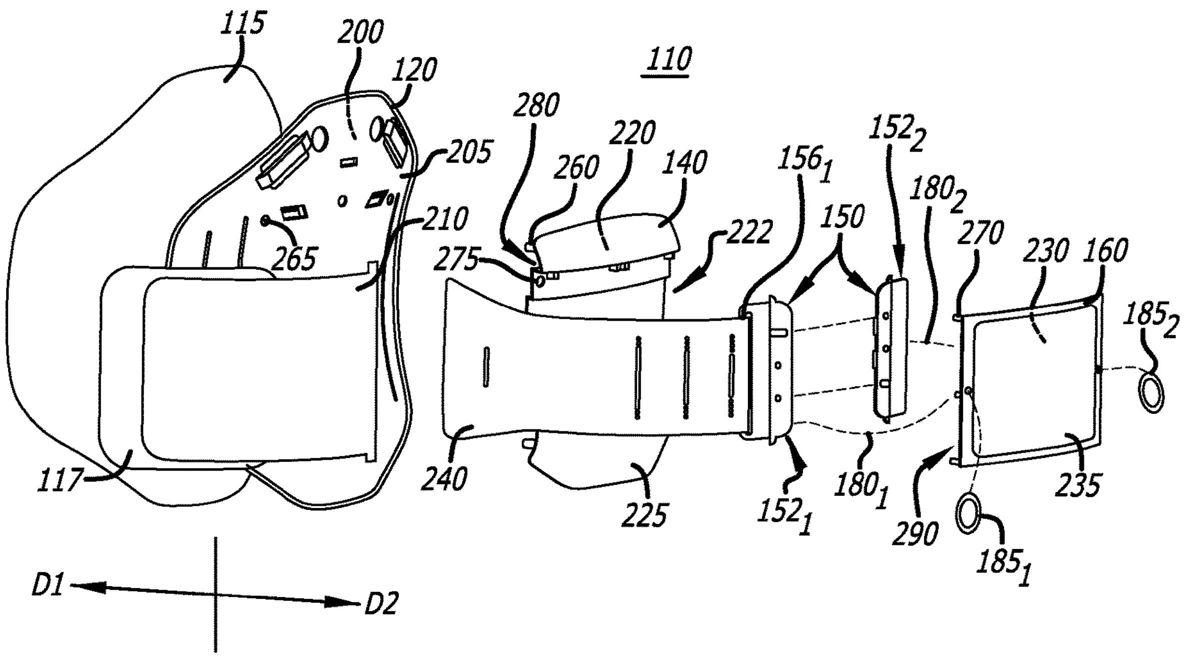
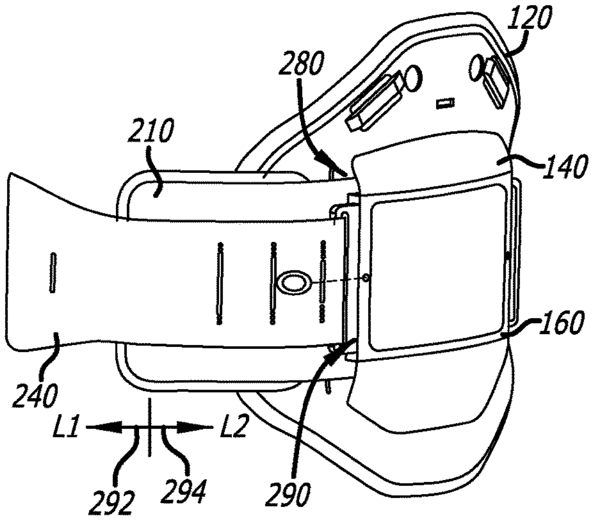
FIG. 2B

FIG. 19C
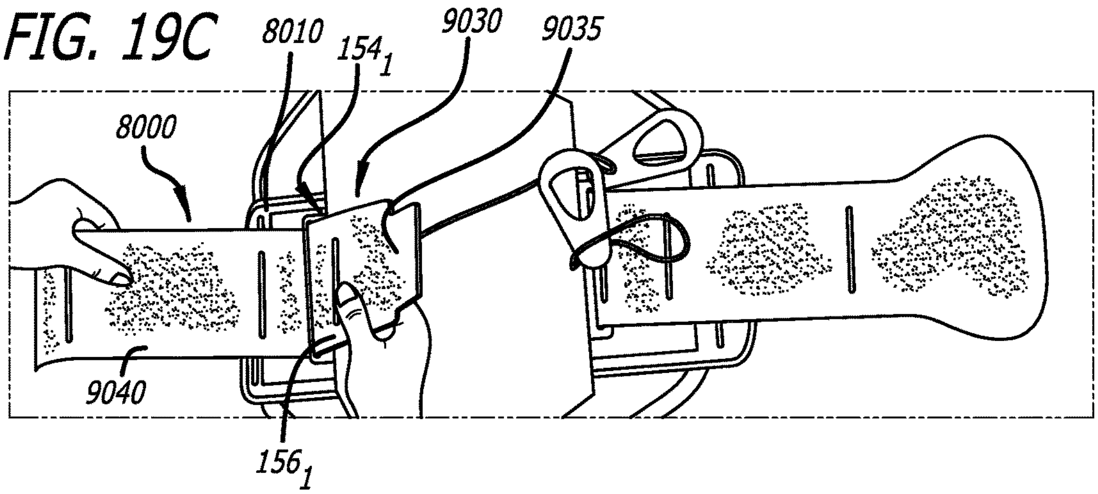
FIG. 19D
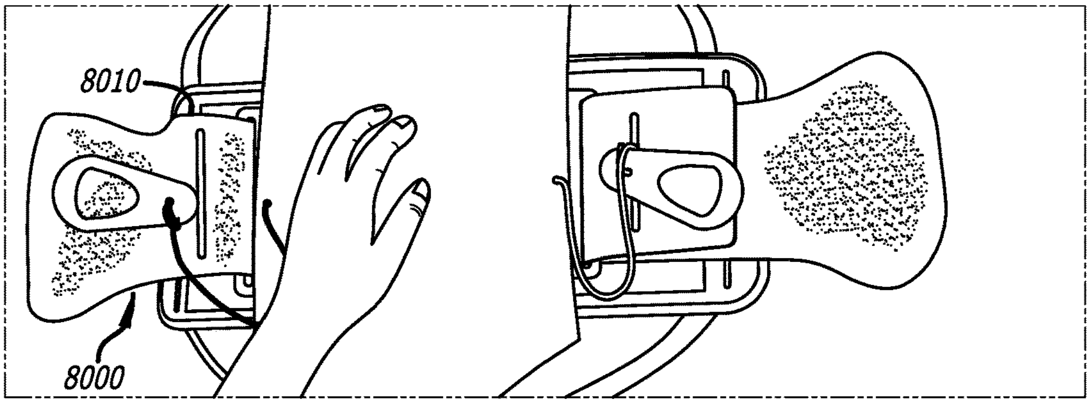
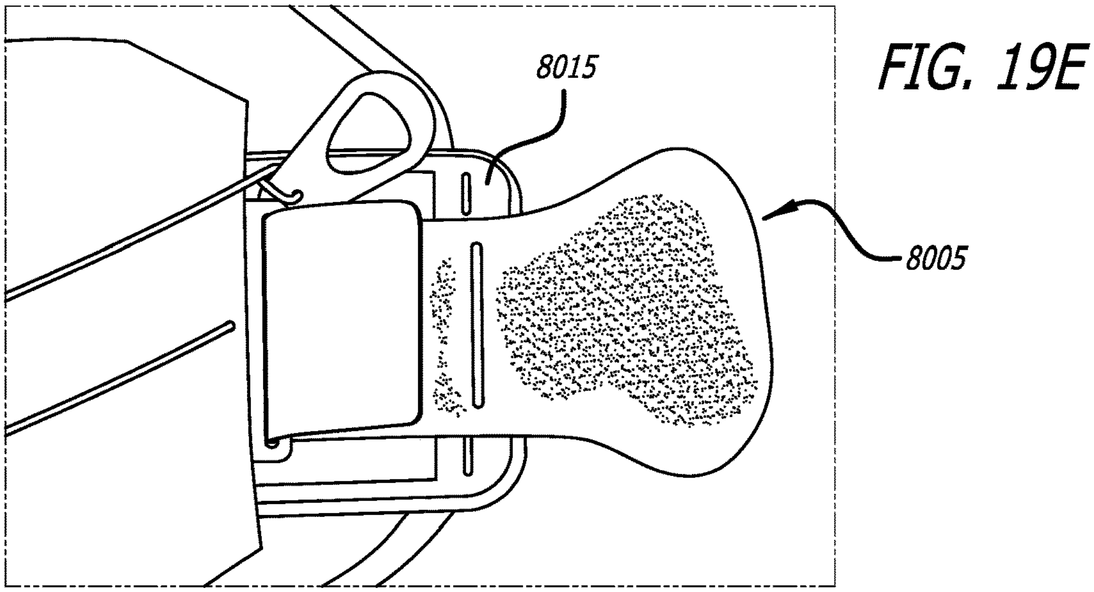
FIG. 19E

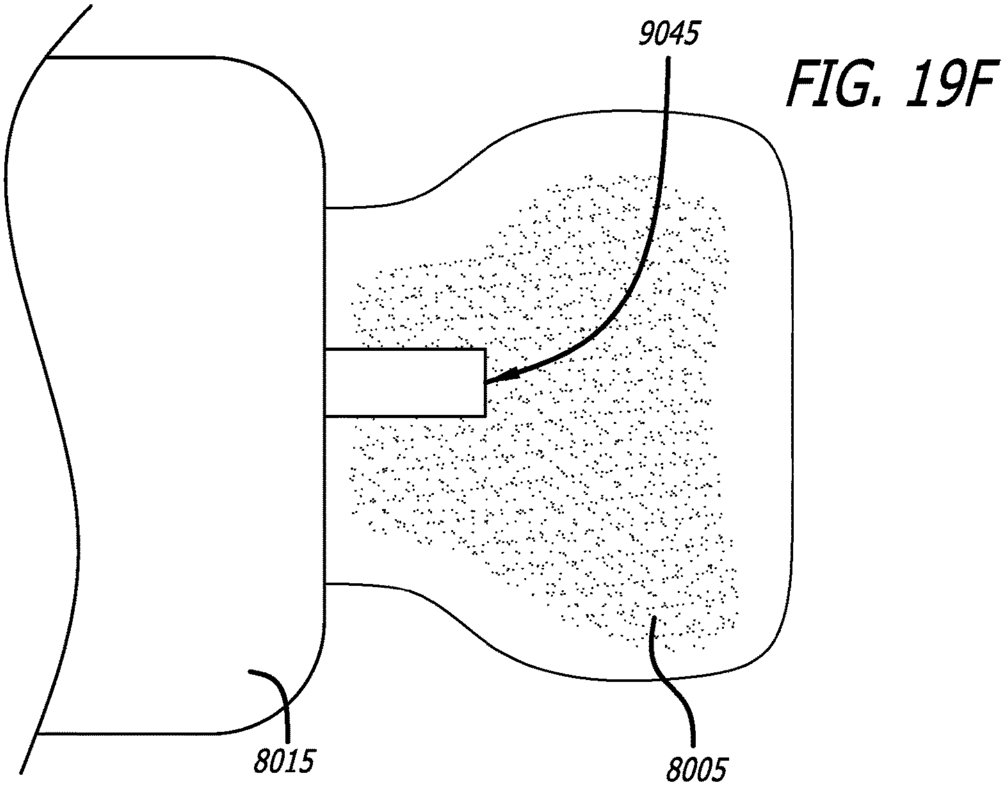
FIG. 19F
FIG. 19G
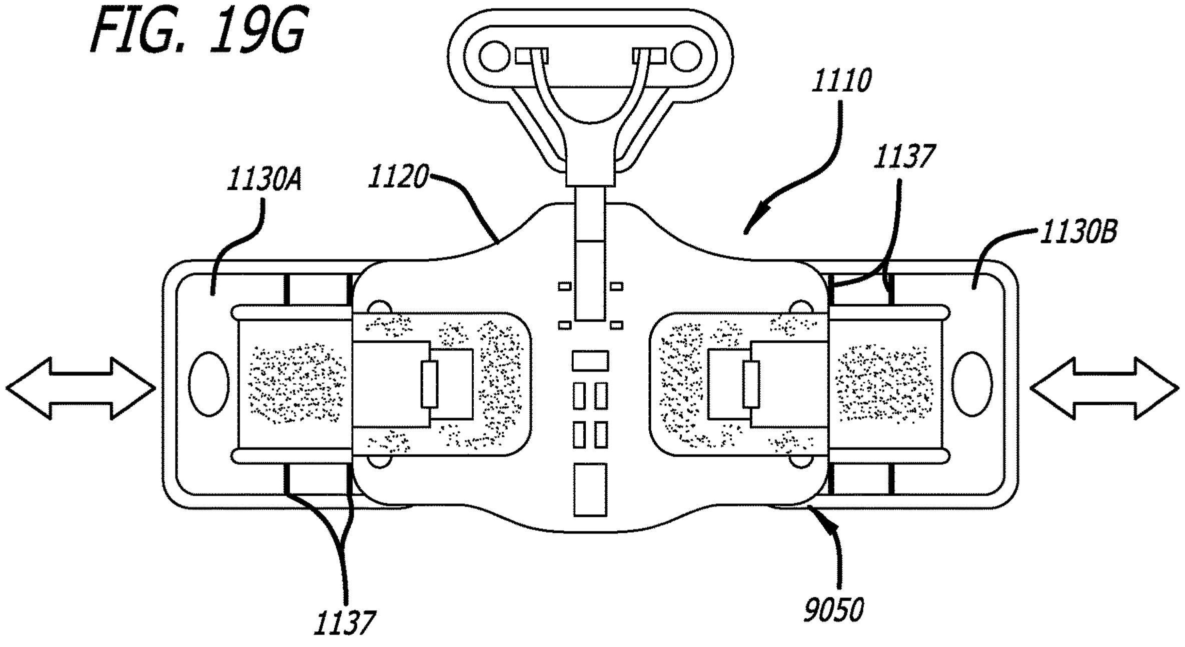

FIG. 20F
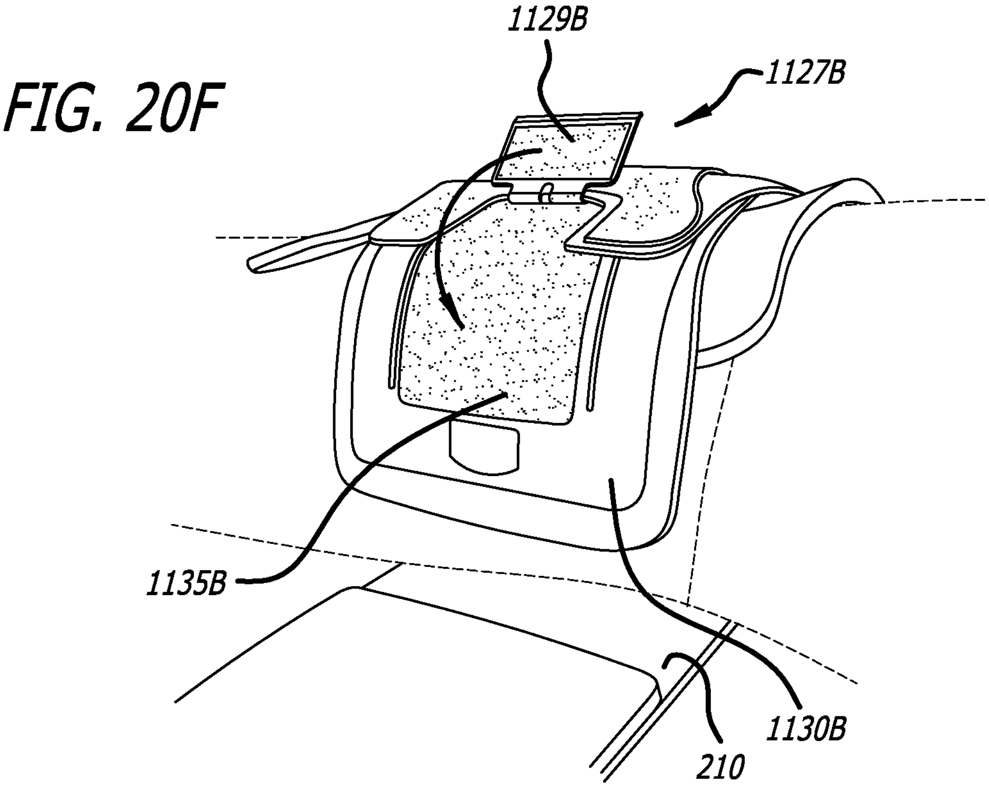
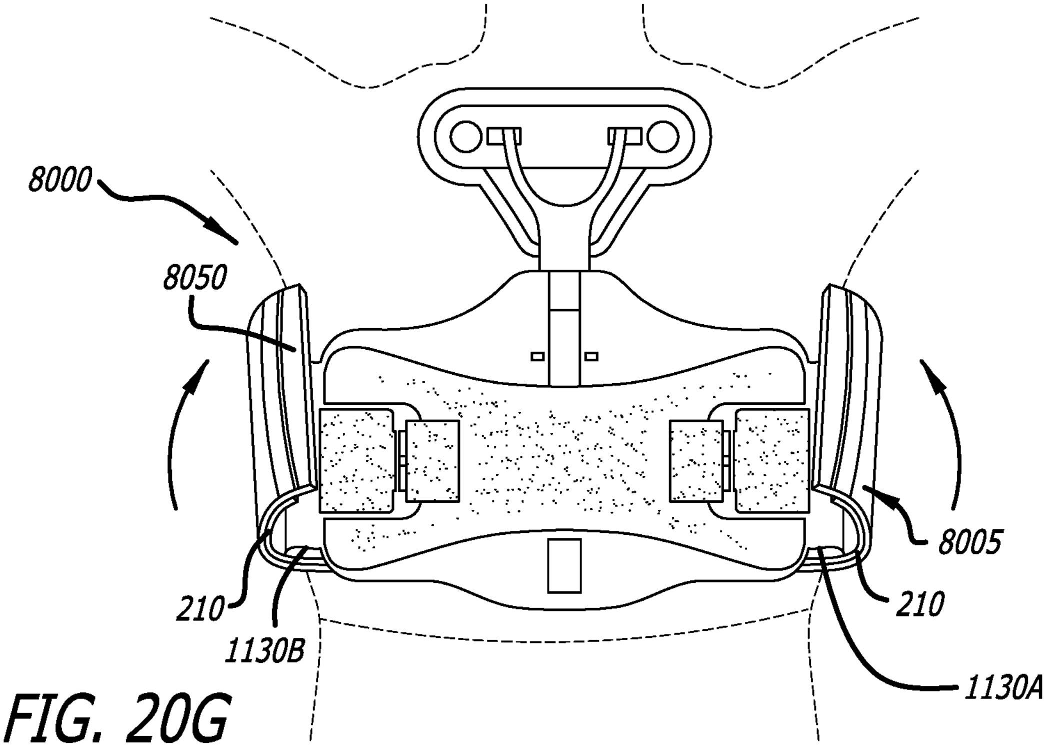
FIG. 20G

ORTHOPEDIC BRACE AND DONNING METHOD

CROSS-REFERENCE TO RELATED APPLICATIONS

This application claims the benefit of priority on U.S. Provisional Application No. 63/305,678 filed Feb. 1, 2022, the entire contents of which are incorporated by reference herein.

FIELD

Embodiments of the disclosure relate to the field of medical devices. More specifically, one embodiment of the disclosure relates to an orthopedic brace and donning method thereof.

GENERAL BACKGROUND

The following description includes information that may be useful in understanding the described invention. It is not an admission that any of the information provided herein is prior art or relevant to the presently claimed invention, or that any publication specifically or implicitly referenced is prior art.

Orthopedic braces (orthoses) usually need to be adjusted or customized in some manner to conform to the body part(s) being braced, and then properly positioned. A typical orthosis commonly has at least two portions, a rigid portion supporting a body part, and a flexible or semi-flexible portion securing the orthosis to the body. One type of orthopedic brace is referred to as a "thoracic-lumbar-sacral orthosis" or by the acronym "TLSO."

A TLSO is a brace that limits movement in a wearer's spine from the thoracic area (mid-back area) to the wearer's sacrum (lower-back area). At the same time, the TLSO allows a wearer's neck to move freely. This type of brace is normally used to provide support and stabilization of the spine after a back injury and/or surgery, and in some cases, may be utilized to address spinal pathologies.

One common problem associated with conventional TLSOs is the donning process is quite difficult, especially when the orthotist is trying to ensure that the TLSO properly fits to immobilize the patient as a proper fit of the orthosis normally provides the wearer with improved pain reduction and promotes healing. Conventional TLSOs rely on soft goods, namely a long belt extending from the posterior brace with a hook and loop fastener that is affixed to a complementary hook and loop fastener located on a top surface of the anterior brace, to secure the anterior brace to the posterior brace. Hence, the donning process may require the patient to be "log rolled" (moved face-down to face-up or vice versa) multiple times in order to adjust and fit the TLSO onto the patient. For example, the patient would be placed onto the posterior bracing system, then "log rolled" onto an anterior brace to allow the belt to be sized with excess belt strap being hidden. Thereafter, the patient may be "log rolled" one or more times to adjust the posterior bracing system or belt adjustment to better immobilize the patient. Avoidance of a complex (and in some cases painful) donning process would ensure more effective usage of TLSO-based orthopedic braces.

Furthermore, there are different braces for different conditions, including the usage of an orthopedic brace with a cervical collar, referred to as Cervical Thoracic Lumbar Sacral Orthosis (CTLSO). It would be advantageous to provide an orthopedic brace that features a uniform construction to enable transitioning from a TLSO to a CTLSO and vice versa.

BRIEF DESCRIPTION OF THE DRAWINGS

Embodiments of the invention are illustrated by way of example and not by way of limitation in the figures of the accompanying drawings, in which like references indicate similar elements and in which:

FIG. 2A is an exploded view of the exemplary embodiment of the posterior bracing system of FIG. 1.

FIG. 2B is an exemplary embodiment of the posterior bracing system of FIG. 1 with liner padding for donning.

FIGS. 19A-19I are exemplary embodiment of a donning process in configuration of the orthopedic device to be worn.

FIGS. 20A-20K are a second illustrative embodiment of the donning process for placement of the orthopedic brace onto a wearer.

DETAILED DESCRIPTION

Figure 1:
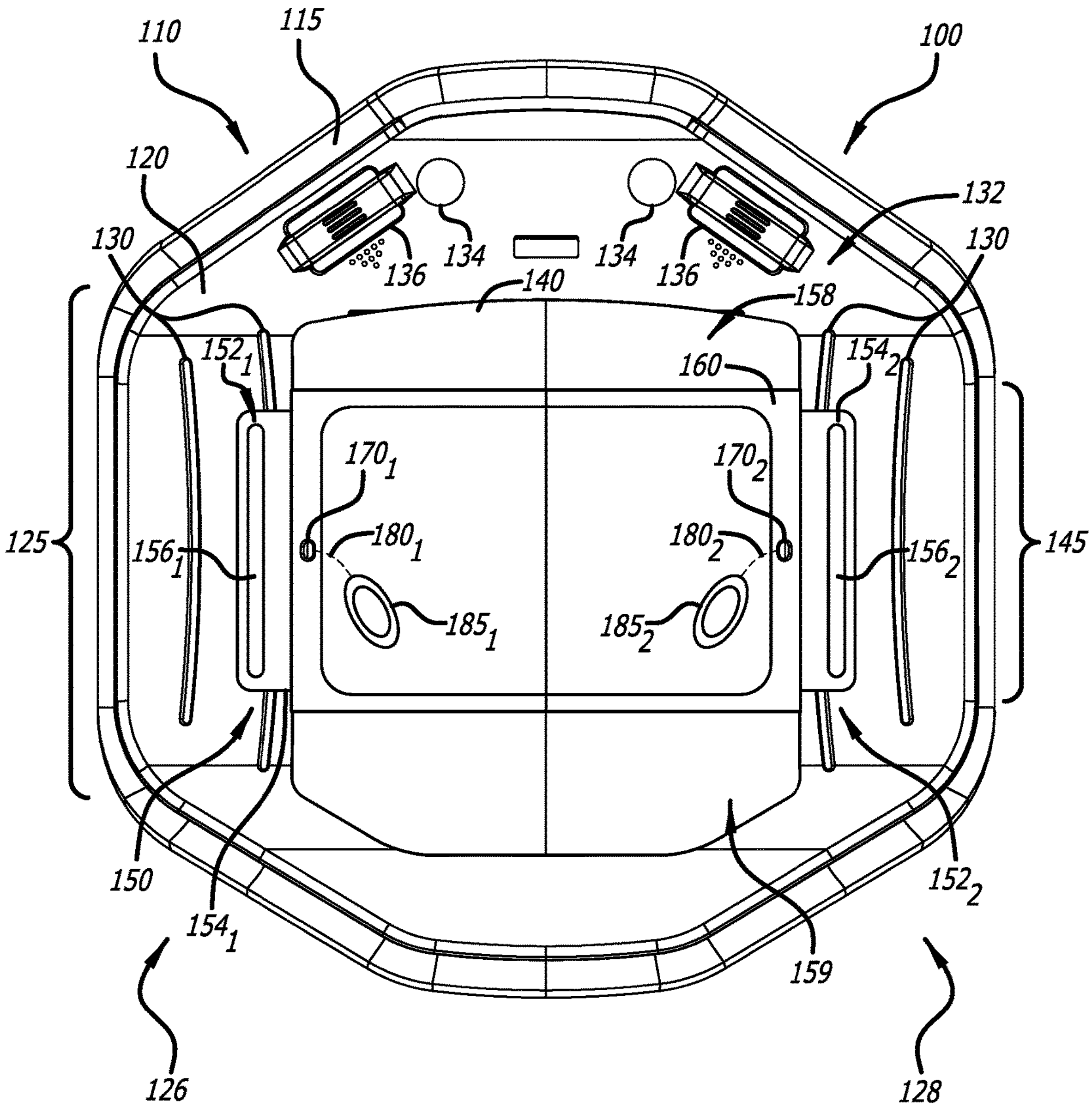
FIG. 1 is a perspective rear view of an exemplary embodiment of an orthopedic brace with a posterior bracing system.

Embodiments of the present disclosure generally relate to an orthopedic brace including a posterior bracing system and an anterior bracing system. According to one embodiment of the disclosure, the posterior bracing system features an orthosis fastening subsystem, which includes telescopic lateral panels that extend from opposite sides of the posterior bracing system and operate in concert with an adjustable belt to assist in donning of the orthopedic brace onto the patient. As described herein, the orthopedic brace may constitute any type of lumbar sacral orthosis (LSO), including a standard LSO (lower back brace belt) or other orthoses configured to provide greater patient immobilization, such as a thoracic LSO (TLSO), or a cervical TLSO (CTLSO) as described below.

When deployed as a TLSO or CTLSO or LSO, the posterior bracing system for the orthopedic brace may be configured in accordance with a layered component architecture including a posterior panel, a posterior cover, and a pulley cover. Each of these components may be formed with a rigid material, such as hardened plastic for example, to provide greater stiffness for immobilization of the patient. Herein, the posterior panel is shaped and sized to rest again the mid-to-lower portions of the patient's back to partially immobilize the spine of the patient. The posterior cover is sized to overlay a midsection area of the posterior panel, while the pulley cover is sized to overlay a midsection area of the posterior cover. This layered architecture creates distinct chambers for housing different components forming the orthosis fastening subsystem. For example, the posterior panel and posterior cover create a first chamber for housing and securing end portions of lateral (side) panels that can be slidably extended in a telescopic manner from side openings in the first chamber. Similarly, the posterior cover and the pulley cover create a second chamber for housing a pulley subsystem to which adjustable belt members are attached. The belt members are affixed to the telescopic lateral panels at a location based on sizing of the belt member. For example, full lateral extension of the belt member may compliment the arrangement of the telescopic lateral panels to extend from the first chamber by a distance consistent with the lateral movement of the belt members after affixation of the telescopic lateral panels.

According to one embodiment of the disclosure, as an illustrative example, the posterior cover is positioned to partially overlay a rear surface of the posterior panel, such as a midsection of the posterior panel. As a result, the first chamber is created between the front (anterior facing) surface of the posterior cover and the rear (posterior facing) surface of the posterior panel. Additionally, the pulley cover is positioned to partially overlay a rear surface of the posterior cover, such as covering a recessed area formed as part of the posterior cover. As a result, the second chamber is created between the front (anterior) surface of the pulley cover and the rear (posterior) surface of the posterior cover.

Similarly, the anterior bracing system features an orthosis fastening subsystem, which includes telescopic lateral panels that extend from opposite sides of the anterior bracing system and are locked in place by locking mechanisms on the opposing sides of the anterior bracing system such that extension of each the telescopic lateral panel assists in configuring an overall sizing of the orthopedic brace when coupled with a posterior bracing system. The orthopedic brace may be placed around a patient's torso. As described herein, the orthopedic brace may constitute any type of lumbar sacral orthosis (LSO), including a standard LSO (lower back brace belt) or other orthoses configured to provide greater patient immobilization, such as a thoracic LSO (TLSO), or a cervical TLSO (CTLSO) as described below.

When deployed as a TLSO or CTLSO, the anterior bracing system for the orthopedic brace may be configured in accordance with an architecture including an anterior panel having locking mechanisms on opposing sides and telescopic lateral panels slidably coupled to an interior (or "rear") side of anterior panel. Thus, the anterior bracing system operates such that the telescopic lateral panels are coupled to the anterior panel and slidably extend (or retract) with the locking mechanism of the anterior panel rotating to removably couple with the telescopic lateral panels thereby locking such in a given position. As a result, the telescopic lateral panels may be extended or retracted as a sizing mechanism based on a size of a patient's torso, e.g., for the purposes of immobilizing the patient (the wearer).

Each of the components of the anterior bracing system may be formed with a rigid material, such as hardened plastic for example, to provide greater stiffness for immobilization of the patient. Herein, the anterior panel is shaped and sized to rest again the mid-to-lower portions of the patient's front torso to partially immobilize portions of neuromuscular and skeletal systems, e.g., the spine of the patient.

As discussed below and illustrated in the accompanying figures, the interior of the anterior panel includes a plurality of lateral panel guide posts (guide posts) that are configured to couple with guide channels of the telescopic lateral panels. In particular, the combination of the coupling posts of the anterior panel and the guide channels of the telescopic lateral panels enables the extension (or retraction) of the telescopic lateral panels in a controlled manner. Further, locking mechanisms disposed on opposing sides of the exterior of the anterior panel rotate around a hinge and couple with an exterior side of the telescopic lateral panels to lock such in a desired extended or retracted position. The desired extended or retracted position may be in accordance with particular size indicia provided on the exterior side of each telescopic lateral panel.

The lateral panel locking mechanisms (locking mechanism) may each include a hinge and a rotatable locking member that is rotatable around the hinge. The locking mechanisms may be configured to removably lock (or retain) the telescopic lateral panels (lateral panels) in a preferred position through the use of a hook-and-loop fastening system. More particularly, an exterior portion of a lateral panel includes an unbroken loop (UBL) material while a first side of a rotatable locking member includes a hook material to couple with the UBL material such that as the rotatable locking member is rotated and contacts the UBL material, the lateral panel is locked (or retained) in its current position. A second side of the rotatable locking member may have disposed thereon UBL material for coupling with a belt of a posterior bracing system of the orthopedic brace.

The anterior bracing system may also include an extension rod extending vertically upward from the anterior panel. The distal end of the extension rod may have a wishbone extension attachment (wishbone coupler) coupled thereto. The wishbone coupler may further couple with a plurality of attachments thereby providing interchangeability among attachments such as a support chest plate when the orthopedic brace is configured for a TLSO deployment and a CTO clip, which further couples to a cervical brace when the orthopedic brace is configured for a CTLSO deployment.

According to one embodiment, a patient may be positioned on his or her back, e.g., laying on top of a posterior bracing system and the anterior bracing system may be placed on the patient's front torso such that a liner (padding) rests against the patient. The anterior panel is shaped with a contour intended to conform to the curvature of a front torso region of the patient. The exterior facing surface of the anterior may include two portions of UBL material on opposing sides with each portion at least partially surrounding a locking mechanism. A rotatable locking member of a locking mechanism is rotatable from an open position to a closed position, where in the closed position the rotatable locking member contacts and couples with the lateral panel causing the lateral panel to be retained in its current position.

Thus, the anterior bracing system may be sized to fit a patient through extension of the lateral panels laterally (outwardly). Upon reaching a desired length of the lateral panel (e.g., an amount a distal edge of the lateral panel has extended laterally from an edge of the lateral panel), the rotatable locking member is rotated from the open position to the closed position and placed in contact with the exterior facing side of the lateral panel causing the lateral panel to be retain in its current position. The lateral panels may lay over a portion of the patient's side torso. As a result, the length of the lateral panel correlates to the sizing of the anterior bracing system.

The lateral panels extend (or retract) in a substantially perpendicular direction from the patient's midline. The lateral panels may include one or more slot rails configured to receive guide posts extending in a posterior direction (e.g., toward the patient body) from the anterior panel. Thus, movement of the lateral panels is restricted to be in substantially a perpendicular direction from the patient's midline.

Herein, the connectivity between the posterior bracing system and the anterior bracing system is accomplished through the belt members attached to the telescopic lateral panels and support straps extending between these bracing systems. More specifically, after extending the belt members and telescopic lateral panels of the posterior bracing system to a desired length (sizing), the telescopic lateral panels may be partially wrapped around a waist area of the wearer and partially overlay extended lateral panels of the anterior bracing system. In particular, the telescopic lateral panels may extend and bend with a curvature to remain adjacent to a side of the wearer after attachment of the anterior bracing system. A first portion of each belt members extends from the pulley subsystem and overlays its corresponding lateral panel. A second portion of each belt member extends beyond an edge of the corresponding lateral panel for attachment to a front surface of the anterior panel. This attachment may be accomplished by a loop and hook fastener with unbroken loop (UBL) fabric placed on the front surface of the anterior panel and a rear surface of the belt member including hooks for attachment to the UBL fabric so as to operate as a hook and loop fastener.

Each belt member includes a first end for attachment to the pulley subsystem and a second end for attachment to the front surface of the anterior panel. The second end of the belt member includes a rigid portion that is oriented widthwise (longitudinally) and is inserted within fabric utilized for the second end. Guide straps integrated as part of the fabric for the second end of the belt member are oriented longitudinally from the integrated rigid portion to form a loop construction when the guide straps are placed into a first operational state. Herein a first guide strap includes a hook fastener positioned on a first surface (rear-facing surface) for attachment to the UBL fabric deployed over a first (front-facing) surface of the second guide strap to form a loop extending from a front surface of the anterior panel.

The first and second guide straps may be disconnected and placed into a second operational state. In this state, in lieu of being connected together to form a loop accessible by the wearer (or a third party) and positioned on the front surface of the anterior panel, the first and second guide straps may be disconnected, wrapped around an edge portion of the anterior panel of the anterior bracing system, and the hook fastener of the first guide strap is securely attached to the UBL fabric deployed on the second guide strap. As a result, the belt member is connected to the anterior panel and the wearer is prevented from existing the orthopedic brace by disengaging this belt member from the anterior panel. Instead, the other belt member remains the first operational state (loop) to allow for disengagement of that belt member from the anterior panel to allow a side opening for the wearer to remove the orthopedic brace.

Operating in tandem, the posterior bracing system may be coupled to the anterior bracing system through a plurality of support straps. As described below, each support strap includes a first end segment and a second end segment. The first end segment of the support strap may include a hook and loop fastening system. For example, a loop fastener may be positioned on a first surface of the first end segment and a hook fastener may be positioned on the first surface of the first end segment at a distal end of the first end segment. Hence, after the distal end of the first end segment is inserted through a strap slot positioned within an extension panel of the posterior bracing system (or through a first opening of a strap guide in the posterior panel aligned with a slot in the extension panel) and folded back, the hook fastener may be affixed to the loop fastener. This connects the support strap to the posterior bracing system. The second end segment includes a buckle positioned at a distal end of the second end segment for attachment to a cert. Multiple buckles may be connected to each snap connector on the support chest plate described below.

More specifically, for connecting each of a first plurality of support straps between the posterior bracing system and the anterior bracing system, each support strap may be coupled to one or more strap holding members (e.g., a strap slot in the extension panel or strap guide in the posterior panel) for positioned the support straps over the shoulder. According to one embodiment of the disclosure, the strap holding member may include a single slot formed toward a top portion of the extension panel in which the distal end of the first end segment of the support strap is inserted from an anterior side to a posterior side of the strap slot and looped back over the top portion of the extension panel. The distal end of the first end segment is attached to another portion of the first end segment to create a looped end fastened to the extension panel.

Additionally, or in the alternative, each support strap of the plurality of support straps (or a second plurality of support straps) may be coupled to a strap guide, which includes an opening formed within a top portion of the posterior panel with a member positioned to span across the opening to create a first opening and a second opening. The first and second openings are aligned with a strap slot located toward a bottom portion of the extension panel, where the strap slot has an opening of an area to allow a support strap to be inserted into and returned from the strap slot. As an illustrated example, a distal end of the first end segment of each support strap may be inserted through a first opening of the strap guide and looped back around the member and through a second opening of the strap guide. As a result, the member is configured as a termination point for the first end segment of the support strap. The second end segment of the support strap may be configured with a buckle positioned at a distal end of the second end segment for attachment to the support chest plate.

These plurality of support straps may be positioned over the shoulder of the wearer. However, where a first plurality of support straps are coupled to the strap slots formed towards the top portion of the extension panel, one or more support straps may be coupled to above-described strap guides to extend between the posterior bracing system and the anterior bracing system under the axilla of the wearer. This provides additional immobility of the orthopedic brace.

I. Terminology

In the following description, certain terminology is used to describe aspects of the invention. For example, the term "member" may be construed as a structural component of an orthopedic brace. In certain situations, a member may include a component covered by soft goods such as one or more textiles, one or more fabrics (woven fabrics and/or non-woven fabrics), leathers, and/or another covering material. These soft goods may feature "loop" type fasteners or other variants to which a "hook" type fastener may be attached or may feature a hook-type fastener for attachment to a loop-type fastener. In other situations, the member may be soft goods attached to another structural component of the orthopedic brace such as a textile or fabric sewn to form together such as a knit textile with pockets in which the structural component(s) can be positioned within the pocket(s).

The term "chamber" is a partially enclosed housing, namely a structure having partially enclosed perimeter except for one or more openings, such as at least two openings at opposite sides along the periphery for example. As a result, a partially enclosed chamber operates as a structure that is configured to secure, maintain and protect orthosis fastening sub system components.

The term "attach" and other tenses of the term (attached, attaching, etc.) may be construed as physically connecting a first member to a second member. A "fastener" may be construed as any physical component that is used to attach different members together. An illustrative example of different types of fasteners and fastening techniques may include, but are not limited or restricted to snaps, buttons, clasps, buckles, adhesives, sewing, heat sealing (or melting), gluing, knitting, or other physical coupling techniques such as a hook and loop connection.

The terms "rigid" or "rigidity" with respect to a member or portion of a member may be construed as the member being configured to at least partially resist bending or deformation. According to this definition, different lengths of a given structure and composition can be rigid at a shorter length, and flexible at a longer length. As used herein, the term "rigid" with respect to a member or portion of a member may be construed as the member could be permanently deformed or broken if bent or twisted by at least 90°. Examples of a rigid member may include, but is not limited or restricted to the posterior panel, the anterior panel or the extension panel, where the telescopic lateral panels are rigid, but are flexible to support placement into a concave-shape without breaking.

Finally, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure is to be considered as an example of the principles of the invention and not intended to limit the invention to the specific embodiments shown and described.

II. General Architecture—Posterior Bracing System

Referring to FIG. 1, a perspective rear view of an exemplary embodiment of a posterior bracing system 110 deployed as part of an orthopedic brace 100 is shown. Herein, the posterior bracing system 110 features a posterior panel 120 that is oriented, when worn, to generally reside or is substantially in parallel with a frontal plane of the patient. As shown, a filler 115 (padding) may be inserted adjacent to an anterior surface of the posterior panel 120. The posterior panel 120 provides support along a thoracic and lumbar regions of the patient's spine.

As further shown, the posterior bracing system 110 further features a plurality of structural members layered onto the posterior panel 120 to create a plurality of chambers therebetween. These structural members may include, but are not limited or restricted to a posterior cover 140 and a pulley cover 160. The posterior cover 140 is coupled to a curved, midsection region 125 of the posterior panel 120. This midsection region 125 is generally concave in shape to conform to the thoracic and lumbar regions of a patient's spine. One or more slotted openings 130 are positioned on each side (left 126, right 128) of the midsection region 125 to lessen lateral rigidity of the posterior panel 120 to allow for lateral and anterior movement of the sides of the posterior panel 120 when worn. As also shown, a top area 132 of the posterior panel 120 features locking slots 134 for retention of extension panels (not shown) and strap guides 136 for retention of an attachment strap (not shown).

The pulley cover 160 is coupled to the posterior cover 140, namely at a midsection region 145 of the posterior cover 140. This midsection region 145 of the posterior cover 140 features a recessed area (not shown), which is shaped to maintain a pulley subsystem 150 including a plurality of pulley bases $152_1$-$152_2$. Each of the pulley bases $152_1$ or $152_2$ includes (i) a base member $154_1$ or $154_2$ with a plurality of pulley members (not shown) positioned in a staggered orientation and interconnected with a designated pulley cord $180_1$ or $180_2$ with a handle $185_1$ or $185_2$, and (ii) a belt slot $156_1$ or $156_2$ positioned on an outer lateral edge of the pulley base member $154_1$ or $154_2$. Each pulley cord $180_1$ or $180_2$ is threaded through cord passage apertures $170_1$ or $170_2$ that reside within the same traversal plane. The pulley cover 160 is smaller in size (e.g., width and height) than the posterior cover 140 so as to overlay the recessed area of the posterior cover 140 so that the pulley cover 160 refrains from covering a top cover region 158 and a bottom cover region 159 of the posterior cover 140.

Referring to FIG. 2A, an exploded view of an exemplary embodiment of the posterior bracing system 110 of FIG. 1 is shown. Herein, the posterior bracing system 110 features the posterior panel 120, the posterior cover 140 and the pulley cover 160 as shown in FIG. 1. The liner 115 is positioned anterior to a front surface 200 of the posterior panel 120. Furthermore, a plurality of lateral panels 210 are made of a rigid or semi-rigid material such as any type of hardened, flexible plastic (e.g., sheet of polyethylene, polycarbonate, etc.) and are positioned within a first chamber 280 (see also FIG. 2B) formed between a rear surface 205 of the posterior panel 120 and a front surface 220 of the posterior cover 140 (and adjacent to another liner 117). The pulley subsystem 150 is positioned within a second chamber 290 (see also FIG. 2B), which is formed between a rear surface 225 of the posterior cover 140 and a front (anterior) surface 230 of the pulley cover 160. Adjustable belt members 240 are attached to the belt slots $156_1$-$156_2$ formed within the pulley bases $152_1$-$152_2$.

Figure 4A:
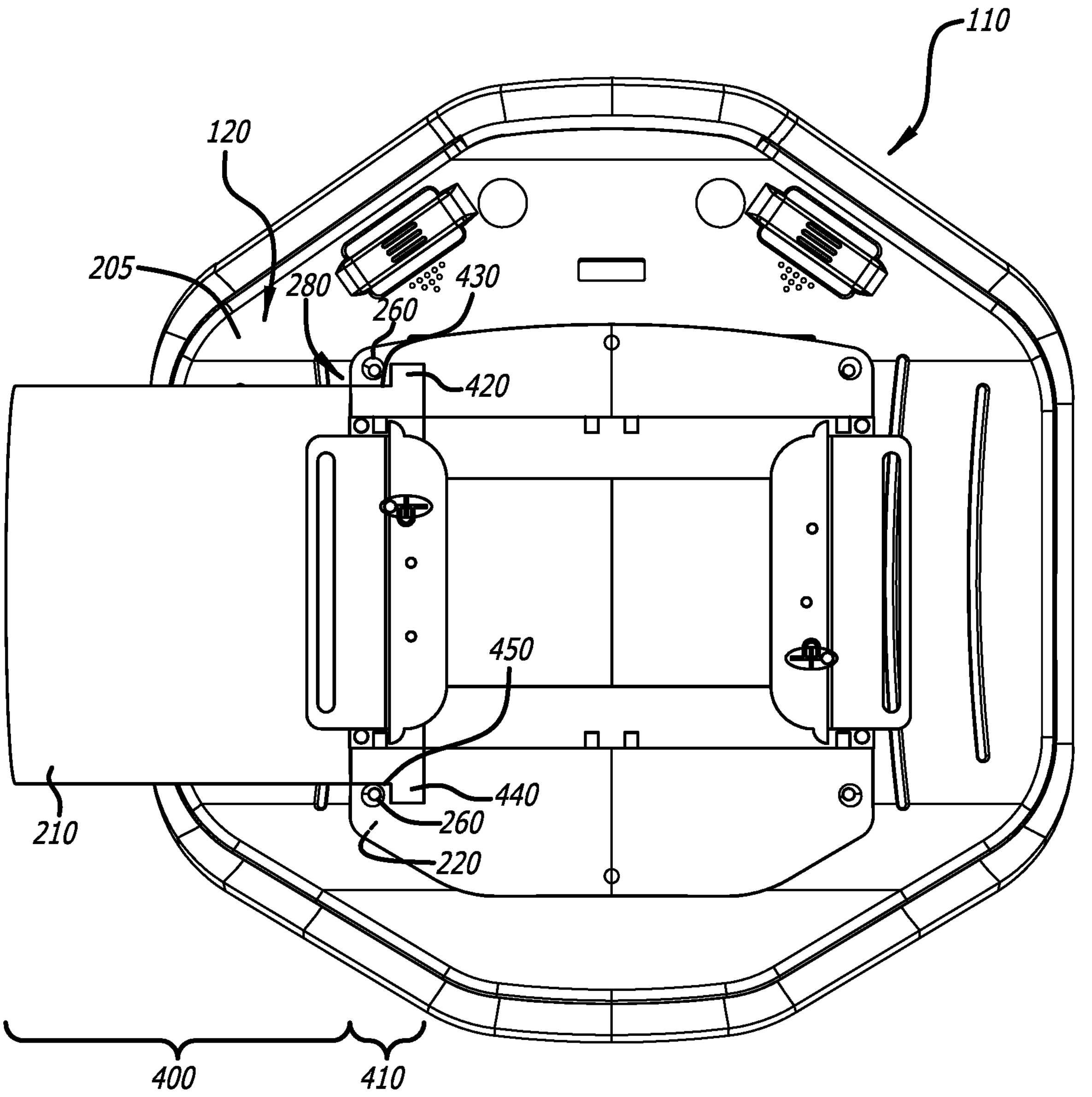
FIG. 4A is a top-down planar view of the brace adjustment system featuring telescopic panels and a belt deployed between the posterior panel and the posterior cover of FIG. 2.
Figure 4B:
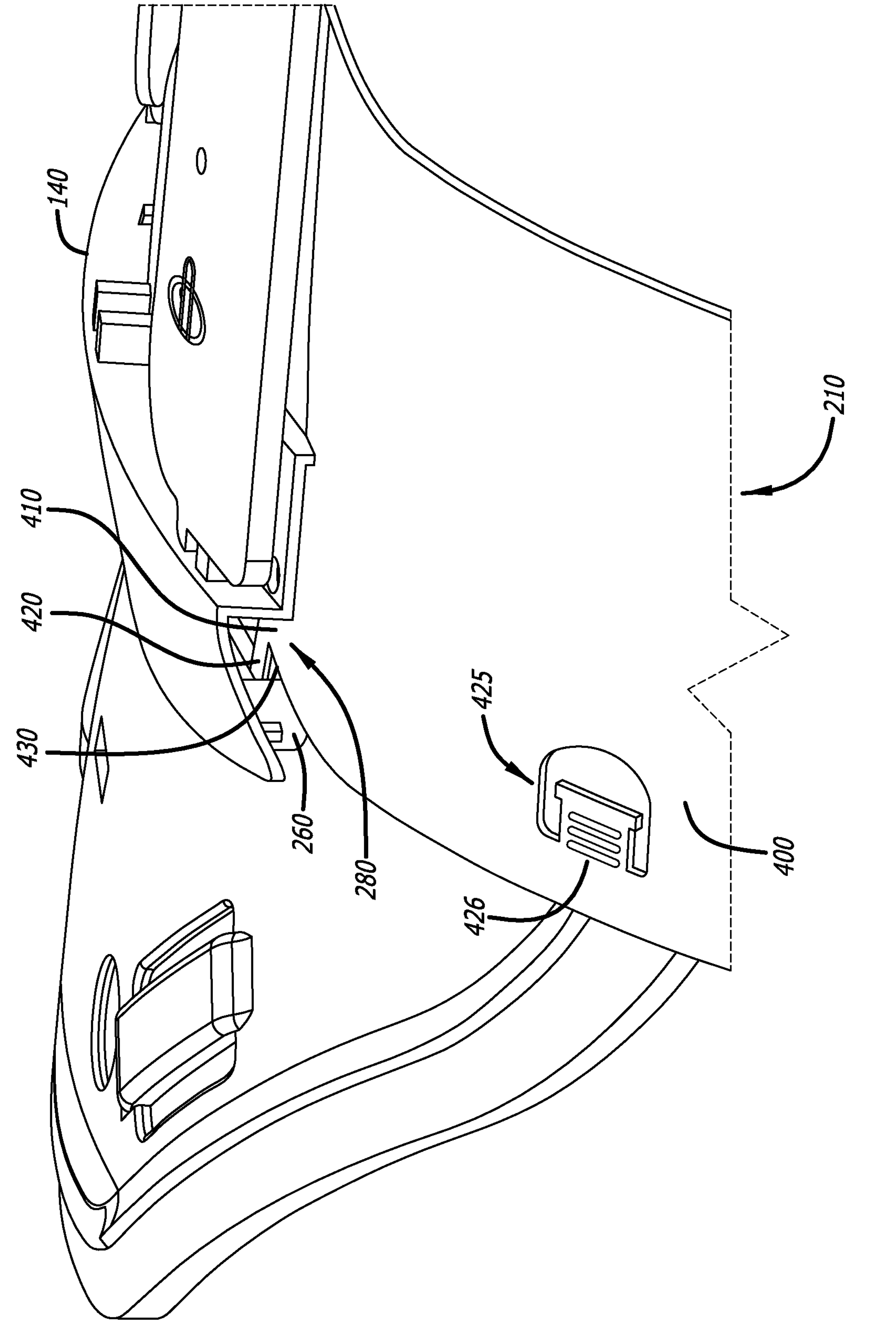
FIG. 4B is a cut-away view of the brace adjustment system illustrating stops including a first stop type to preclude continued extension of the telescopic lateral panel from the first chamber formed between the posterior panel and the posterior cover.

More specifically, the front surface 220 of the posterior cover 140 includes a plurality of posts 260, which are coupled to the posterior panel 120, where such coupling may be realized by insertion of the posts 260 into correspond support apertures 265 within the posterior panel 120 and permanently fused thereto (e.g., coupled together by a heat staking process). The posts 260 operate as (i) spacers to provide structural integrity by maintaining substantially constant width to side openings formed within the first chamber 280 (see FIG. 2B) for adjustment of the telescopic lateral panels 210 inward and outward from the first chamber 280 and (ii) stops to preclude complete removal of the lateral panels 210 from the first chamber 280 by tab portions of the lateral panels 210 engaging with the posts 260 as shown in FIGS. 4A-4B and described below.

Herein, according to one embodiment of the disclosure, the telescopic lateral panels 210 provide support by lessening circumferential pressure and helping with stabilizing the spinal system from bending sideways (coronal plane). The rigid, plastic lateral panels 210 may extend from sacrococcygeal junction area and terminate just inferior to the scapular spine. In combination with lateral panels associated with an anterior bracing system (see system 1110 of FIG. 10A) that extend from symphysis pubis to the sternal notch, soft liner, the lateral panels 210 assist in restricting gross trunk motion in sagittal, coronal, and transverse planes as well as provides lateral strength.

Additionally, the pulley cover 160 features the front surface 230 that also includes a plurality of posts 270. However, the posts 270 may be removably coupled to support apertures 275 formed within the posterior cover 140. The posts 270 operate as spacers, which provide the structural integrity to resist substantial narrowing or closure of side openings formed within the second chamber 290 in response to forces exerted on the pulley cover 160 in an anterior direction D1 or forces exerted on the posterior cover 140 in a posterior direction D2. This allows the belt slots $156_1$-$156_2$ located on the pulley bases $152_1$-$152_2$ to be exposed from the second chamber 290 and unencumbered during usage.

Referring to both FIGS. 2A-2B, the pulley bases $152_1$-$152_2$ are interconnected by the pulley cords $180_1$-$180_2$, where the tightening of one or both of the pulley cords $180_1$-$180_2$ (i.e., pulling on the handle $185_1$ at the end of the pulley cord $180_1$) causes both pulley bases $152_1$-$152_2$ to traverse inwardly towards each other along a guide channel 222 formed on the rear surface 225 of the posterior cover 140. During traversal, one or more of the orthopedic belt members 240 is tightened. During such tightening, the pulley bases $152_1$-$152_2$ move inwardly towards each other, which cause the length of each of the lateral panels (e.g., lateral panel 210) and its corresponding belt member 240, respectively extending from the first and second chambers 280 and 290, to be reduced as each belt member 240 is coupled to its corresponding lateral panel via hook and loop fastener, a loop connection attached to a surface of the belt member 240 and fed through a slot in the lateral panel 210 for attachment to a complementary fastener on the lateral panel. As a result, during adjustment, both the lateral panel 210 and its corresponding belt member 240 may be moved along a first lateral direction (L1) 292 away from the first and second chambers 280 and 290. However, during tightening, the lateral panel 210 and its corresponding belt member 240 is drawn back into the first chamber 280 and second chamber 290 in accordance with a second lateral direction (L2) 294, as described in more detail below.

Figure 3A:
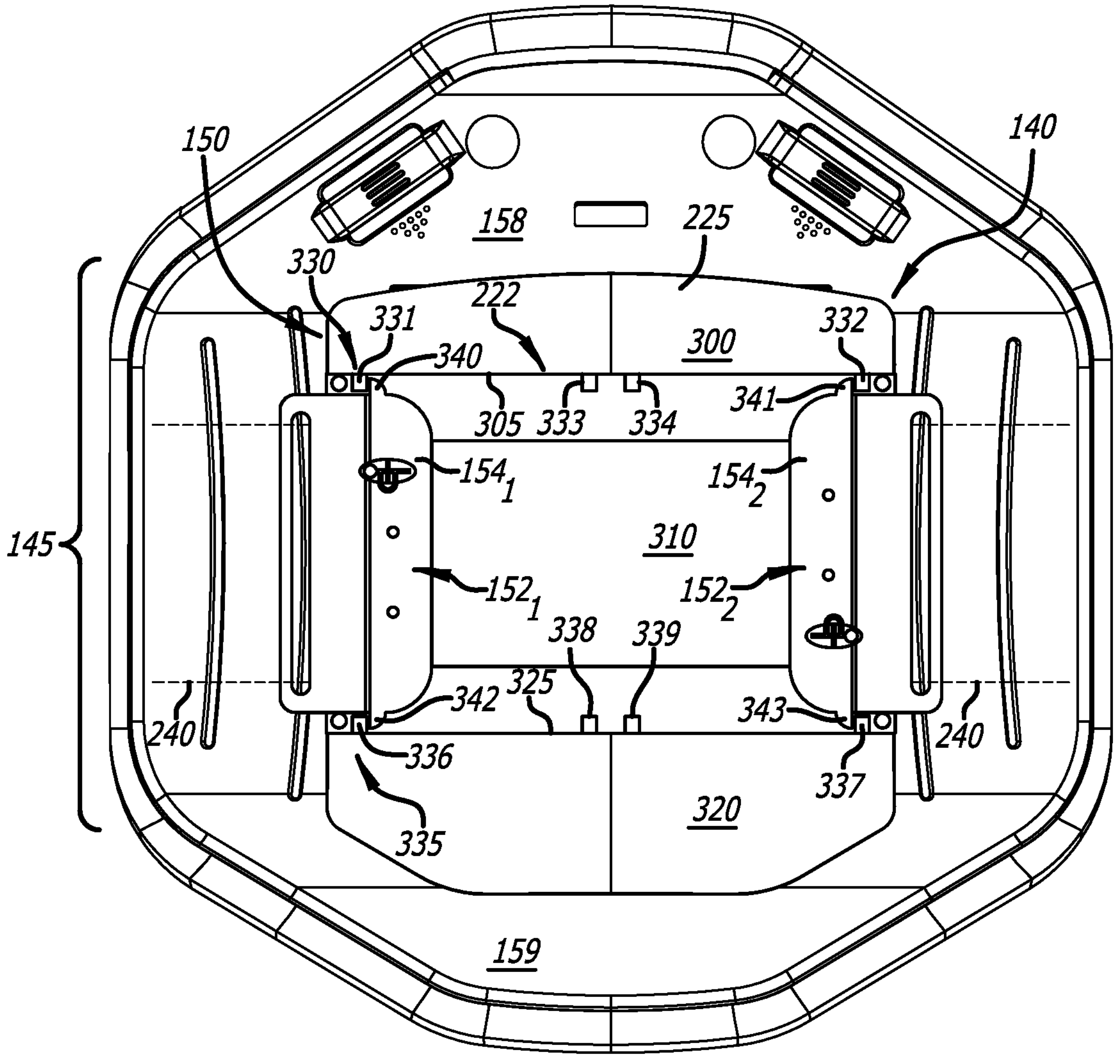
FIG. 3A is a top-down planar view of an exemplary embodiment of the pulley subsystem implemented with a guide channel formed within the posterior cover of FIG. 2A.

Referring to FIG. 3A, a top-down planar view of an exemplary embodiment of the pulley subsystem 150 implemented with the guide channel 222 formed within the posterior cover 140 is shown. Illustrating a rear surface 225 of the posterior cover 140, the posterior cover 140 is structured with the midsection cover region 145 integrated with and interposed between the top cover region 158 and the bottom cover region 159. The midsection cover region 145 features the guide channel 222 formed by a first guide member 300, a second guide member 310, and a third guide member 320.

As further shown in FIG. 3A, a first set (two or more) of pulley stops 330 are positioned along a side surface 305 of the first guide member 300 and a second set of pulley stops 335 are positioned along a side surface 325 of the third guide member 320. The first and second sets of pulley stops 330 and 335 are positioned to prevent the pulley bases $152_1$ and $152_2$ from being accidentally slid and removed from the guide channel 222. More specifically, each pulley base member $154_1$ and $154_2$ features a first flange 340 and 341, which is positioned to engage with one of the first set of pulley stops 330 (e.g., pulley stops 331 and 332) when each belt member 240 is set to a prescribed size and is fully extended from the second chamber 290. Similarly, each pulley base member $154_1$ and $154_2$ features a second flange 342 and 343, which is positioned to engage with one of the second set of pulley stops 335 (e.g., pulley stops 336 and 337) when each belt member 240 is set to a prescribed size and is fully extended from the second chamber 290. As an optional feature, besides pulley stops 331-332 and 336-337, the first and second set of pulley stops 330 and 335 may include pulley stops 333-334 and 338-339 to prevent further inward movement of the pulley bases $152_1$ and $152_2$ beyond a prescribed location.

Figure 3B:
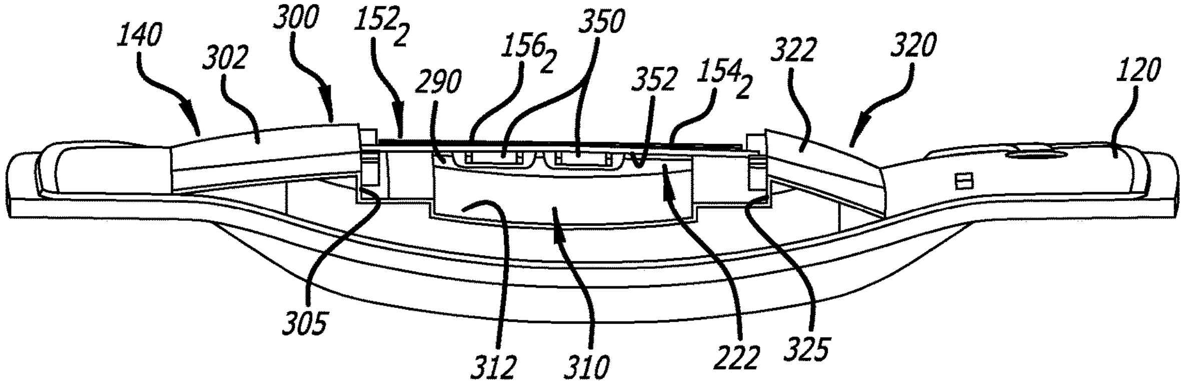
FIG. 3B is a side view of an exemplary embodiment of the posterior cover illustrating a second chamber formed, at least in part, by the guide channel.

Referring now to FIG. 3B, a side view of an exemplary embodiment of the posterior cover 140 is shown, which illustrates the second chamber 290 formed, at least in part, by the guide channel 222. Herein, given that the posterior panel 120 is shaped to conform to the contours of the thoracic and lumbar back regions, a rear-facing surface 312 of the second guide member 310 is positioned below a rear-facing surface 302 of the first guide member 300 and a rear-facing surface 322 of the third guide member 320. The rear-facing surface 302 of the first guide member 300 is generally orthogonal to the side surface 305 of the first guide member 300, and the rear-facing surface 322 of the third guide member 320 is generally orthogonal to the side surface 325 of the third guide member 320. This construction provide sufficient clearance for pulleys 350 mounted on a front-facing surface 352 of the pulley base member (e.g., pulley base member $154_2$ of the pulley base $152_2$), as the pulley base $152_2$ slides along the first and third guide members 300 and 320 in response to forces applied to the belt slot $156_2$ and/or forces applied via the pulleys 350.

Figure 3C:
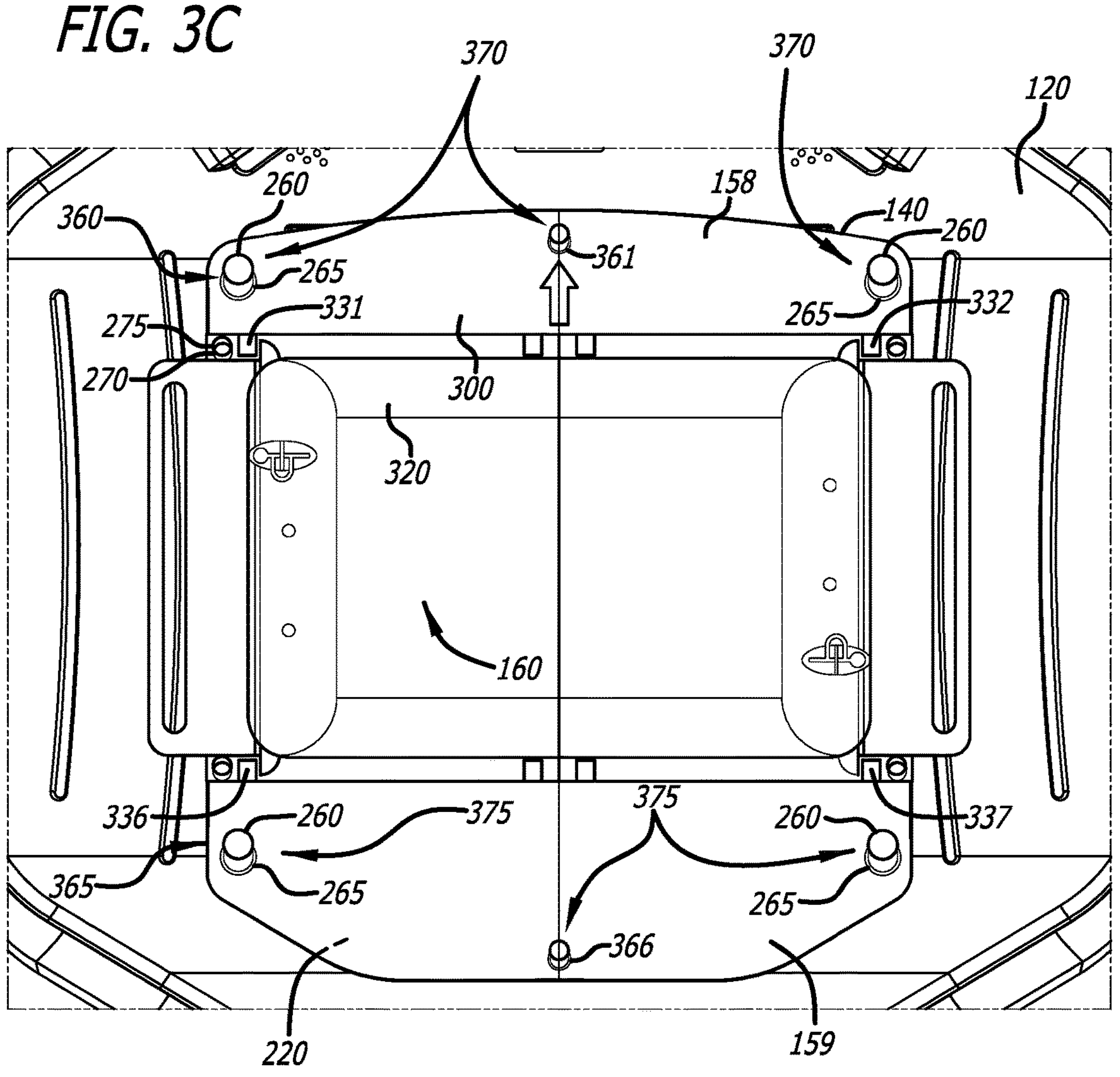
FIG. 3C is a cut-way view of an exemplary embodiment of support apertures implemented within the posterior panel of FIG. 2A.

Referring to FIG. 3C, a cut-way view of an exemplary embodiment of support apertures 265 implemented within the posterior panel 120 of FIG. 2A is shown. Herein, as shown in FIGS. 3B-3C, the plurality of support apertures 265 are positioned to correspond to the plurality of posts 260 extending from the front surface 220 of the posterior cover 140. As shown, a first set of support apertures 360 are positioned to engage with a first set of posts 370 extending from a top cover region 158 of the posterior cover 140. Additionally, a second set of support apertures 365 are positioned to engage with a second set of posts 375 extending from a bottom cover region 159 of the posterior cover 140. According to one embodiment, except for an optional central support aperture 361, a remainder of the first set of support apertures 360 may be coplanar. Similarly, except for a central support aperture 366, a remainder of the second set of support apertures 365 may be coplanar. Support apertures 275 for engagement with posts 270 associated with the pulley cover 160 (see FIG. 2A) may be positioned along the first guide member 300 and the second guide member 320 in closer proximity to the pulley stops 331-332 and 336-337 than the support apertures 265.

Figure 3D:
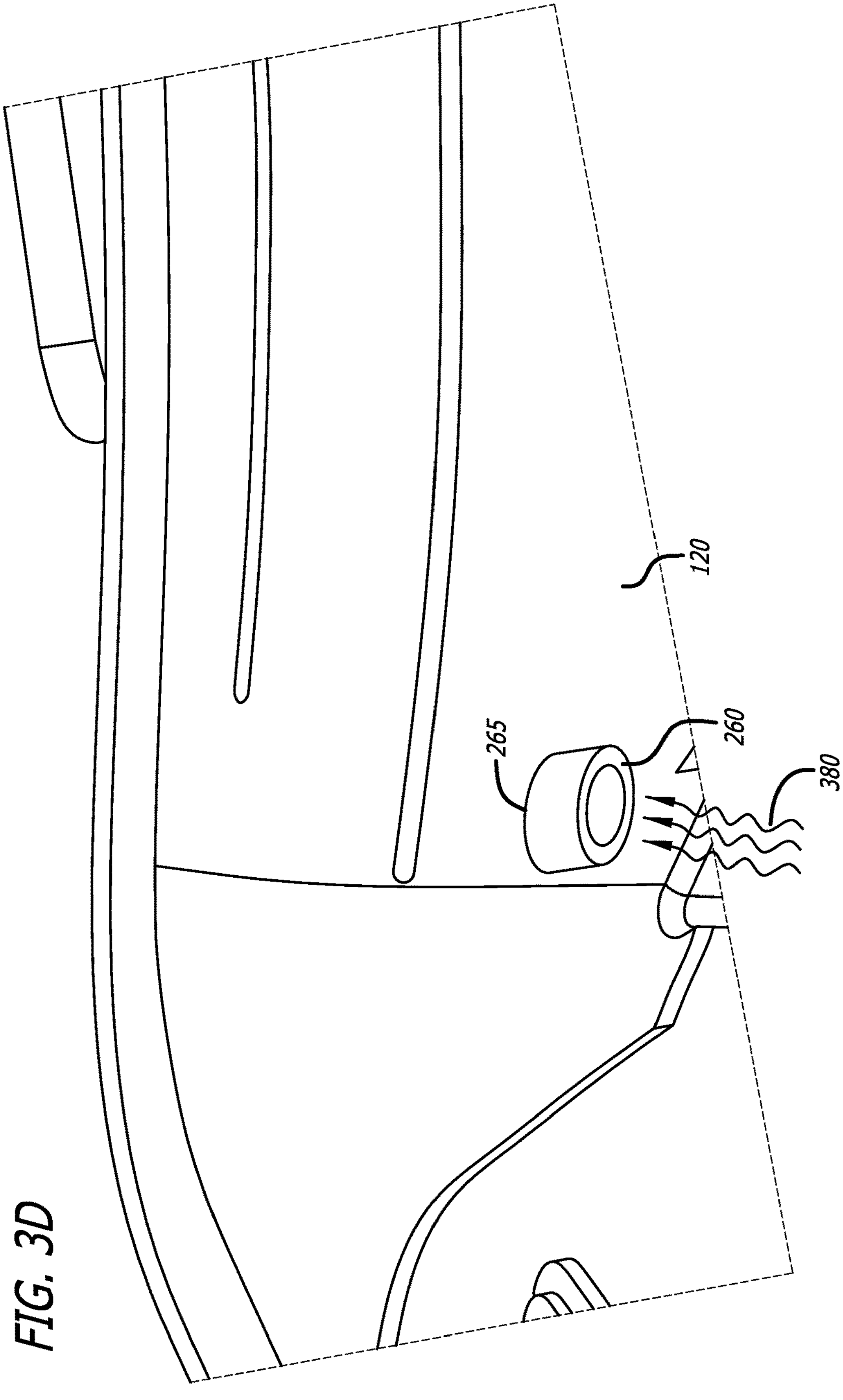
FIG. 3D is a perspective view of an exemplary embodiment of a heat staking process, where a post and support aperture operate as a coupling point between the posterior panel and the posterior cover of FIG. 2A.

Referring to FIG. 3D, a perspective view of an exemplary embodiment of a heat skating process is shown, where the post 260 and support aperture 265 operate as a coupling point between the posterior panel 120 and the posterior cover 140 as well as a reinforcement member. According to this embodiment of the disclosure, the post 260 of the posterior cover 140 may be inserted into a corresponding support aperture 265 formed within the posterior panel 120 and coupled together. For example, the post 260 and the support aperture 265 may be coupled together through a heat staking process. In particular, after insertion of the post 260 within the support aperture 265, a prescribed amount of heat is applied to the post 260. This heat causes the material associated with the post 260 to slightly melt to form a head portion (dome) with a diameter greater that the aperture so that, upon cooling, the post 260 cannot be removed from the support aperture 265 without disfigurement or elimination of the head portion.

Referring to FIG. 4A, a top-down planar view of the posterior bracing system 110, featuring the telescopic lateral panel 210 deployed between the first chamber 280 formed between the posterior panel 120 and the posterior cover 140, is shown. According to one embodiment of the disclosure, the telescopic lateral panel 210 includes a main panel region 400 and a retention panel region 410. As shown, the main panel region 400 corresponds to the portion of the lateral panel 210 that may be removed from the first chamber 280, namely an enclosure formed between the rear surface 205 of the posterior panel 120 and the front surface 220 of the posterior cover 140. The amount of the main panel region 400 removed from the first chamber 280 is dependent on a size (large (L), medium (M), small (S), or variations thereof such as XL, 2XL, XS, etc.) selected for the belt strap member 240 attached to the lateral panel 210 as illustrated in FIGS. 6A-6E.

According to one embodiment of the disclosure, the main panel region 400 of the telescopic lateral panel 210 may include a buckle attachment aperture 425 that is sized to receive a buckle associated with a support strap (not shown) positioned under an axilla of the wearer. When the support strap is inserted therethrough, the buckle attachment aperture 425 features a buckle retention appendage 426, which is flexible and applies a force against an inserted buckle to retain the buckle at least partially within the buckle attachment aperture 425. As a result, the buckle attachment aperture 425 assists in retention of the buckle and its support strap to remain under and away from the axilla of the wearer. This avoids unwanted movement of the strap when the orthopedic brace 100 is worn.

As further shown in FIGS. 4A-4B, the retention panel region 410 corresponds to a minimum portion of the lateral panel 210 that is configured to always remain within the first chamber 280. According to this embodiment of the disclosure, the retention panel region 410 includes a first tab portion 420 extending from its edge 430. The first tab portion 420 (and the lateral panel 210) is positioned to engage with the post 260 of the posterior cover 140, operating as a "stop" for the lateral panel 210, when the lateral panel 210 has been extended to a size in which the main panel region 400 is fully removed from the first chamber 280. The first tab portion 420 prevents the lateral panel 210 from being accidentally removed from the first chamber 280 upon engaging with the post 260. Besides the first tab portion 420, as shown in FIG. 4A. A second tab portion 440 may be positioned to extend from an edge 450 of the retention panel region 410 and engage with another post 260 of the posterior cover 140 when the main panel region 400 is fully removed from the first chamber 280.

Figure 4C:
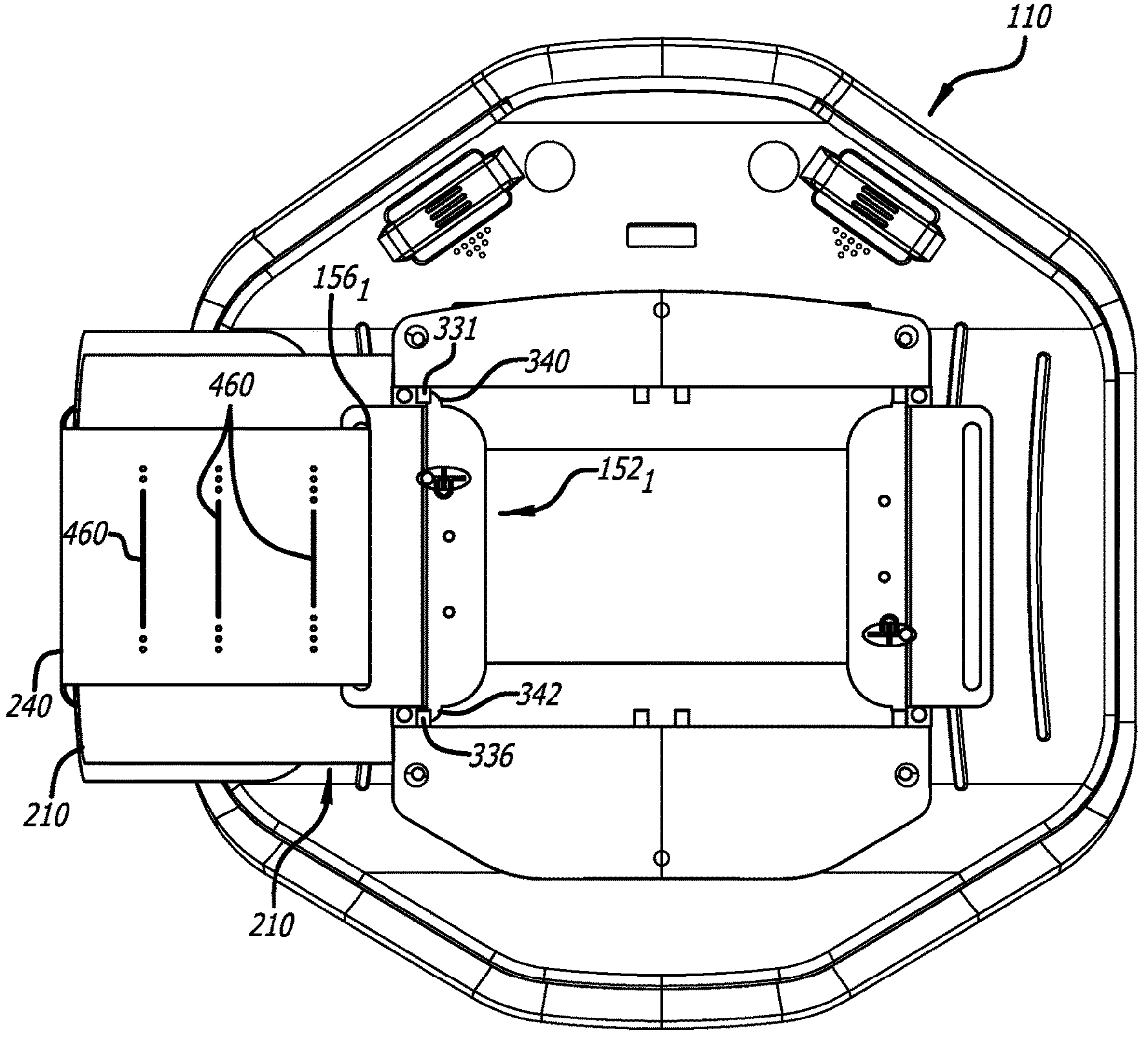
FIG. 4C is a top-down planar view of the posterior bracing system, featuring the telescopic lateral panel operating with the adjustable belt member.

Referring now to FIG. 4C, a top-down planar view of the posterior bracing system 110, featuring the telescopic lateral panel 210 operating with the adjustable belt member 240, is shown. Herein, the belt member 240 is attached to the pulley base 152$_1$ via the belt slot 156$_1$. The belt member 240 may be sized based on indicia 460 placed on the belt member 240 being aligned with a portion of the pulley base 152$_1$, such as a belt slot 156$_1$. Herein, however, the belt member 240 has been sized to a maximum length as denoted by the first and second flanges 340 and 342 are engaging pulley stops 331 and 336. The lateral panel 210 and belt member 240 are coupled together and moved laterally and anteriorly for coupling with an anterior bracing system as shown in FIG. 20K).

Figure 5A:
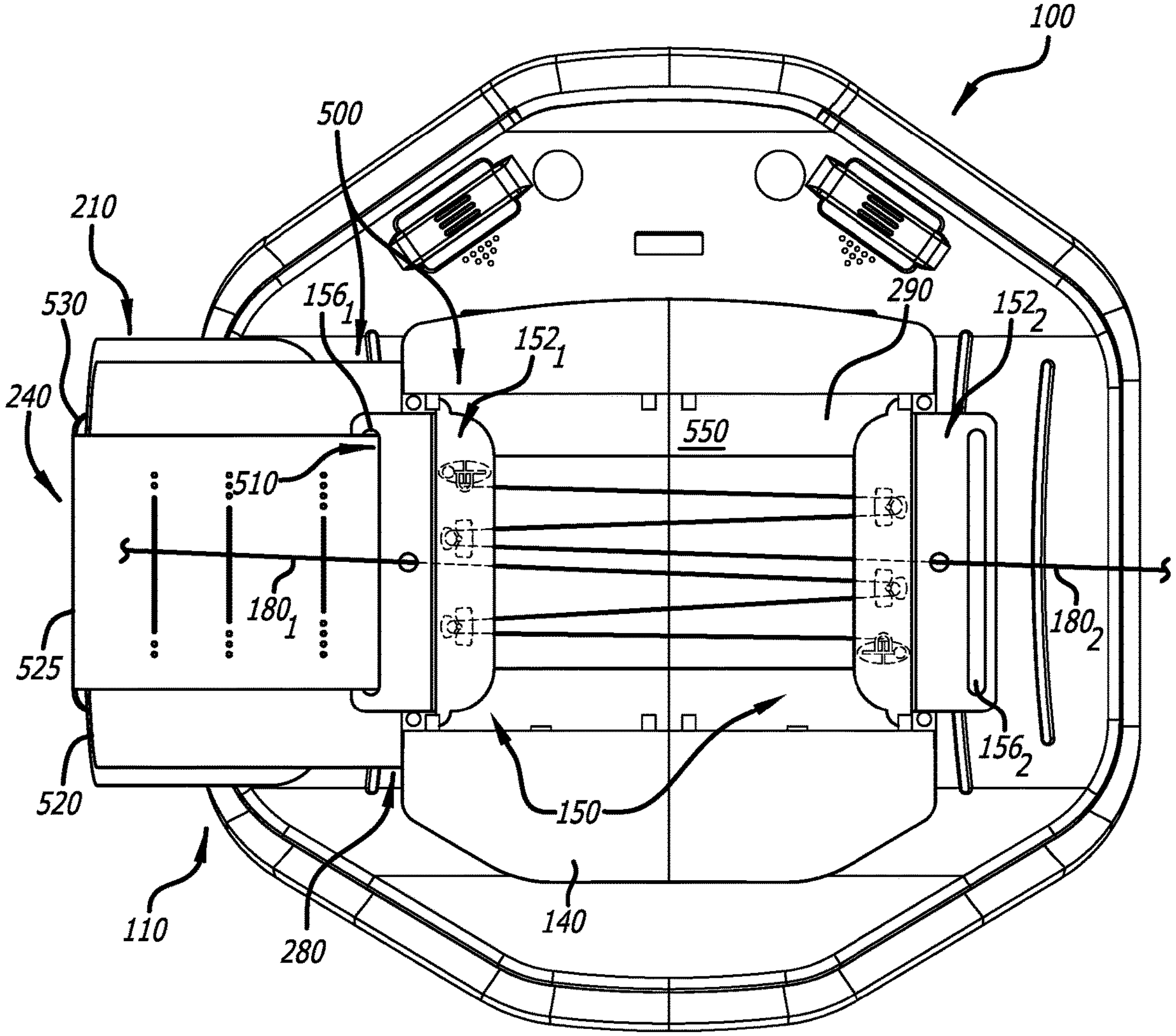
FIG. 5A is an exemplary embodiment of an orthosis fastening subsystem deployed within the orthopedic brace of FIG. 1.

Referring now to FIG. 5A, an exemplary embodiment of an orthosis fastening subsystem 500 deployed within the orthopedic brace 100 is shown. Implemented as components of the posterior bracing system 110, the orthosis fastening subsystem 500 features the pulley subsystem 150, the telescopic lateral panels 210 (e.g., a first lateral panel 520 as shown), and the belt members 240 (e.g., a first belt member 525 as shown), which operate together for sizing and attachment of the orthopedic brace 100 to a patient. The first telescopic lateral panel 520 slidably extends from the first chamber 280 formed under the posterior cover 140 in a direction opposite to a direction of extension of a second telescopic lateral panel (not shown). Additionally, a first end 510 of the first belt member 525 is anchored to the belt slot 156$_1$ of the first pulley base 152$_1$ while a first end of the second belt member (not shown) would be anchored to the belt slot 156$_2$ of the second pulley base 152$_2$.

Figure 5B:
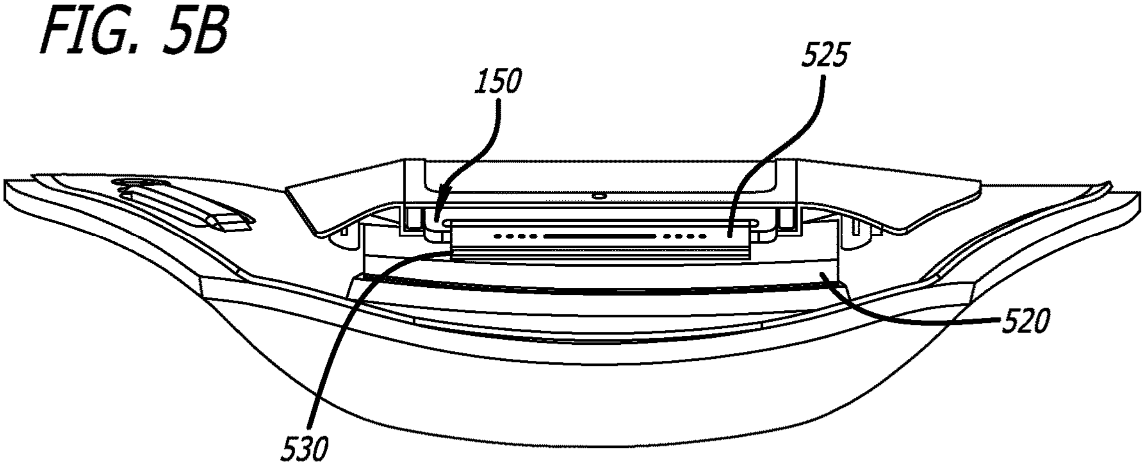
FIG. 5B is a side view of an exemplary embodiment of posterior bracing system featuring the pulley subsystem of FIG. 5A.

As further shown in FIGS. 5A-5B, the pulley subsystem 150 includes the first pulley base 152$_1$ and the second pulley base 152$_2$ coupled together through the pulley cords 180$_1$ and 180$_2$. Although not shown, the pulleys mounted under the pulley bases 152$_1$-152$_2$ apply tension and cause inward movement (toward a central area 550 of the second chamber 290) of (i) the first belt member 525 when the pulley cord 180$_2$ is pulled away in an anterior and/or lateral direction and (ii) the second belt member (not shown) when the pulley cord 180$_1$ is pulled away in an anterior and/or lateral direction. Additionally, given that a portion of the first belt member 525, proximate to a second end 530 of the first belt member 525 is attached to the first lateral panel 520 as shown in FIG. 5B, such as through complementary loop and hook fasteners for example, inward movement of the first belt member 525 causes complementary interior movement of the first lateral panel 520 and vice versa. The same adjustment scheme would be applicable to the second lateral panel (not shown). This enables easier donning of the orthopedic brace without log-rolling the patient for customized re-fitting of the posterior lateral panels.

Figure 5C:
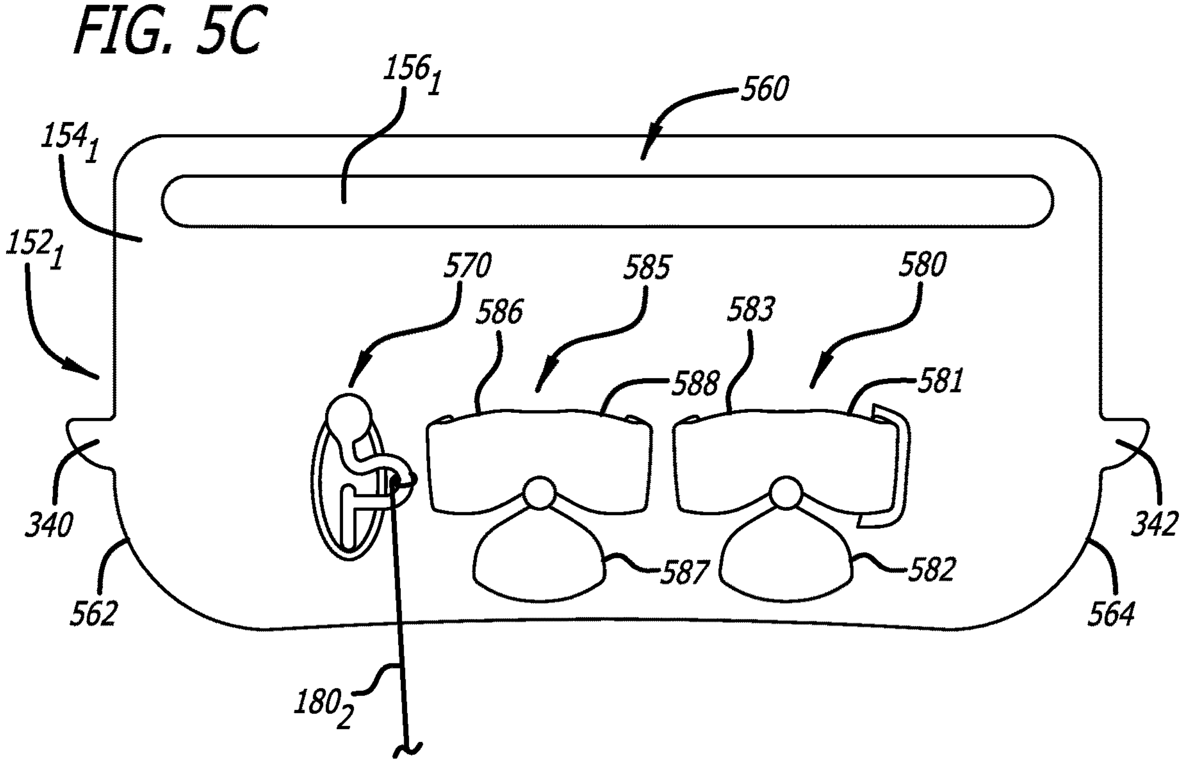
FIG. 5C is a top-down planar view of an exemplary embodiment of the pulley base of FIG. 5A.

Referring to FIG. 5C, a top-down planar view of an exemplary embodiment of a pulley base (e.g., pulley base 152$_1$) of FIG. 5A is shown. Herein, the pulley base 152$_1$ includes the base member 154$_1$ featuring (i) the belt slot 156$_1$ positioned proximate to a first outer lateral edge 560 of the base member 154$_1$, (ii) the first flange 340 positioned on a second outer lateral edge 562 of the base member 154$_1$, and (iii) the second flange 342 positioned on a third outer lateral edge 564 of the base member 154$_1$. Herein, both the second and third outer lateral edges 562 and 564 are generally orthogonal to first outer lateral edge 560. The second and third outer lateral edges 562 and 564 are positioned on opposite sides of the base member 154$_1$.

Mounted on the base member 154$_1$, a first pulley cord attachment member 570 is configured to securely attach an end 182 of the second pulley cord 180$_2$ to the pulley base 152$_1$. The second pulley cord 180$_2$ is provided from the first pulley cord attachment member 570 to the second pulley base 152$_2$ as shown in FIG. 5A. Further mounted on the base member 154$_1$, a first pulley 580 is configured to receive the second pulley cord 180$_2$ from a pulley mounted on the second pulley base 152$_2$, where the second pulley cord 180$_2$ is threaded through an input port 581, wound around a first pulley wheel 582, and threaded through an output port 583 towards cord passage apertures 170$_2$. A second pulley 585 is configured to receive the first pulley cord 180$_1$ from the second pulley base 152$_2$, where the first pulley cord 180$_1$ is threaded through an input port 586, wound around a second pulley wheel 587, and threaded through an output port 588 for return to another pulley of the second pulley base 152$_2$.

Figure 5D:
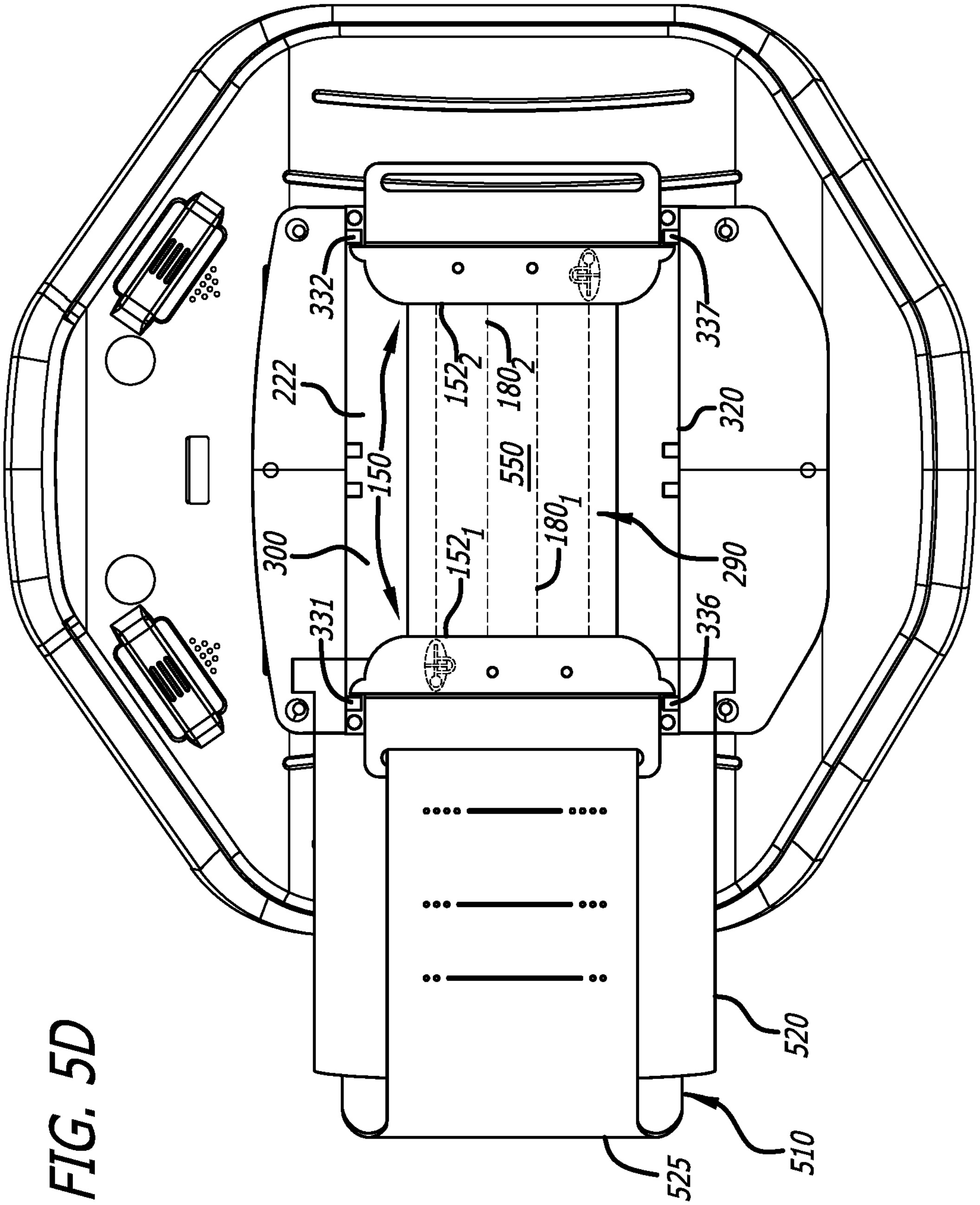
FIG. 5D is a top-down planar view of an exemplary embodiment of the pulley subsystem operating in a first state.
Figure 5E:
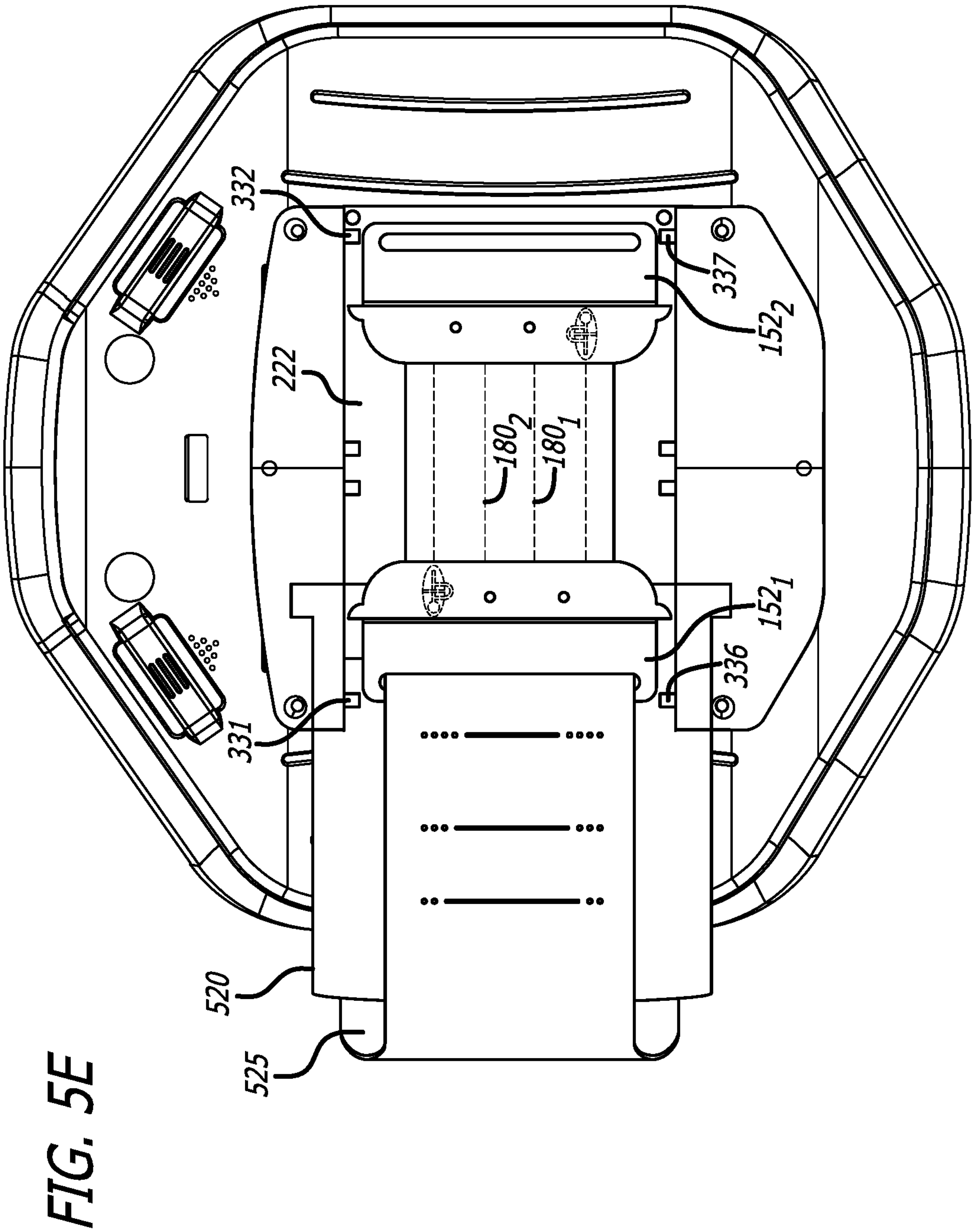
FIG. 5E is a top-down planar view of an exemplary embodiment of the pulley subsystem operating in a second state in response to a tightening operation in which the telescopic lateral panel and the belt member partially return into the first and second chambers.

As shown in FIG. 5D, after setting of the sizing of the belt members 240 and attachment to the lateral panels 210, the pulley bases 152$_1$-152$_2$ of the pulley subsystem 150 are positioned in a first state. In the first state, the pulley bases 152$_1$-152$_2$ may be located closer to the pulley stops 331-332 and 336-337 than the central area 550 of the second chamber 290. In response to tightening of pulley cord(s) 180$_1$ and/or 180$_2$, as shown in FIG. 5E, the pulley bases 152$_1$-152$_2$ traverse along the guide channel 222, in particular the first and third guide members 300 and 320, towards the central area 550 of the second chamber 290. The pulley bases 152$_1$-152$_2$ are non-stationary as these pulley bases 152$_1$ and 152$_2$ push their corresponding lateral panel/belt member combinations outwardly from the first and second chambers during initial sizing as well as pull their corresponding lateral panel/belt member combinations into the first and second chambers 280 and 290 during tightening. For example, the pulley base 152$_1$ is configured to push its corresponding lateral panel/belt member combinations 520/525 outwardly from the first and second chambers during initial sizing as well as pull the corresponding lateral panel/belt member combinations 520/525 into the first and second chambers 280 and 290 during tightening Referring now to FIG. 6A-6B, exemplary embodiments of an internal sizing of a second belt member 600 (e.g., opposite to belt member 525 of FIG. 5A) is shown, with subsequent sizing of the telescopic lateral panel 620 (e.g., opposite to lateral panel 520 of FIG. 5A). Herein, the second belt member 540 includes a first set of indicia 610 that identifies different belt sizes (large, medium, small, etc.) when oriented with a selected portion of the pulley base 152$_2$. For example, as an illustrated embodiment, the indicia 610 may include a plurality of indicia elements 615 each corresponding to a different belt size so that the second belt member 600 is sized accordingly. More specifically, a selected indicia element 612 may be oriented with a selected portion of the pulley base $152_2$ (e.g., within the belt slot $156_2$ of the pulley base $152_2$), and thereafter, a first fastener 625 (e.g., loop and hook fastener) at a first end 622 of the second belt member 600 is coupled to a second fastener 626 (e.g., complementary loop and hook fastener) located along an interior surface 628 of the second belt member 600 so as to wrap the second belt member 600 around the belt slot $156_2$ and the point of connection facing inward. As a result, the second belt member 600 is placed in a size corresponding to the selected indicia element 612.

Figure 6A:
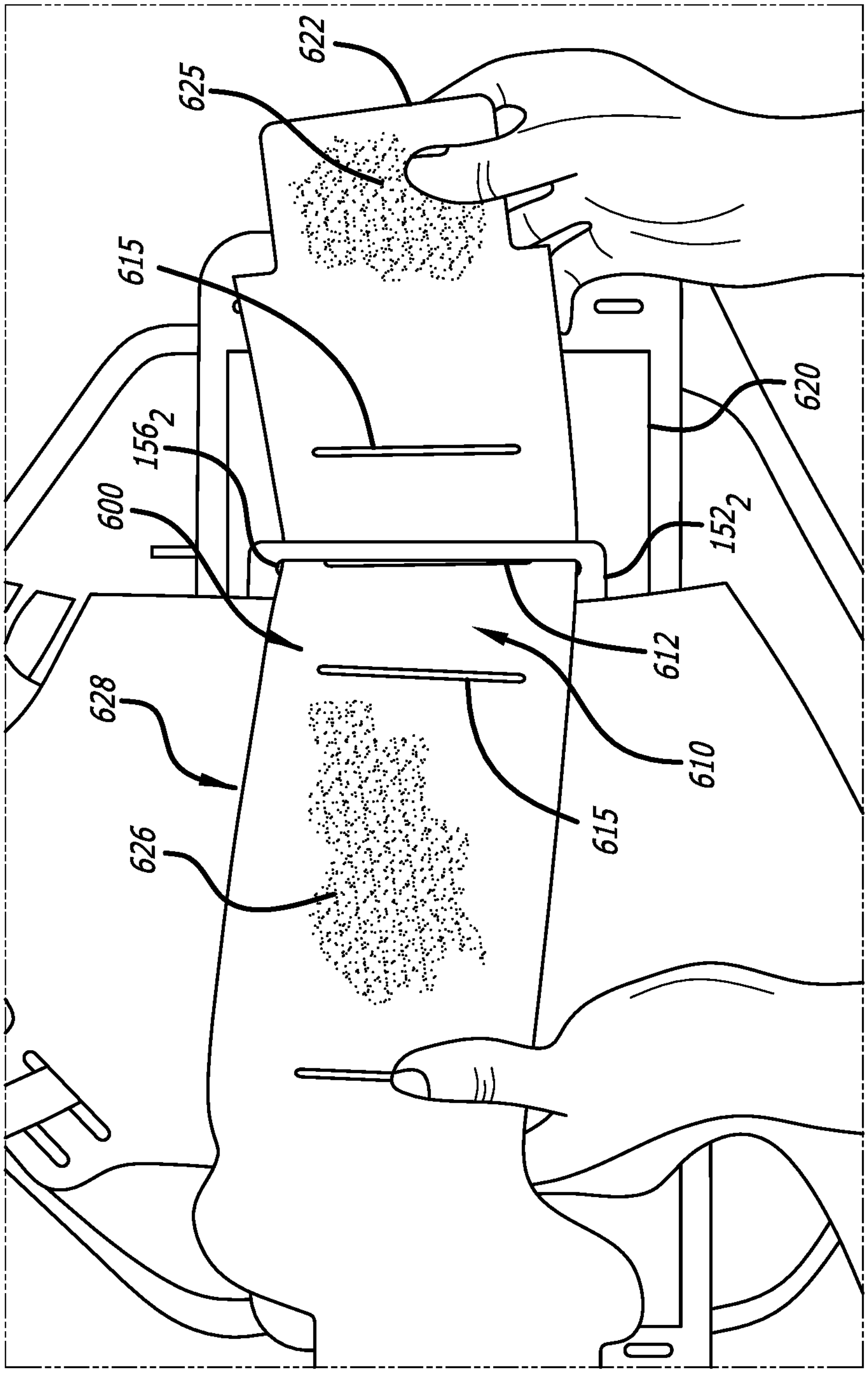
FIG. 6A-6B are exemplary embodiments of an internal sizing of the belt and subsequent sizing of the telescopic lateral panel deployed within the posterior bracing system of FIG. 2A.
Figure 6B:
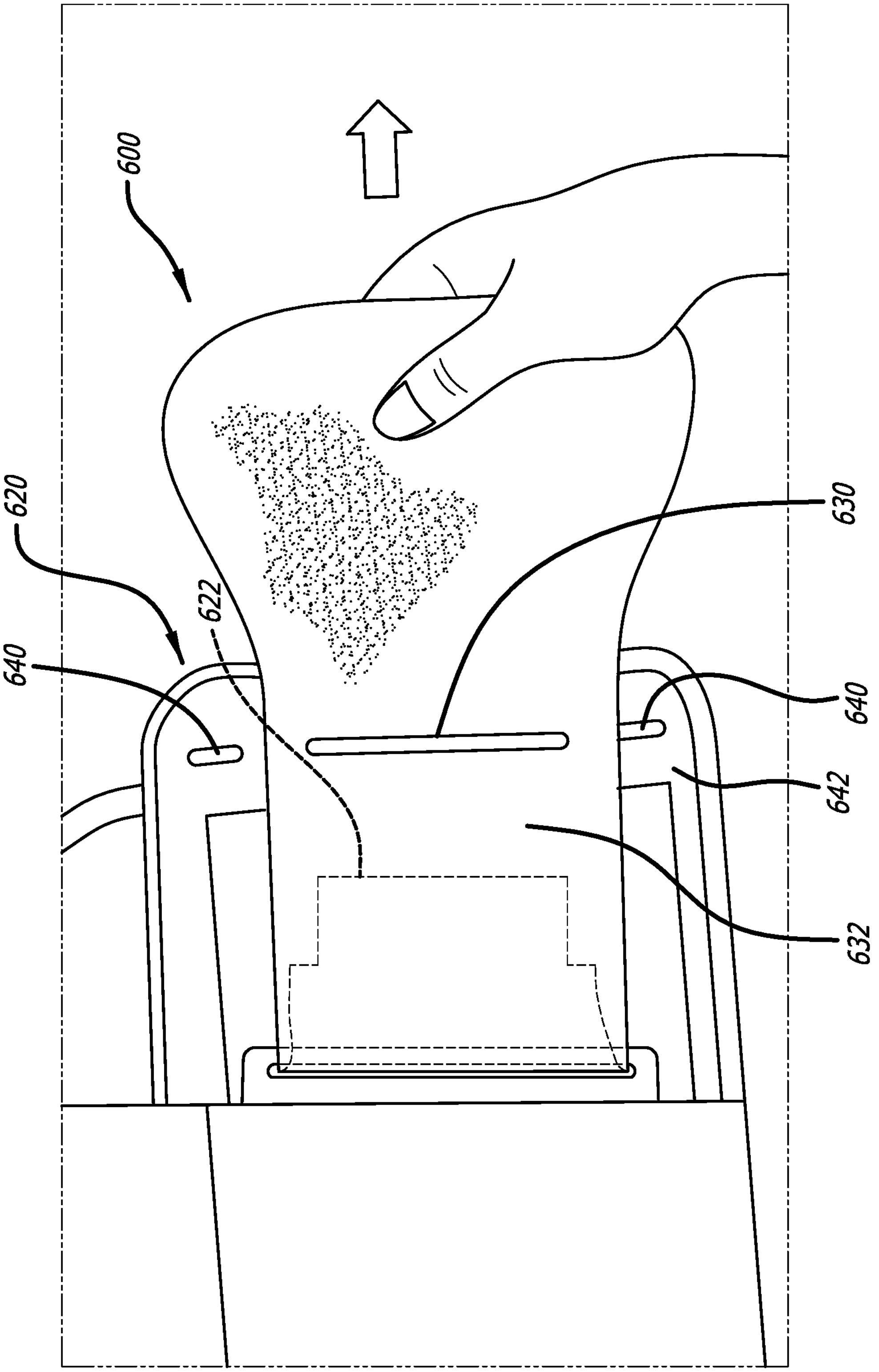

After the second belt member 600 has been sized, as shown in FIG. 6B, indicia 630 located on its exterior surface 632 is aligned with indicia 640 located on a rear-facing surface 642 of the telescopic lateral panel 620 so that the telescopic lateral panel 620 is set to an identical size. Hence, the second belt member 600 restricts side extension of the telescopic lateral panel 620 to comfort with the sizing of the second belt member 600. It is contemplated that an exteriorly-sized belt 600 may be semi-permanently attached to the lateral panel 620 so that we can reduce sizing needs by the orthotist. As a result, the orthotist or clinician would not need to align the belt to the indicia 640 on the lateral panel 620.

Figure 6C:
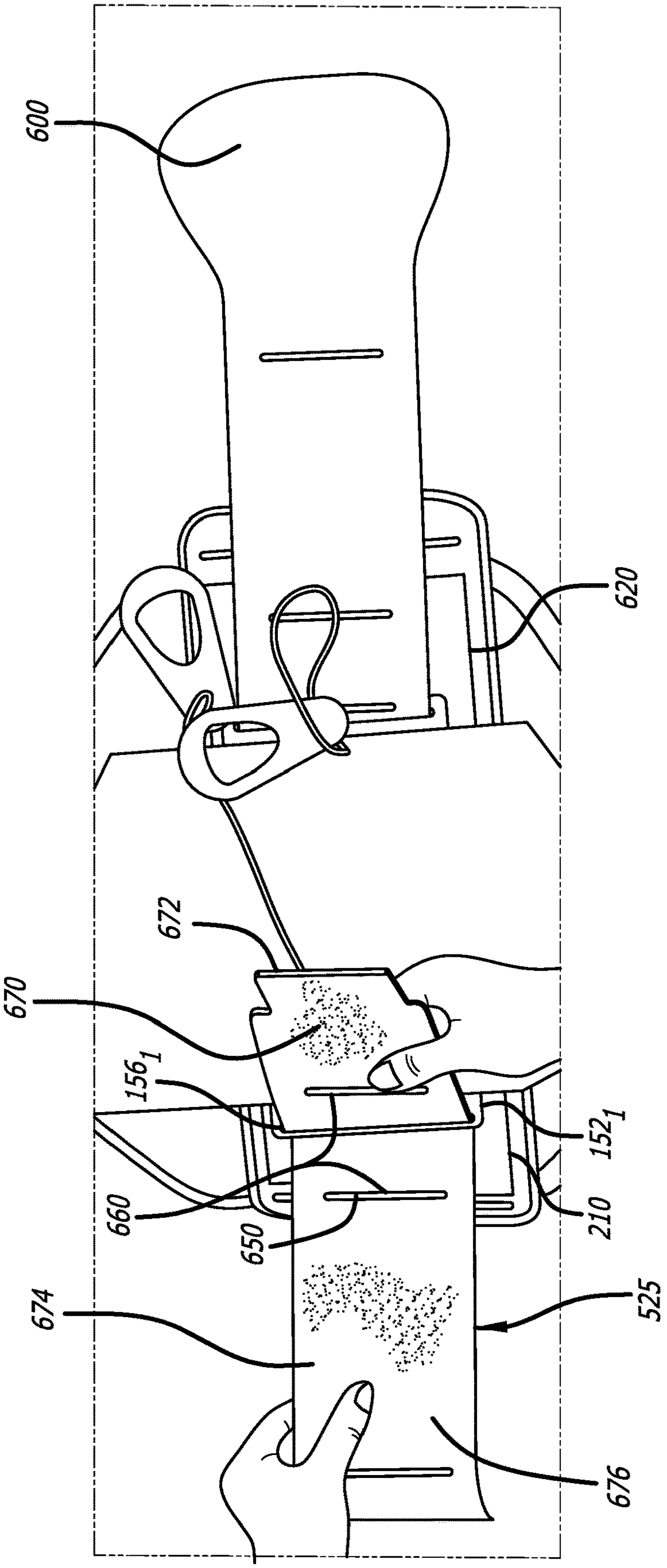
FIG. 6C-6D are exemplary embodiments of an external sizing of the belt and subsequent sizing of the telescopic lateral panel deployed within the posterior bracing system of FIG. 2A.
Figure 6D:
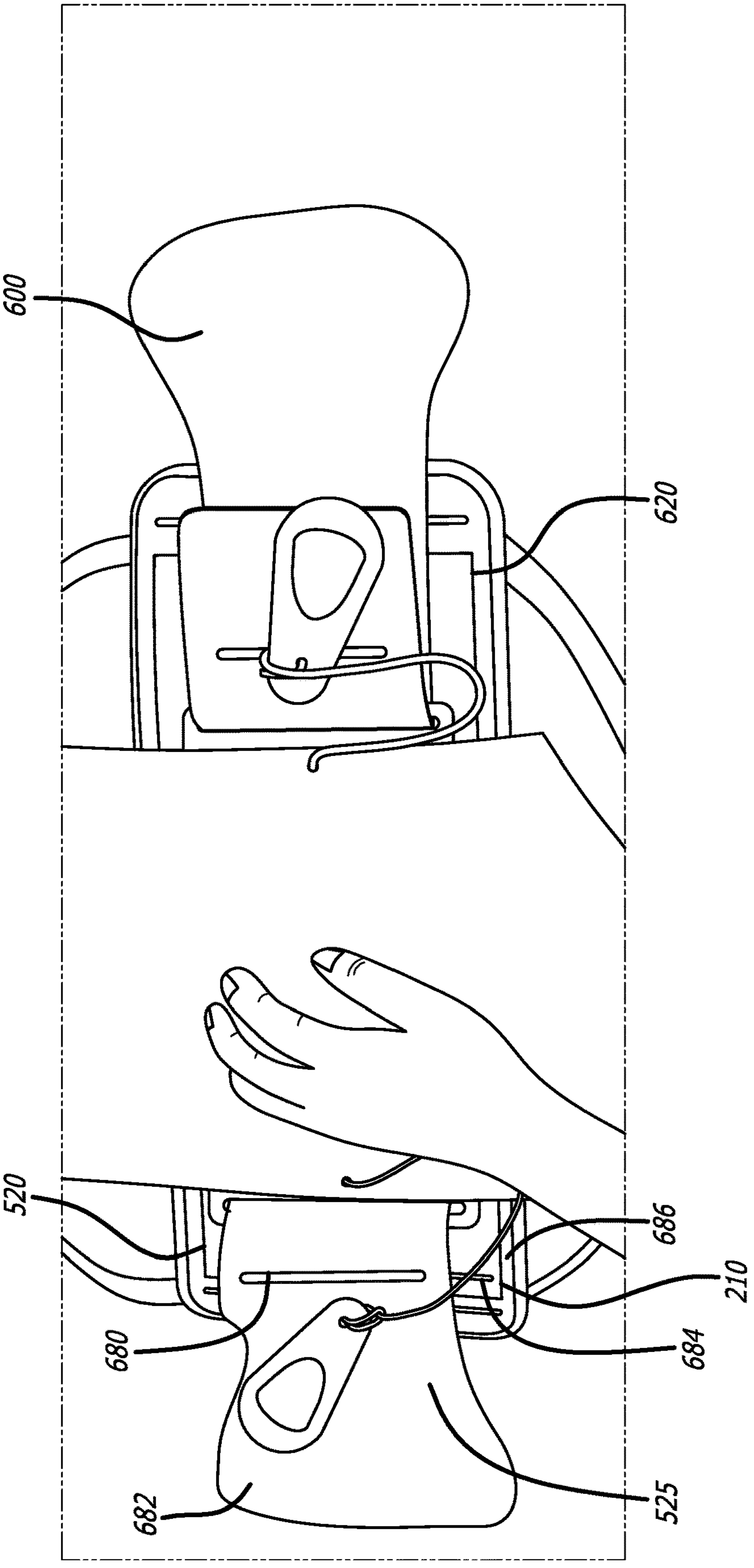

Referring to FIG. 6C-6D, exemplary embodiments of an external sizing of a belt member (e.g., the first belt member 525 of FIG. 5A) is shown, with subsequent sizing of the telescopic lateral panel 520. Herein, the first belt member 525 includes a first set of indicia 650 that identifies different belt sizes (large, medium, small, etc.) when oriented with a selected portion of the pulley base $152_1$. For example, as an illustrated embodiment and similar to the internal sizing of a belt member shown in FIGS. 6A-6B, the indicia 650 may include a plurality of indicia elements 660 each corresponding to a different belt size so that the first belt member 530 is sized accordingly. More specifically, a selected indicia element may be oriented with a selected portion of the pulley base $152_2$ (e.g., within the belt slot $156_1$ of the pulley base $152_1$), and thereafter, a first fastener 670 (e.g., loop and hook fastener) at a first end 672 of the first belt member 525 is coupled to a second fastener 674 (e.g., complementary loop and hook fastener) located along an outer surface 676 of the first belt member 525 so as to wrap the first belt member 525 around the belt slot $156_1$ and the point of connection facing outward. As a result, the first belt member 525 is placed in a size corresponding to the selected indicia element.

After the first belt member 525 has been sized, as shown in FIG. 6D, indicia 680 located on its exterior surface 682 is aligned with indicia 684 located on a rear-facing surface 686 of the telescopic lateral panel 520 so that the telescopic lateral panel 520 is set to an identical size. Hence, the first belt member 525 restricts side extension of the telescopic lateral panel 520 to comfort with the sizing of the first belt member 525.

Figure 6E:
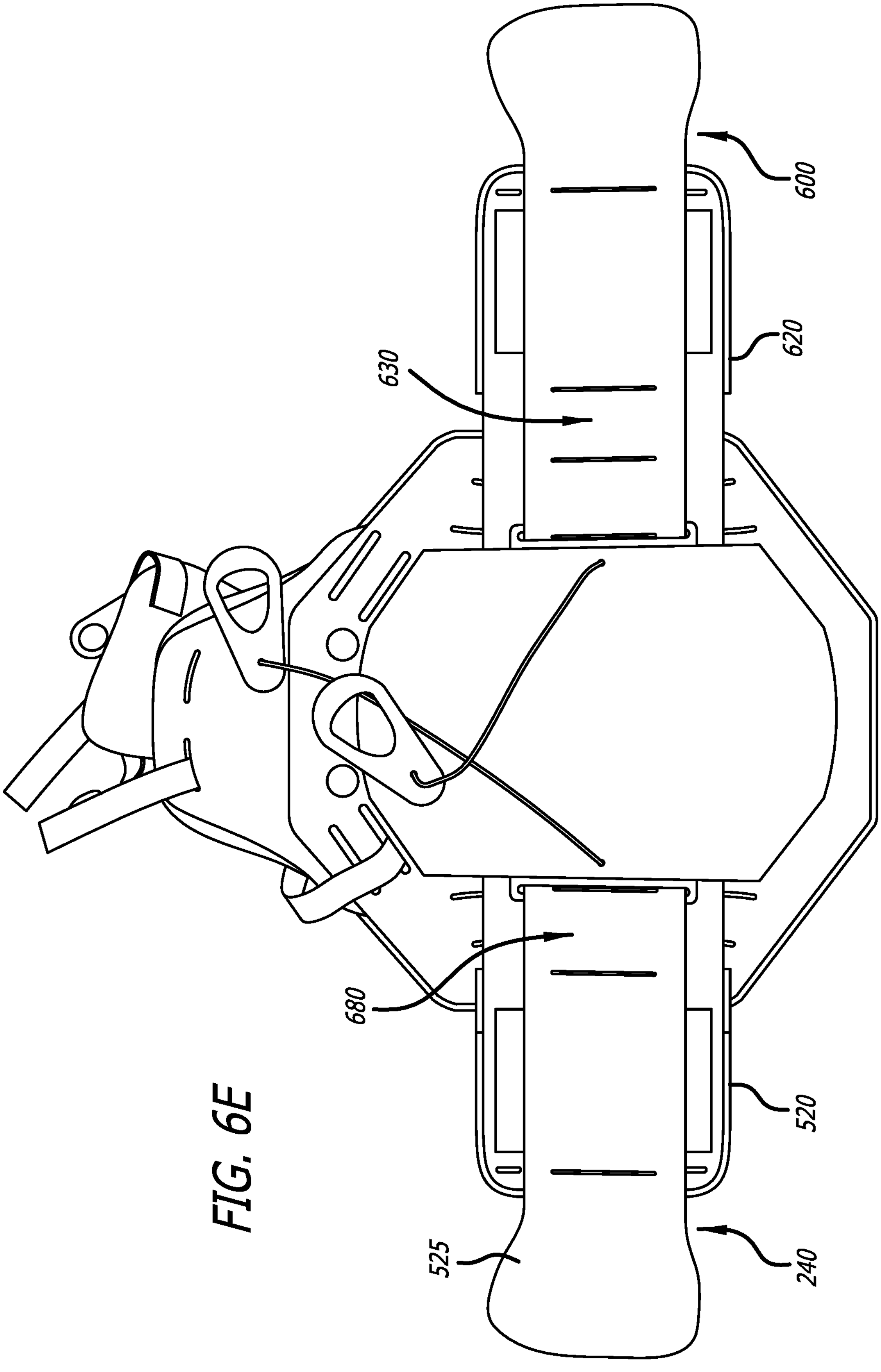
FIG. 6E is an exemplary embodiment of the orthosis fastening system being adjusted to illustrate different lateral panel and belt member combinations with different size settings conducted in accordance with different belt sizing processes as illustrated in FIGS. 6A-6D.

As a result, as shown in FIG. 6E as an illustrative example, the first belt member 525 has been sized in accordance with an external sizing process into a "medium" sizing. The second belt member 600 has been sized in accordance with an internal sizing process into a "large" sizing. The indicia 680 on the first belt member 525 is aligned with slots (or indicia) on the first telescopic lateral panel 520. The indicia 630 on the second belt member 600 is aligned with slots (or indicia) on the second telescopic lateral panel 620. As a result, both lateral panels 520 and 620 are sized consistent with their corresponding belt members 525 and 600, and thus, the second telescopic lateral panel 620 (sized to large) extends further outside the first chamber than the first telescopic lateral panel 520 (sized to medium).

Figure 7A:
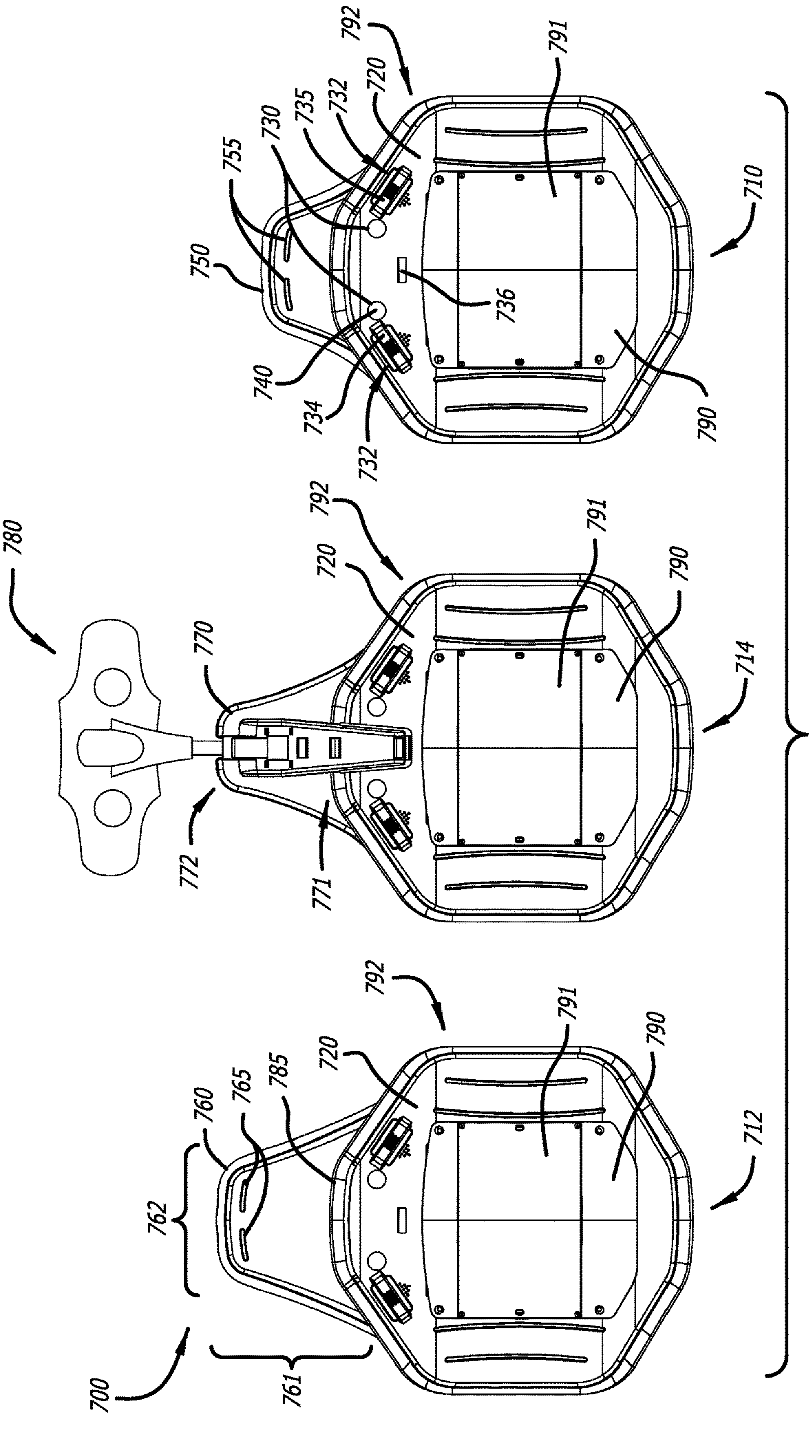
FIG. 7A is a perspective rear view of an exemplary embodiment of a first group of posterior bracing systems, each including a first type of posterior panel and different types of extension panels.

Referring to FIG. 7A, perspective rear views of exemplary embodiments of a first group of posterior bracing systems 700 is shown, where each of the posterior bracing systems 700 features a first type of posterior panel and a different type of extension panel. More specifically, for illustrative purposes, the first group of posterior bracing systems 700 includes a first posterior bracing system 710, a second posterior bracing system 712, and a third posterior bracing system 714. Each of these posterior bracing systems 710, 712 and 714 includes a first type of posterior panel 720 (equivalent to posterior panel 120 of FIG. 1) that is generally octagonal in shape with a first prescribed length and width so that the first posterior panel 720, when placed on a patient, rests against and supports the thoracic and lumbar regions of the patient's spine.

According to one embodiment of the disclosure, the first posterior panel 720 includes a plurality of locking slots 730, a plurality of strap guides 732 (e.g., a first strap guide 734 and a second strap guide 735), and a stabilization slot 736. More specifically, the first posterior panel 720 may include (i) the pair of locking slots 730, which are sized to receive locking protrusions 740 formed within each extension panel 750, 760, 770 and (ii) the strap guides 732 for retention of attachment straps (not shown). The strap guides 732 are positioned to align with strap slots implemented at specific locations on each of the extension panels to allow a strap to pass through the extension panel 750 before looped around and secured at a corresponding strap guide 732. As described below, the stabilization slot 736 is sized to receive a stabilization component on the third (cervical) extension panel 770, and otherwise, remains unused by the first or second extension panels 750 and 760.

As further shown and described below, the first posterior panel 720 may be adapted with the first extension panel 750, the second extension panel 760, or the third extension panel 770. The first and second extension panels 750 and 760 are attached to the first posterior panel 720 to operate as a TLSO in which the extension panels 750/160 provide additional support for the upper back and neck regions, while allowing the patient's head to move freely even after the orthopedic brace is donned by the patient. The differences between the first extension panel 750 and the second extension panel 760 is directed to the size of the patient. The first extension panel 750 is a standard size for patients while the second extension panel 760 is longer in length 761 (and narrower in width 762 in some cases) to account for taller patients. However, the third extension panel 770 may be attached to the first posterior panel 720 to operate as a CTLSO in which the third extension panel 770 is attached to a rear portion of a cervical collar 780 to isolate movement of the patient's head after donning. At its lower region 771, the third extension panel 770 has a substantially similar width as the first and second extension panels 750 and 760. At its upper region 772, the third extension panel 770 is narrower than the first and second extension panels 750 and 760 besides the CTLSO extension 770 lacks strap slots 755 and 765 positioned at the upper region of these extension panels 750 and 760.

As further shown, the posterior bracing system 710 further features a plurality of structural members layered onto the first posterior panel 720 to create a plurality of chambers therebetween. These structural members may include, but are not limited or restricted to a posterior cover 790 and a pulley cover 791. The posterior cover 790 is coupled to the posterior panel 720 to provide a first protective chamber to house telescopic lateral panels (not shown) extending from the first protective chamber. The pulley cover 791 is coupled to the posterior cover 790 to protect a pulley subsystem (not shown) that resides within a second protective chamber formed between an anterior-facing surface of the pulley cover 791 and a posterior-facing recessed area within the posterior cover 790. The pulley cover 791 is smaller in size (e.g., width and length) than the posterior cover 790 so as to overlay the recessed area of the posterior cover 790 including the pulley subsystem and refrain from covering at least top posterior panel region 792 including the plurality of locking slots 730, the plurality of strap guides 732, and the stabilization slot 736.

Figure 7B:
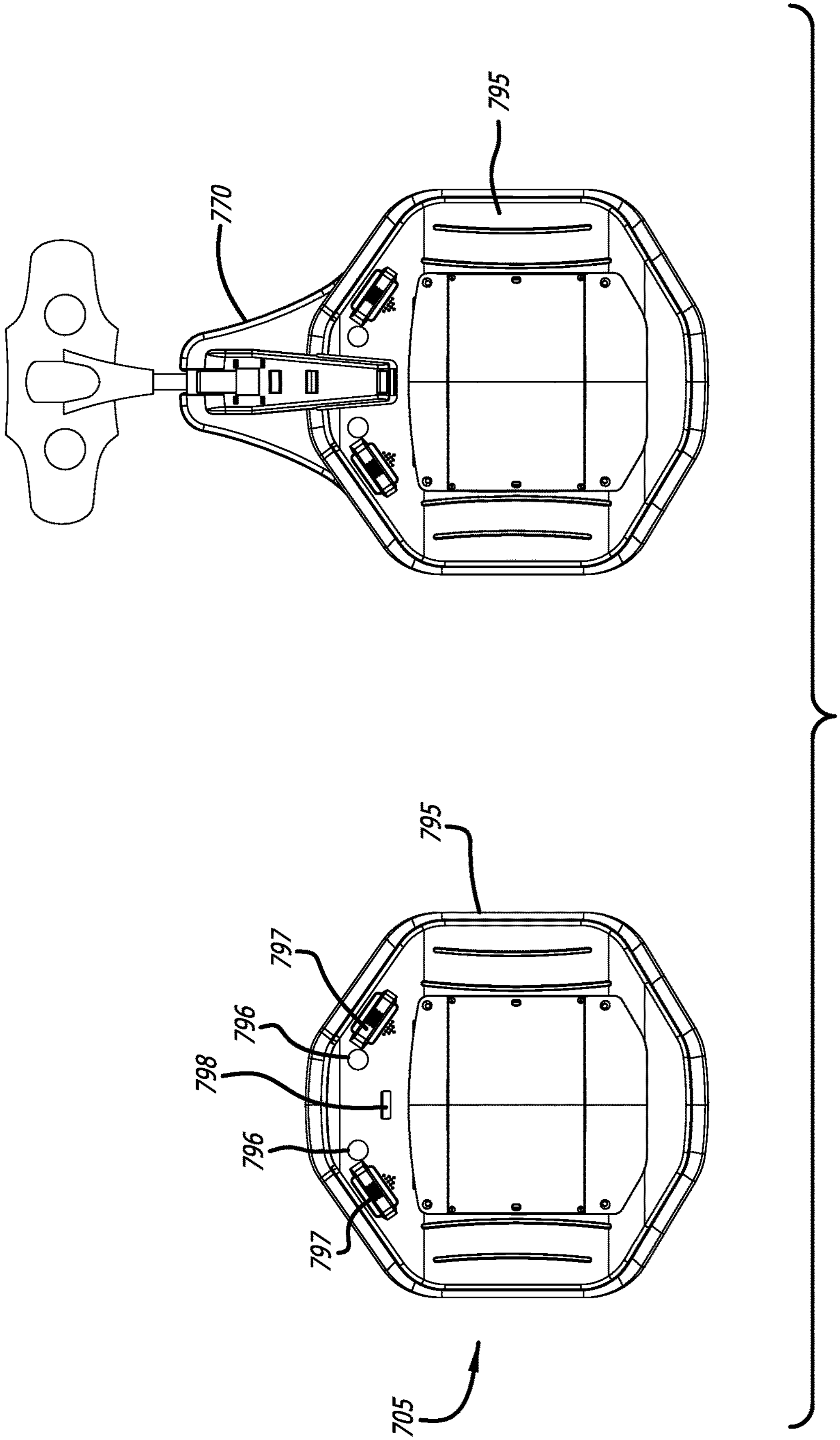
FIG. 7B is a perspective rear view of an exemplary embodiment of a second group of posterior bracing systems, each including a second type of posterior panel and different types of extension panels.

Referring to FIG. 7B, perspective rear views of exemplary embodiments of a second group of posterior bracing systems 705, each including a second type of posterior panel 795 and optionally the third extension panel 770. Similar to the first posterior panel 720, the second posterior panel 795 is generally octagonal in shape, but features a second prescribed length and width less than the first prescribed length and width. Hence, this deployment is directed toward smaller sized patients, and thus, only needs to be adapted for the third extension panel 770 to provide CTLSO functionality. Of course, the second posterior panel 795 is configured with locking slots 796, strap guides 797, and a stabilization slot 798, which are positioned in relation to each other identical to the locking slots 730, the strap guides 732 and the stabilization slot 736 provided by the first type of posterior panel 720. This allows for the extension panels 750 and 760, and the third (cervical) extension panel 770 with an extension rod and rear portion of a cervical collar (as shown), to be interchangeably used between either the first posterior panel 720 or the second posterior panel 795.

Figure 8A:
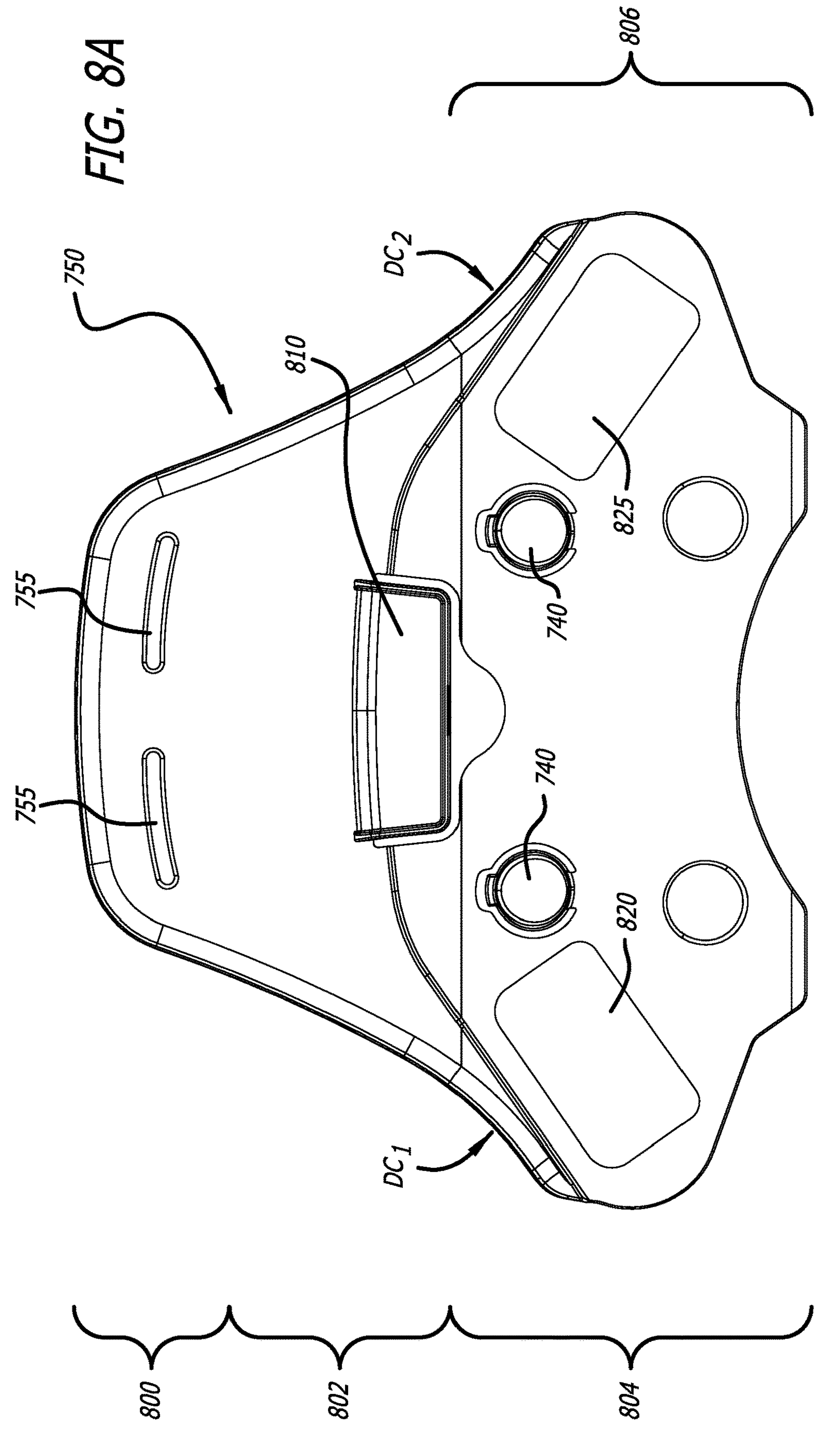
FIG. 8A is a perspective view of a first type of extension panel deployed on a posterior panel as shown in FIG. 7A.

Referring now to FIG. 8A, a perspective view of the first extension panel 750 capable of being deployed on the posterior panel 720/795 of FIGS. 7A-7B is shown. Herein, the first posterior panel 720 is selected as the posterior panel type to illustrate the connectivity with the extension panels 750/760/770. Generally configured with a polygonal shape (e.g., hexagonal configuration), the first extension panel 750 includes an upper region 800, a middle region 802, a left lower region 804 and a right lower region 806. Herein, the upper region 800 of the extension panel features first and second strap slots 755, which are positioned to receive an adjustable strap positioned over a shoulder of a user. The middle region 802 features a fastening clip 810, which is positioned to be securely coupled to a top edge of the posterior panel 720 when the extension panel 750 is secured to the first posterior panel 720. The fastening clip 810 is generally centered between the locking protrusions 740, which may be inserted into the locking slots 730 of a posterior panel (e.g., the first posterior panel 720) as shown in FIG. 7A.

As still shown in FIG. 8A, the left lower region 804 features a third strap slot 820 is positioned in horizontal alignment with the first strap guide 734 of the first posterior panel 720 when the first extension panel 750 is attached to a posterior panel (e.g., first posterior panel 720). The third strap slot 820 is configured with a width greater than a width of any of the first and second strap slots 755, which allows an adjustment strap to pass unencumbered through the first strap guide 734 positioned within the first posterior panel 720, loop around a member extending across the first strap guide 734, and return to an anterior side of the posterior bracing system 710. Similar in orientation, a fourth strap slot 825 is positioned to be in horizontal alignment with the second strap guide 735 when the extension panel 750 is attached to the first posterior panel 720 via the locking slot/protrusion engagement 730/740. A first degree of curvature ($DC_1$) for a first perimeter section extending from the left lower region 804 toward the upper region 800 may be substantially equivalent to a second degree of curvature ($DC_2$) for a second perimeter section extending from the right lower region 806 toward the upper region 800.

Referring now FIG. 8B, a perspective view of the second type of extension panel 760 (hereinafter, "second extension panel 760"), configured to be attached to a posterior panel as illustrated in FIG. 7A, is shown. Similar to the first extension panel 750, the second extension panel 760 is generally configured with a polygonal shape (e.g., hexagonal configuration), including an upper region 830, a middle region 832, a left lower region 834 and a right lower region 836. The upper region 830 of the extension panel features the strap slots 765, namely a first slot 840 and a second strap slots 842 positioned to receive an adjustable strap positioned over a shoulder of a user. The middle region 832 also features the fastening clip 810, which is positioned to be securely coupled to a top perimeter section (edge) 785 of the first posterior panel 720 (see FIG. 7A) when the second extension panel 760 is secured to the first posterior panel 720. The fastening clip 810 may be centered between locking protrusions 846/848, which may be inserted into locking slots of a posterior panel, such as the locking slots 730 of the first posterior panel 720 for example.

Figure 8B:
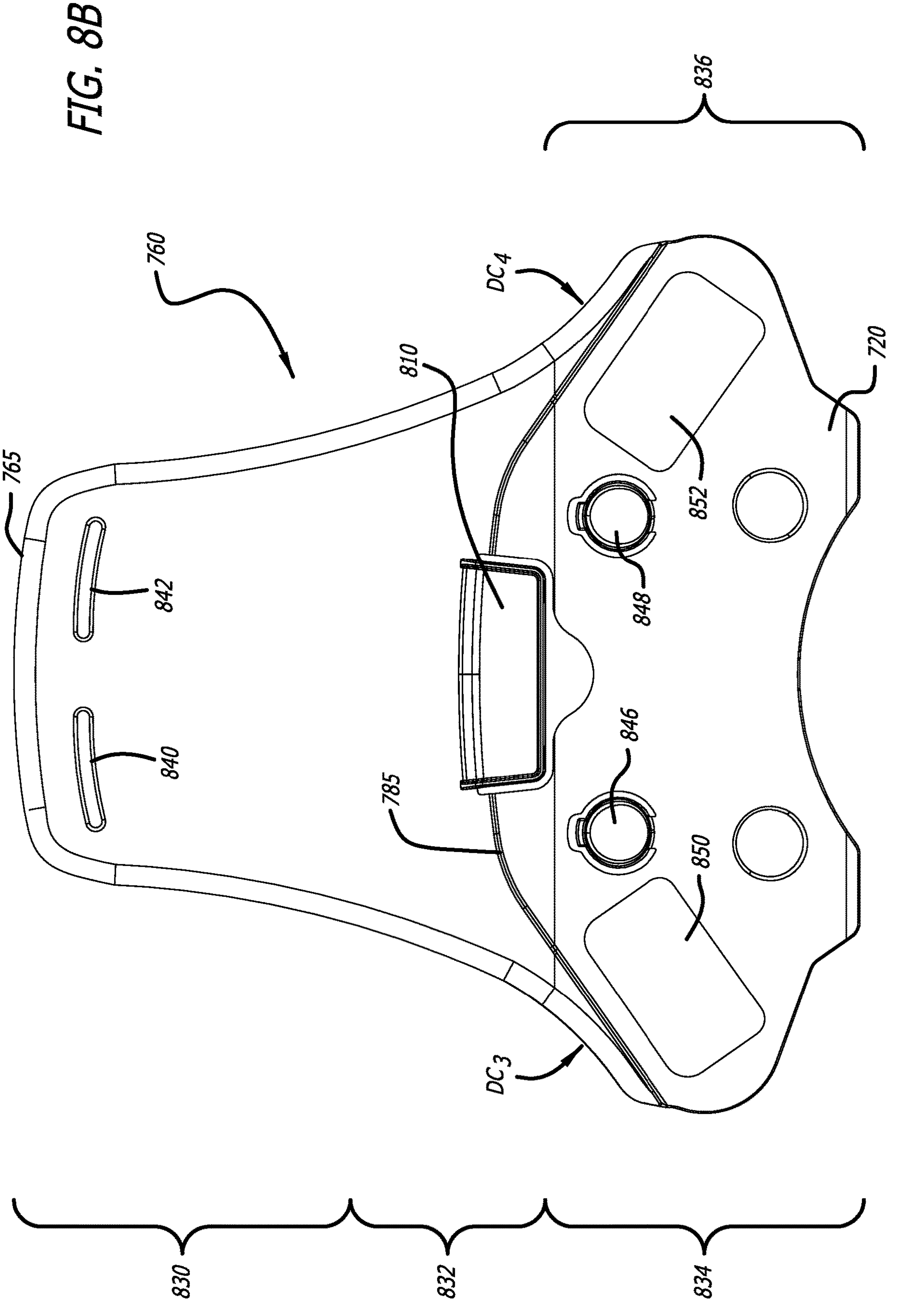
FIG. 8B is a perspective view of a second type of extension panel deployed on a posterior panel as shown in FIG. 7A.

As still shown in FIG. 8B, the left lower region 834 features a third strap slot 850 is positioned to be in horizontal alignment with the first strap guide 734 of the first posterior panel 720 when the second extension panel 760 is attached to the first posterior panel 720. Similar in orientation, a fourth strap slot 852 is positioned to be in horizontal alignment with the second strap guide 735 when the second extension panel 760 is attached to the first posterior panel 720. The degrees of curvature ($DC_3$-$DC_4$) along perimeter sections of the second extension panel 760 are more substantial than the degrees of curvature ($DC_1$-$DC_2$) along perimeter sections of the first extension panel 750 as shown in FIG. 8A.

Figure 8C:
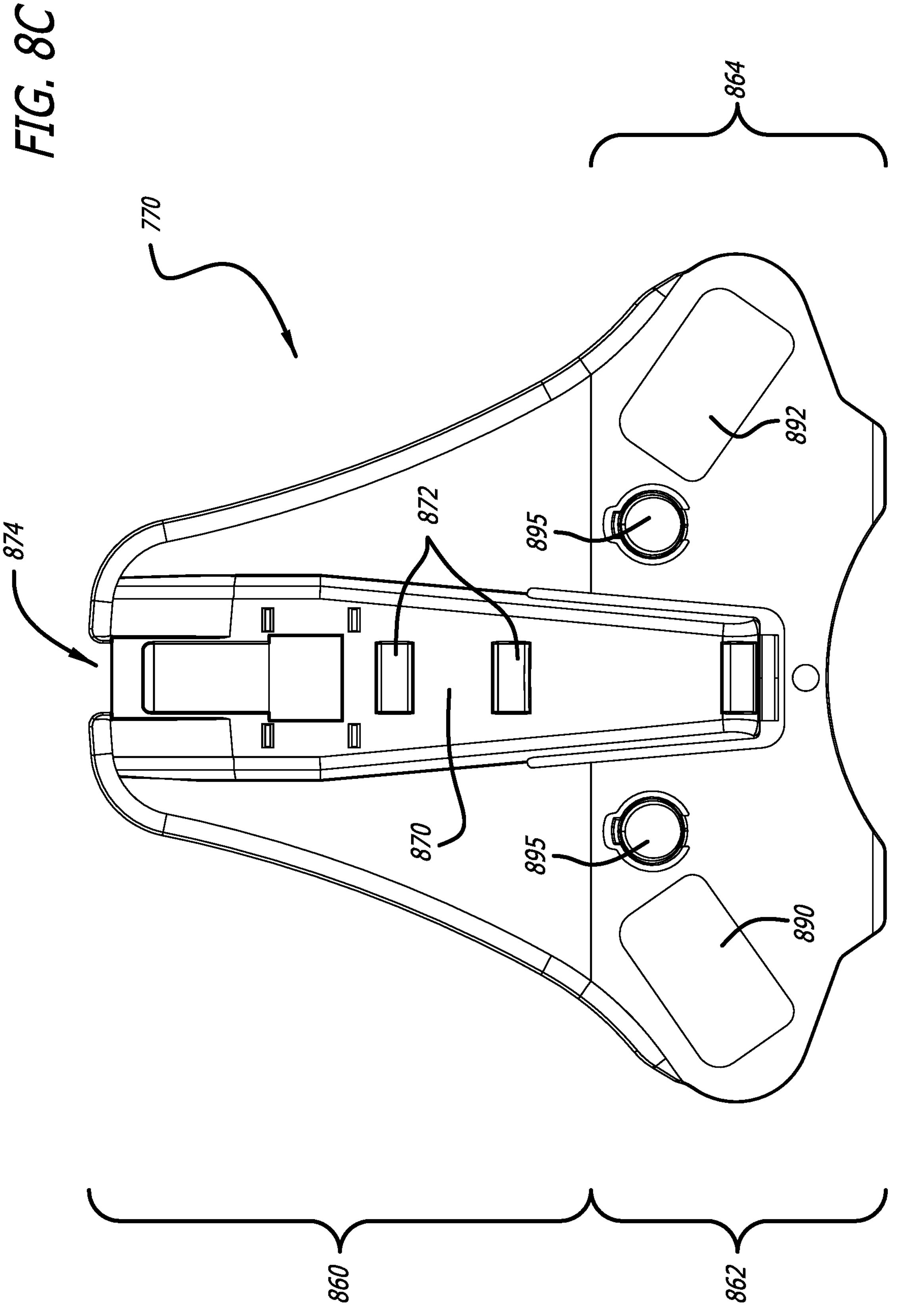
FIG. 8C is a perspective view of a third type of extension panel attached to the posterior panel as shown in FIGS. 7A-7B.

Referring now to FIG. 8C, a perspective view of a third type of extension panel 770 (hereinafter, "third extension panel 770"), configured to be attached on a posterior panel 720 or 795 as illustrated in FIGS. 7A-7B, is shown. Similar to the second extension panel 760, the third extension panel 770 is generally configured with a polygonal shape (e.g., hexagonal configuration), including an upper region 860, a left lower region 862 and a right lower region 864. Intersecting the upper region 860 and the lower regions 862/864 of the third extension panel 770, a cantilever support 870 is configured to secure and maintain a cervical collar adjustment rod 900 with height-setting openings 905 of FIG. 9 sized for engaging with one or more fasteners 872 located as part of the cantilever support 870 when the rod 900 is inserted into a channel 874 of the cantilever support 870.

The left lower region 862 features a first strap slot 890, which is positioned to be in horizontal alignment with the first strap guide 734 of the first posterior panel 720 when the third extension panel 770 is attached to the first posterior panel 720. Similar in orientation, a second strap slot 892 is positioned to be in horizontal alignment with the second strap guide 735 when the third extension panel 770 is attached to the first posterior panel 720. Each of the one or more locking protrusions 895 may be position between the cantilever support 870 and a corresponding strap slot 890/892 and are sized to be securely coupled to the locking slots 730 of a posterior panel (e.g., the first posterior panel 720) as shown in FIG. 7A.

Figure 9:
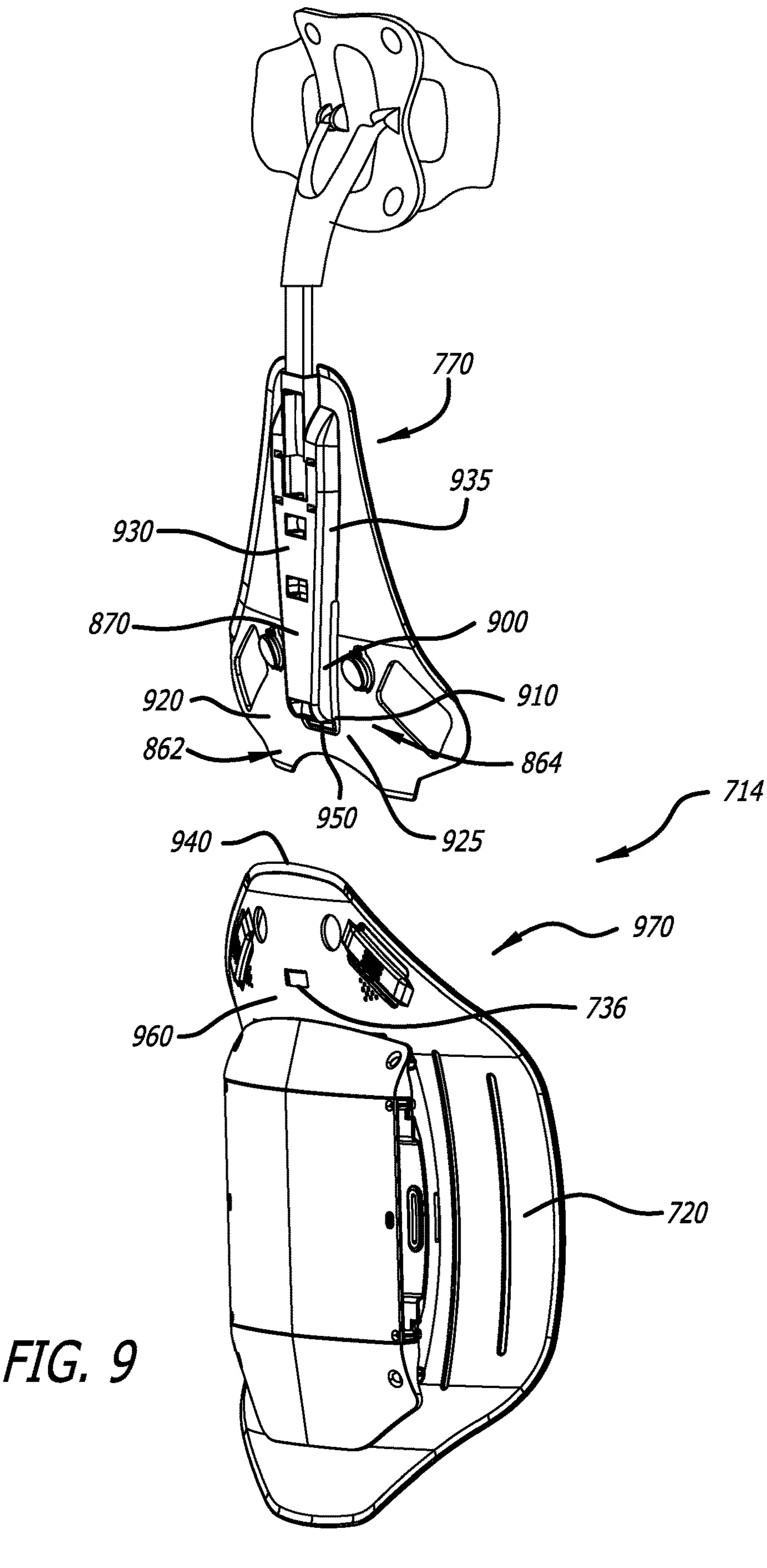
FIG. 9 is a perspective view of a third type of extension panel deployed on a posterior panel as shown in FIGS. 7A-7B.

Referring now to FIG. 9, a rear-facing view of the posterior bracing system 714 of FIG. 7A with the third extension panel 770 of FIG. 8C is shown. Herein, the cantilever support 870 further includes an enclosed end 900, which is disengaged from portions of the left lower region 862 and the right lower region 864 of the third extension panel 770 through the cut-out area 910. The cut-out area 910 constitutes a separation between (i) a posterior surface 920 for the left lower region 862 of the third extension panel 770 and a first rail 930 of the cantilever support 870 and (ii) a posterior surface 925 for the right lower region 864 of the third extension panel 770 and a second rail 935 of the cantilever support 870. At a time of connection, a top perimeter 940 of the first posterior panel 720 is inserted into the cut-out area 910 as a stabilization component 950 slidably engages to the stabilization slot 736 to provide additional lateral stability for the third extension panel 770. Hence, the cantilever support 870 is positioned on the posterior side 960 of the first posterior panel 720 while other portions of the third extension panel 770 (e.g., first and second lower regions 862 and 864) are positioned on the anterior side 970 of the first posterior panel 720.

III. General Architecture—Anterior Bracing System

Figure 10A:
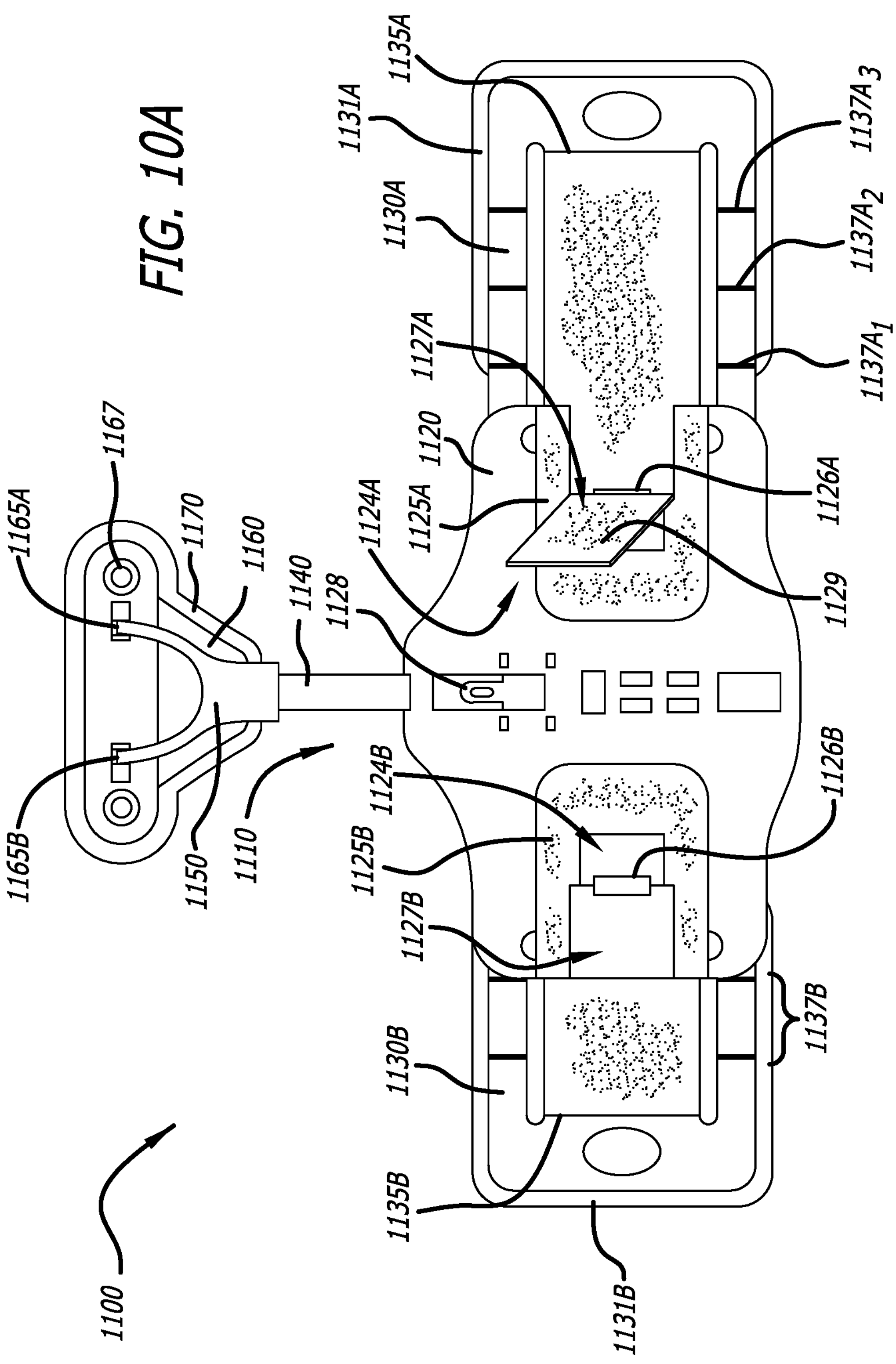
FIGS. 10A-10D are front perspective views of an exemplary embodiment of an orthopedic brace with an anterior bracing system.

Referring now to FIGS. 10A-10D, a plurality of front perspective views of an exemplary embodiment of an orthopedic brace with an anterior bracing system are shown in accordance with some embodiments. Referring to FIG. 10A, an anterior bracing system 1110 of an orthopedic bracing system 1100 is shown that includes an anterior panel 1120, an extension rod 1140 coupled to the anterior panel 1120 that extends in a superior direction therefrom, and a first and second telescopic lateral panels 1130A, 1130B (collectively, lateral panels 1130) that extend laterally therefrom. Herein, the lateral panels 1130 may be made of a rigid or semi-rigid material such as any type of hardened, flexible plastic (e.g., sheet of polyethylene, polycarbonate, etc.). As a result, the lateral panels 1130 may be angularly bent into a concave form to provide lateral support for the orthopedic bracing system 1100.

As shown, the anterior panel 1120 includes an opening receptacle for receiving the extension rod 1140, where an extension rod locking member 1128 rotates between open and closed positions to lock (or retain) the extension rod 1140 in a particular position, where the position of the extension rod 1140 refers to an amount that the extension rod 1140 extends in the superior direction. The anterior panel 1120 also includes a pair of locking mechanisms 1124A, 1124B (collectively, locking mechanisms 1124) disposed on an anterior side, where the locking mechanisms 1124 are configured to engage (couple) with fastener material disposed on an anterior side of the lateral panels 1130.

Further, the locking mechanisms 1124 each include rotatable locking members 1127A, 1127B (collectively, locking members 1127) that are configured to rotate about hinges 1126A, 1126B (collectively, hinges 1126) and fastener portions 1125A, 1125B including a first fastener material (collectively, fastener portions 1125). The locking members 1127 are configured to rotate about their corresponding hinges between an open position and a closed position (or locked position). The closed position refers to the locking member in a position to contact the anterior side of the lateral panels 1130. The open position refers to the locking member being at any position other than the closed position. Further, the locking member includes first and second sides, where a first side includes first fastener material and a second side includes second fastener material. The first side refers to the anterior facing side when the locking member is in the closed position and the second side refers to the posterior facing side when the locking member is in the closed position. Thus, the second side is configured to contact the anterior side of the lateral panels 1130 when the locking member (e.g., rotatable locking member 1127A or 1127B) is placed in the closed position.

Further, the terms "first fastener material" and "second fastener material" may refer to complementary components of a hook and loop fastener system such that the first and second fastener materials are configured to couple upon contact.

Additionally, FIG. 10A illustrates that the lateral panels 1130 include filler 1131A, 1131B (collectively, filler 1131 or padding 1131) on a posterior side, with the padding 1131 being configured to rest against the patient body. Additionally, each lateral panel 1130 includes a portion of its anterior side having disposed thereon a second fastener 1135A, 1135B (collectively, first fasteners 1135) that is complementary to the first fasteners 1129 disposed on the rotatable locking members 1127 discussed above. The lateral panels 1130 may also include sizing indicia 1137$A_{1-x}$, and 1137$B_{1-x}$, (where x≥1, and x=3 in FIG. 10A) (collectively, indicia 1137). The indicia 1137 represent predetermined sizing configurations such as large (1137$A_1$, 1137$B_1$), medium (1137$A_2$, 1137$B_2$), and small (1137$A_3$, 1137$B_3$). It is noted that the indicia 1137$B_1$, are merely represented as 1137B. Thus, the indicia 1137 provide a medical professional sizing parameters that guide the extension or retraction of the lateral panels into a particular sizing configuration. As a result, the sizing indicia 1137 provide the advantage of enabling a medical professional (or wearer) the ability to quickly determine an amount that each lateral panel 1130 should be extended or retracted in order to place the anterior bracing system 1110 into a preconfigured size.

In summary, the anterior bracing system 1110 of FIG. 10A includes an anterior panel 1120 having disposed on an anterior side first and second locking mechanisms that configured to rotate between open and closed positions. Further, the anterior bracing system 1110 includes first and second lateral panels 1130 that are coupled to the posterior side of the anterior panel 1120 via guide posts 2120 (see FIG. 11), with the lateral panels 1130 being configured to extend or retract in the medial/lateral directions. The anterior bracing system 1110 is configured to rest against the front torso of a patient and be sized for the patient through extension or retraction of the lateral panels 1130. Once the lateral panels 1130 have been extended a desired amount based on the size of the patient's torso, the locking members 1127 are rotated from an open position to a closed position where first fastener material of the lateral panel contacts second fastener material of the locking member causing a coupling therebetween resulting in the lateral panels being locked in the desired position (e.g., desired amount of extension). The retraction and extension of the lateral panels and locking of the same in a desired position are illustrated in FIGS. 10A-10D and will be described further below.

FIG. 10A also illustrates a wishbone extension coupler (wishbone coupler) 1150 coupled to a distal end of the extension rod 1140. The wishbone coupler 1150 is shown as further coupling to a support chest plate 1160 via insertion mechanisms 1165A, 1165B (collectively, insertion mechanisms 1165). The support chest plate 1160 includes snap connectors 1167 that are adapted to receive complementary buckles (see FIG. 18B & FIG. 20K) shown with padding 1170 disposed on a posterior side. As discussed below, the wishbone coupler 1150 is configured to permit various attachments to couple with the anterior panel 1120 via the extension rod 1140. As noted above, when the orthopedic brace is configured for a TLSO deployment, the wishbone coupler 1150 couples with the support chest plate 1160 and when configured for a CTLSO deployment, the wishbone coupler 1150 couples with a cervical brace (see FIGS. 16A-16C).

Figure 10B:
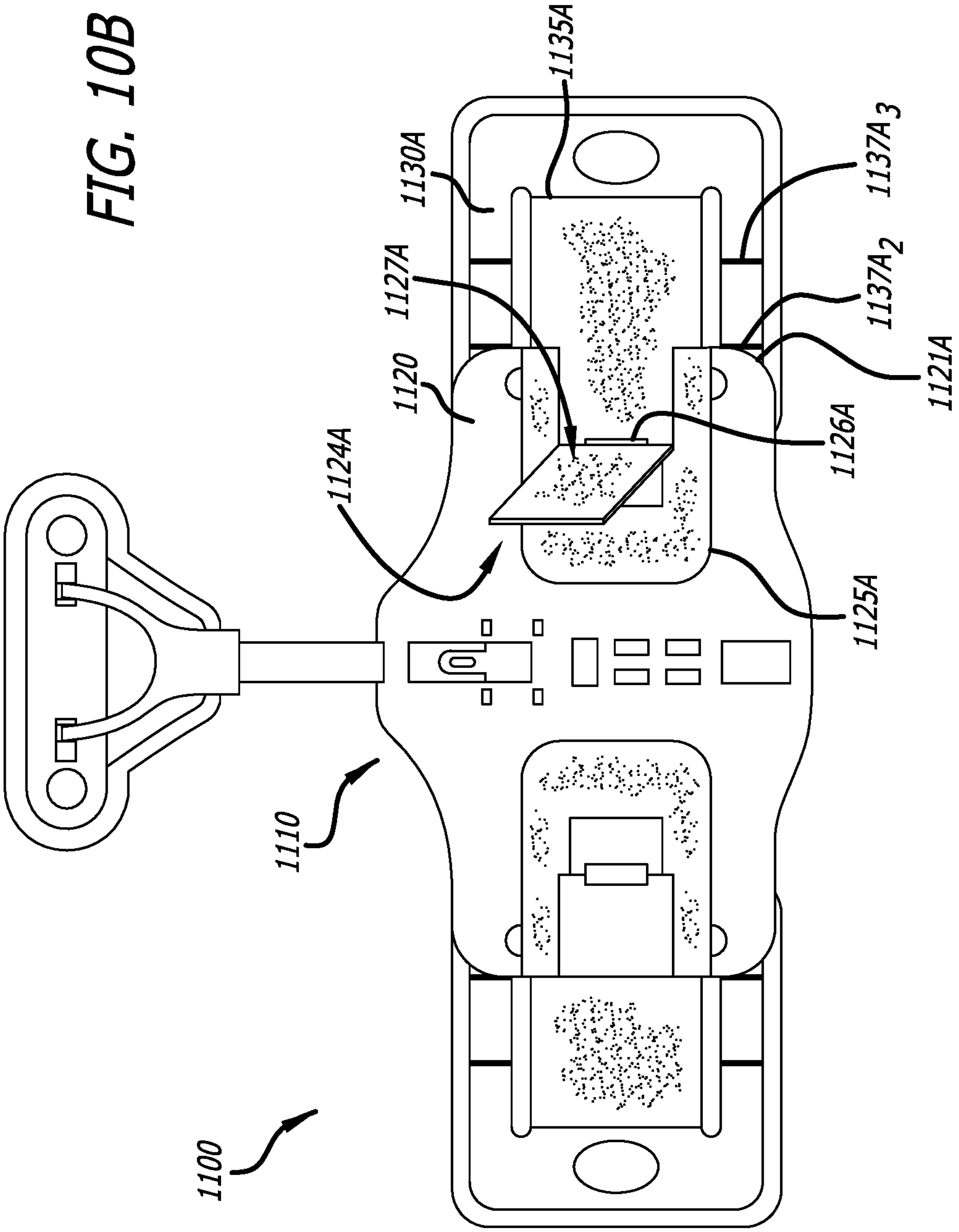

Referring now to FIG. 10B, the first lateral panel 1130A is shown in a retracted position as compared to FIG. 10A, which illustrates the first lateral panel 1130A in a fully extended position. In particular, the first lateral panel 1130A is retracted (slid in a medial direction) from the fully extended position shown in FIG. 10A to a preconfigured size of "medium" as indicated by the indicia 1137$A_2$. For instance, the anterior bracing system 1110 may be sized in accordance with a predetermined sizing configuration through the alignment of an outer (lateral) edge 1124A of the anterior panel 1120 with any of the indicia 1137$A_{1-x}$. As shown, the anterior bracing system 1110 is sized according to the indicia 1137$A_2$ ("medium"). FIG. 10B also illustrates the locking member 1127A in an open position, which allows the lateral panel 1130A to be easily extended or retracted.

Figure 10C:
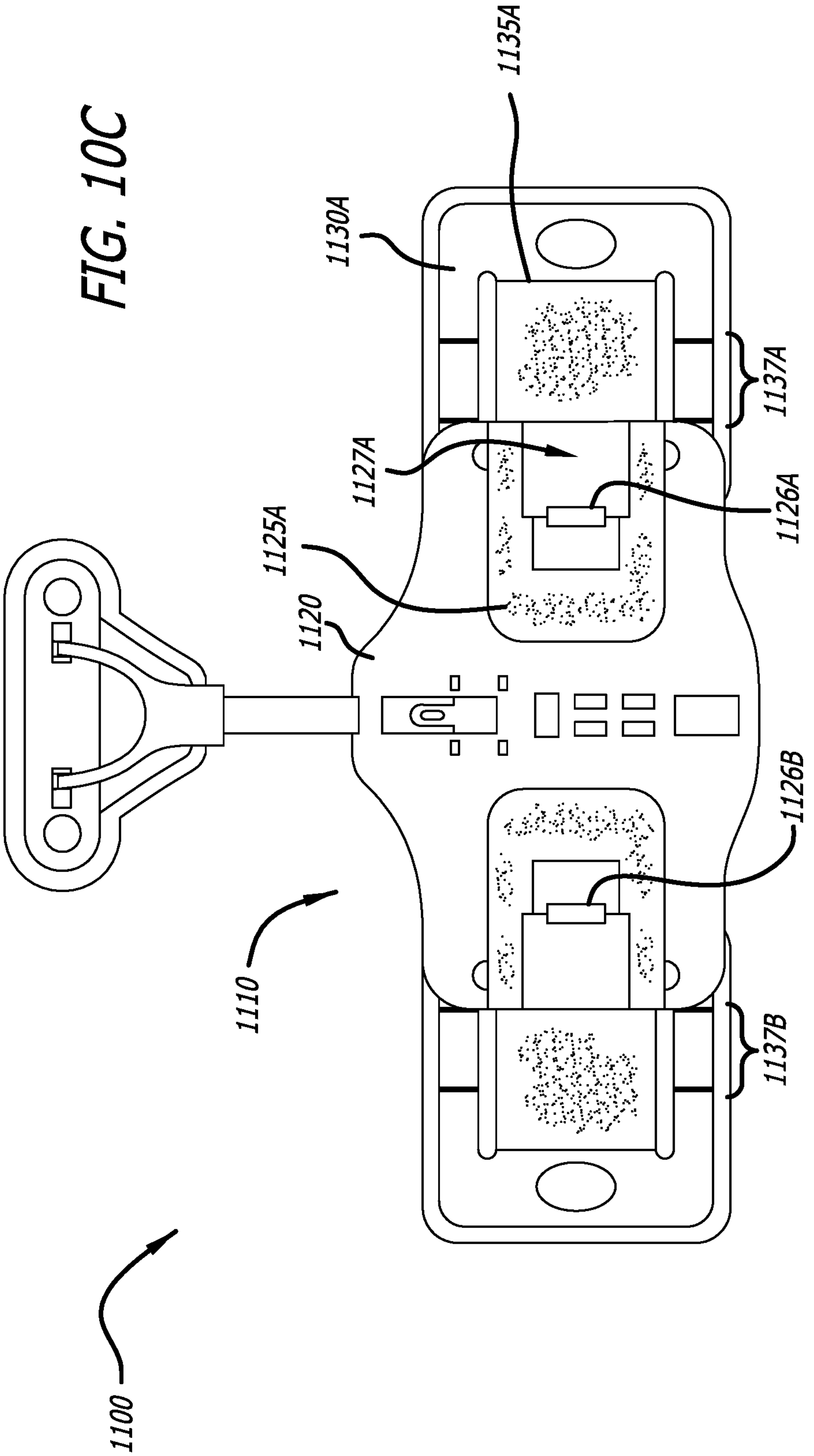

Referring now to FIG. 10C, the locking member 1127A is shown in a closed position resulting in a coupling of the fastener materials disposed on the second side of the locking member 1127A and the anterior side of the lateral panel 1130A. This coupling effectively locks the lateral panel 1130A in its current position (e.g., no further extension or retraction is permitted until the locking member and the lateral panel are uncoupled). The locking member 1127A and the lateral panel 1130A may be uncoupled (and subsequently extended or retracted) through the use of force pulling the locking member 1127A away from the lateral panel 1130A.

Figure 10D:
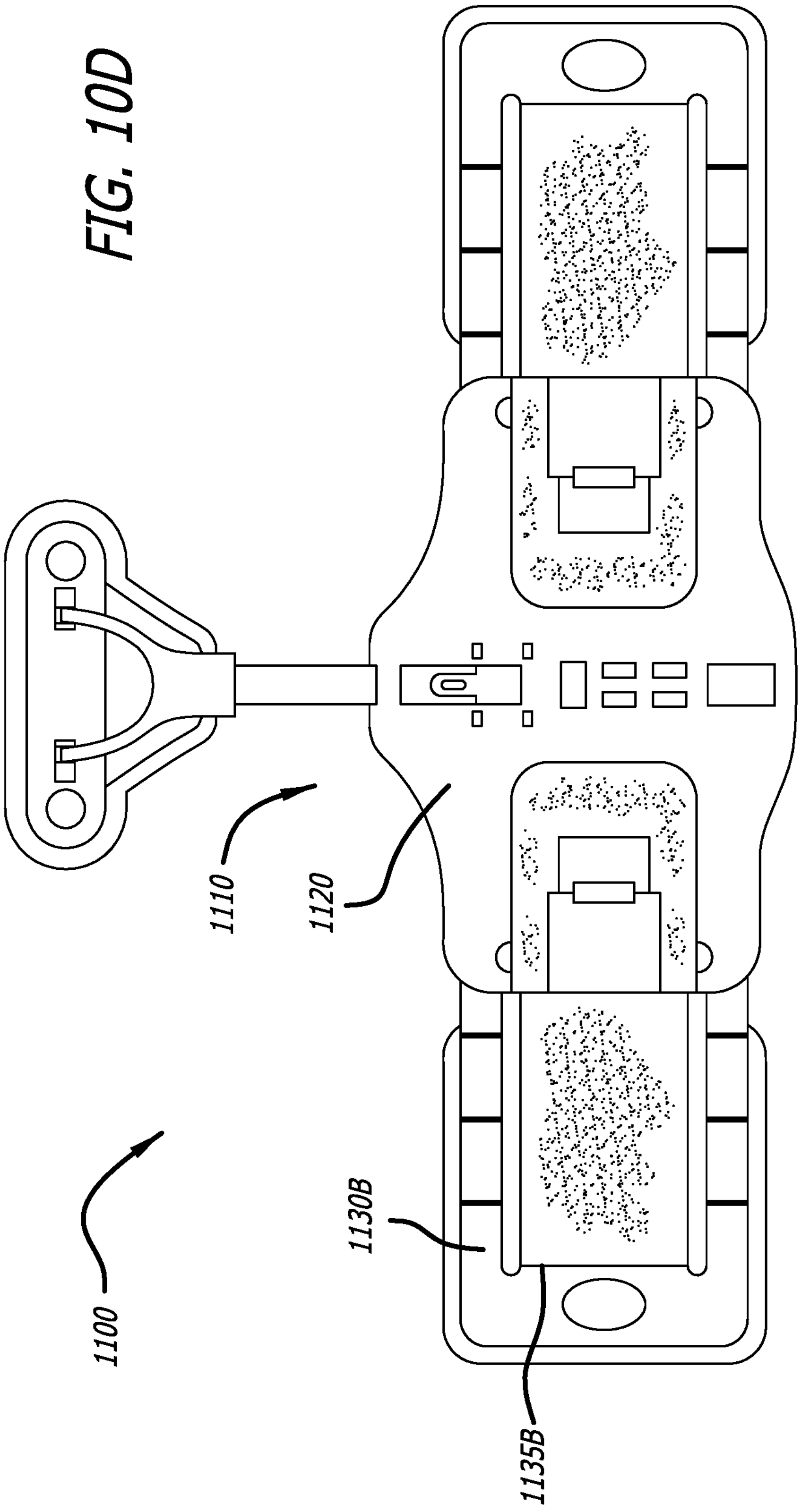

Referring now to FIG. 10D, the second lateral panel 1130B is shown in a fully extended position with the locking member 1127B placed in a closed position. Thus, the lateral panel 1130B is locked in its current position until the locking member 1127B and the lateral panel 1130B are uncoupled.

Figure 11:
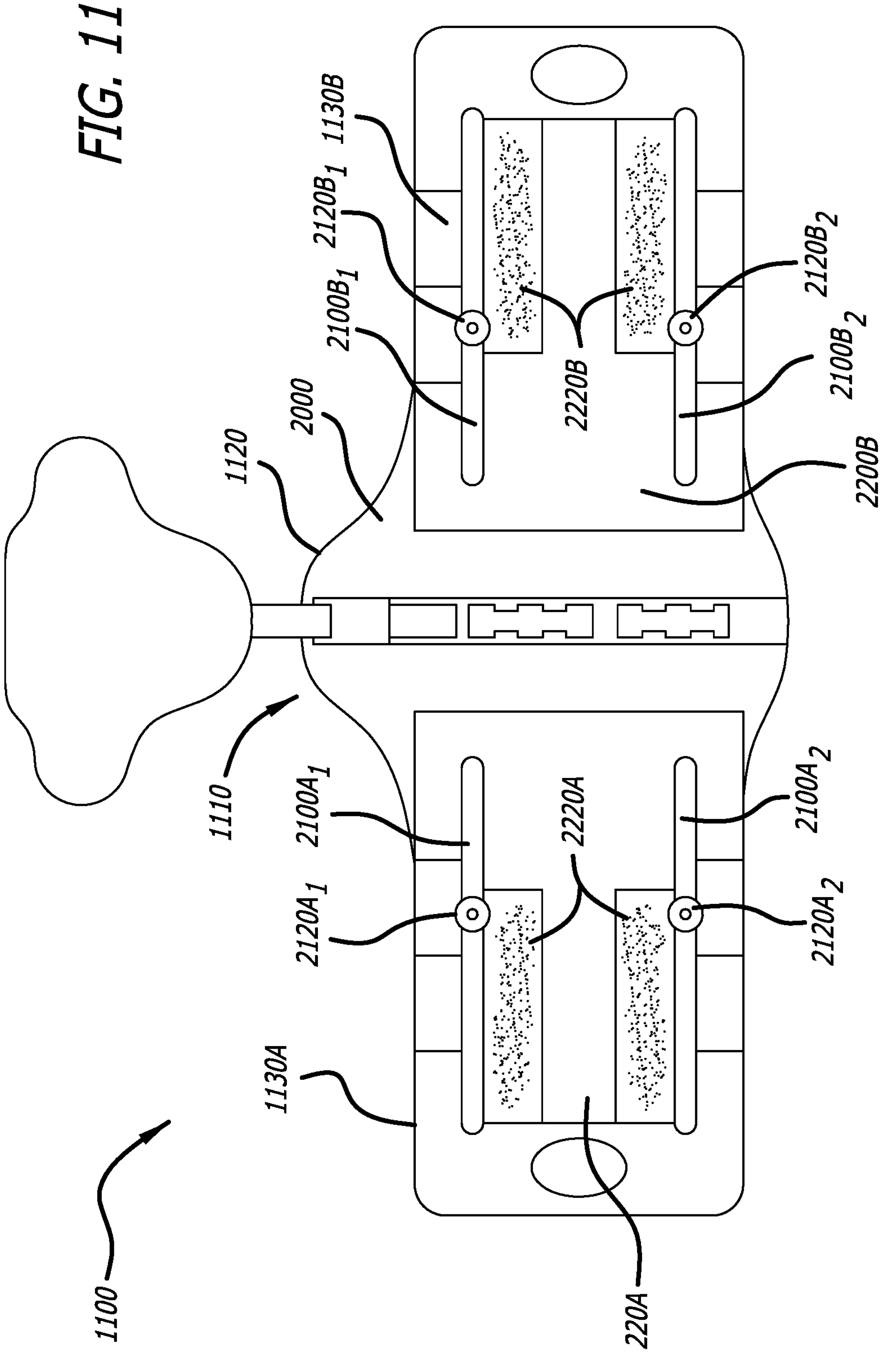
FIG. 11 is a rear perspective view of an exemplary embodiment of the anterior bracing system of FIGS. 10A-10D.

Referring now to FIG. 11, a rear perspective view of an exemplary embodiment of the anterior bracing system of FIGS. 10A-10D is shown in accordance with some embodiments. The rear perspective of FIG. 11 illustrates the posterior side (or interior side) 2000 of the anterior bracing system 1110. As shown, each of the lateral panels 1130A and 1130B includes a set of guide channels 2100$A_{1-2}$ and 2100$B_{1-2}$ (collectively, guide channels 2100), respectively. Each of the guide channels 2100$A_{1-2}$ and 2100$B_{1-2}$ is configured to couple with a corresponding guide post 2120$A_{1-2}$, 2120$B_{1-2}$ (collectively, guide post 2120). As shown, the guide posts 2120 are received into the corresponding guide channels 2100, thereby enabling the lateral panels 1130 to slide (extend or retract) along the guide posts 2120.

It is noted that the guide channels 2100 are shown having smooth edges providing for easy, unrestricted or unopposed movement of the lateral panels 1130. However, in some embodiments, the guide channels 2100 may include various ridges or notches that provide some resistance in the movement of the lateral panels 1130. For instance, the edges of the guide channels 2100 may be jagged or include a series of alternative peaks and valleys. In other embodiments, the guide channels 2100 may include either notches or grooves at intervals corresponding to the sizing indicia 1137.

According to one embodiment of the disclosure, the guide posts may include a columnar body extending in a posterior direction from the anterior panel 1120 such that the columnar body is disposed within a corresponding guide channel 2100. The distal end of the columnar body may include a posterior cap that is sized larger than the width of the guide channels 2100, which operates to maintain the coupling between the lateral panels 1130 and the anterior panel 1120. The posterior cap may take various shapes, which may include a circular cross-section as shown. Further, in assembly, the columnar body may be disposed in an aperture of the anterior panel 1120 and where an anterior end may include an anterior cap that prevents the columnar body from fully extending through the aperture (see FIG. 10D). The lateral panels 1130 may be coupled with the anterior panel 1120 such that the column body of each guide post 2120 are disposed within corresponding guide channels 2100 of the lateral panels. The posterior caps may then be attached to each guide post 2120 (e.g., via a screw fastener or adhesive).

Additionally, the anterior side of each lateral panel 1130 may include one or more strips of fastener material 2220A, 2220B that is configured to couple with corresponding fastener material disposed on filler 4000A, 4000B (see FIGS. 13A-13B) or couple directly with the anterior side of the filler 4000A, 4000B.

Figure 12A:
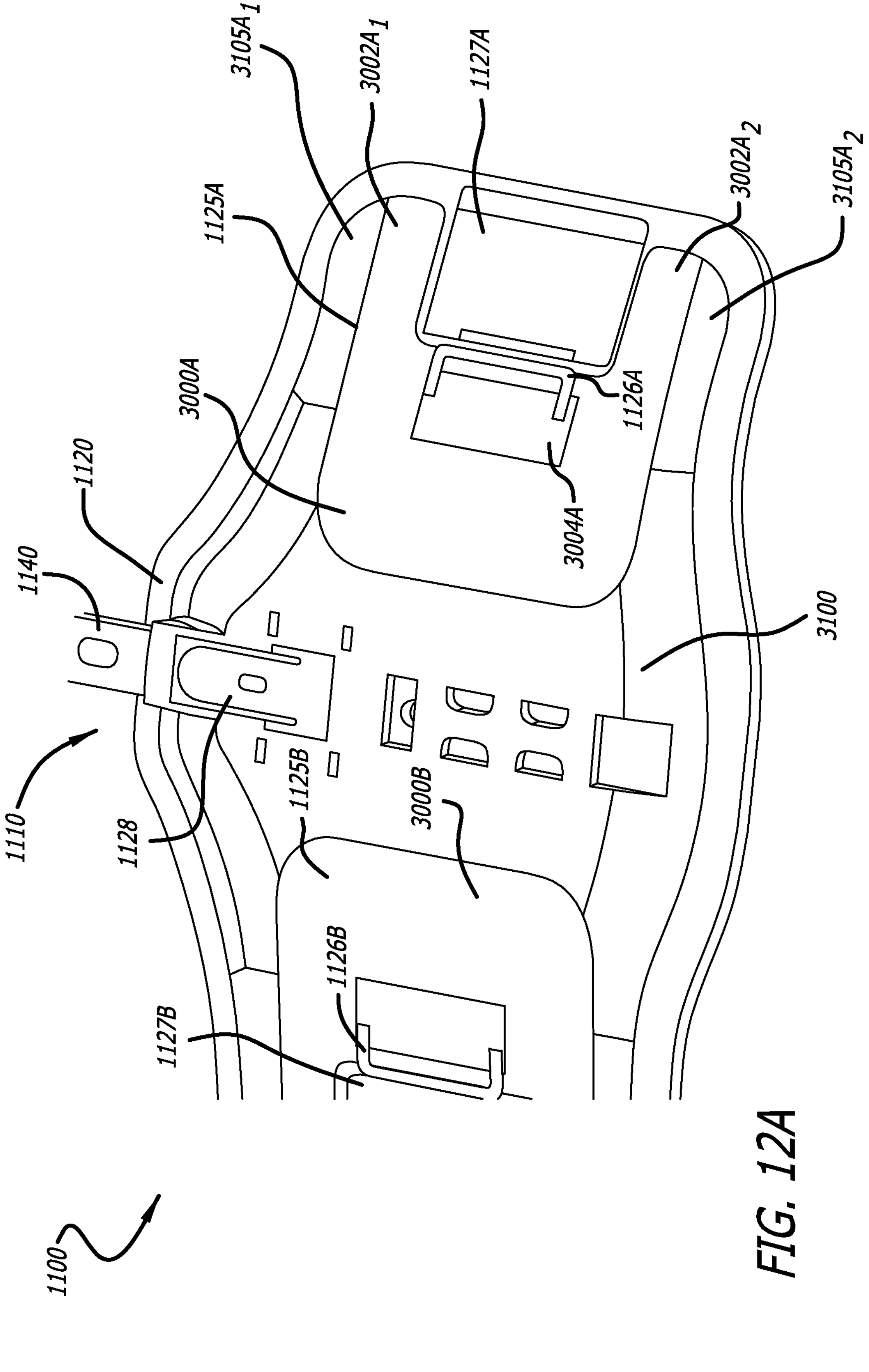
FIG. 12A is a front perspective view of an anterior panel of the anterior bracing system of FIGS. 10A-10D.

Referring now to FIG. 12A, a front perspective view of the anterior panel 1120 of the anterior bracing system 1110 of FIGS. 10A-10D is shown in accordance with some embodiments. The anterior bracing system 1110 as shown in FIG. 12A illustrates the anterior panel 1120 without the lateral panels 1130 or the extension rod 1140 coupled thereto. Further, the anterior panel 1120 is illustrated without the fastener material overlays that are illustrated in FIGS. 10A-11. Thus, FIG. 12A provides a clear illustration of the locking mechanisms 1124, especially the components of the locking mechanism 1124A. In particular, the locking member 1127A is shown in a closed position and the hinge 1126A around which the locking member 1127A rotates. Additionally, the hinge attachment portion 3004A is shown, which couples the hinge 1126A to the anterior panel 1120 and is disposed under the fastener material overlay of FIGS. 10A-11.

The outline of the fastener portions 1125 are shown such that the fastener portion 1125A includes a base portion 3000A and two portions 3002$A_{1-2}$ that extend laterally from the base portion 3000A and partially surround the locking member 1127A when such is in the closed position. In some embodiments, the anterior panel 1120 may be segmented into a middle body portion 3100 and lateral portions 3105$A_{1-2}$, 3105$B_{1-2}$ that are disposed laterally to the middle body portion 3100. For instance, the two portions 3002$A_{1-2}$ of the fastener portion 1125A may be disposed on the lateral portions 3105$A_{1-2}$. Similarly, although not shown, the two portions 3002$B_{1-2}$ of the fastener portion 1125B may be disposed on the lateral portions 3105$B_{1-2}$.

Figure 12B:
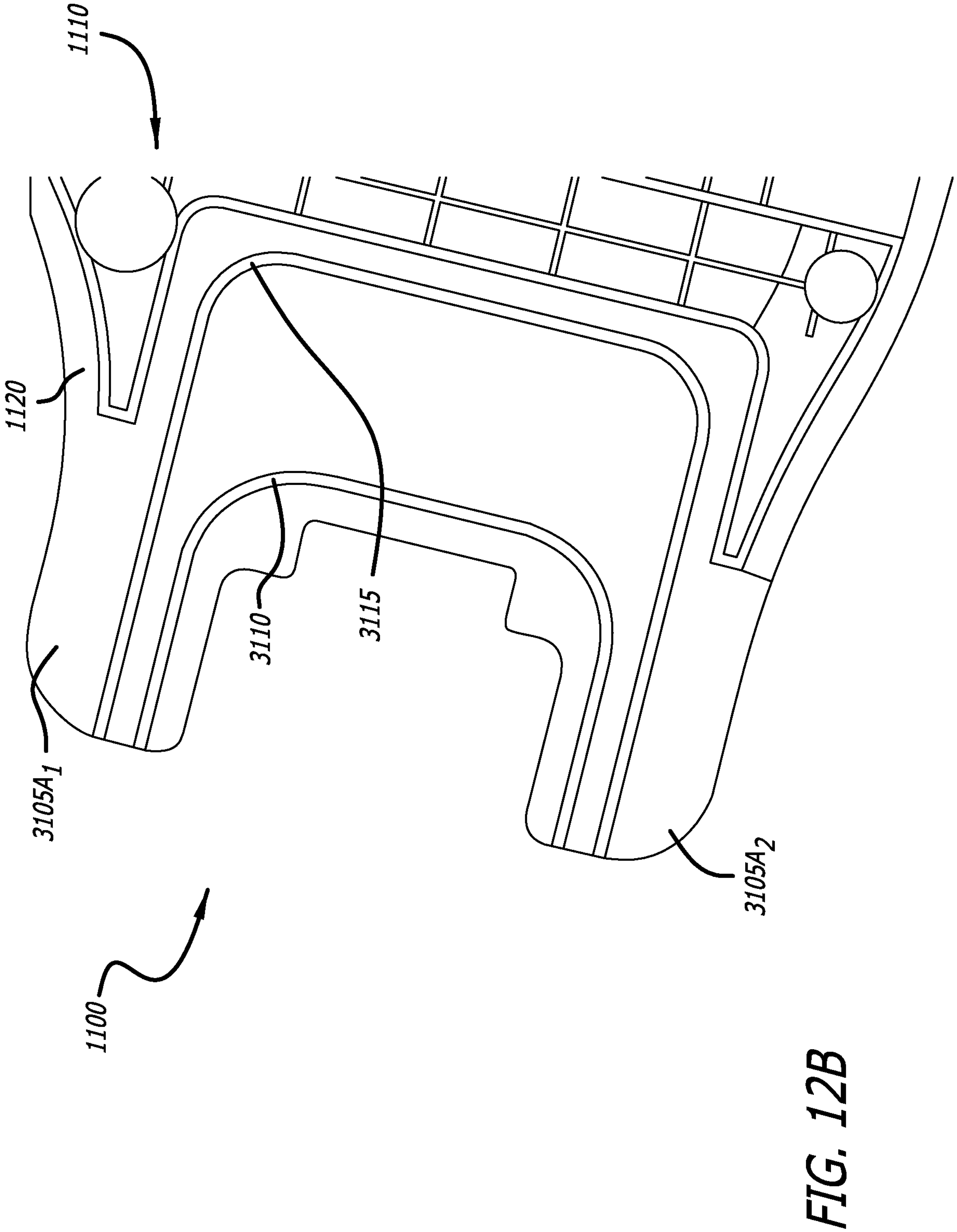
FIG. 12B is a rear perspective view of the anterior panel of FIG. 12A illustrating sewing channels on a first side.

Referring to FIG. 12B, a rear perspective view of the anterior panel of FIG. 12A illustrating sewing channels on a first side is shown in accordance with some embodiments. The rear perspective of FIG. 12B illustrates the anterior side of the anterior panel 1120 and depicts one embodiment of sewing channels 3110, 3115. In some embodiments, the fastener portion 1125A may be sown to the anterior panel 1120 along the sewing channels 3110, 3115. An adhesive may be used in addition in some embodiments as well as an alternative in others.

Figure 13A:
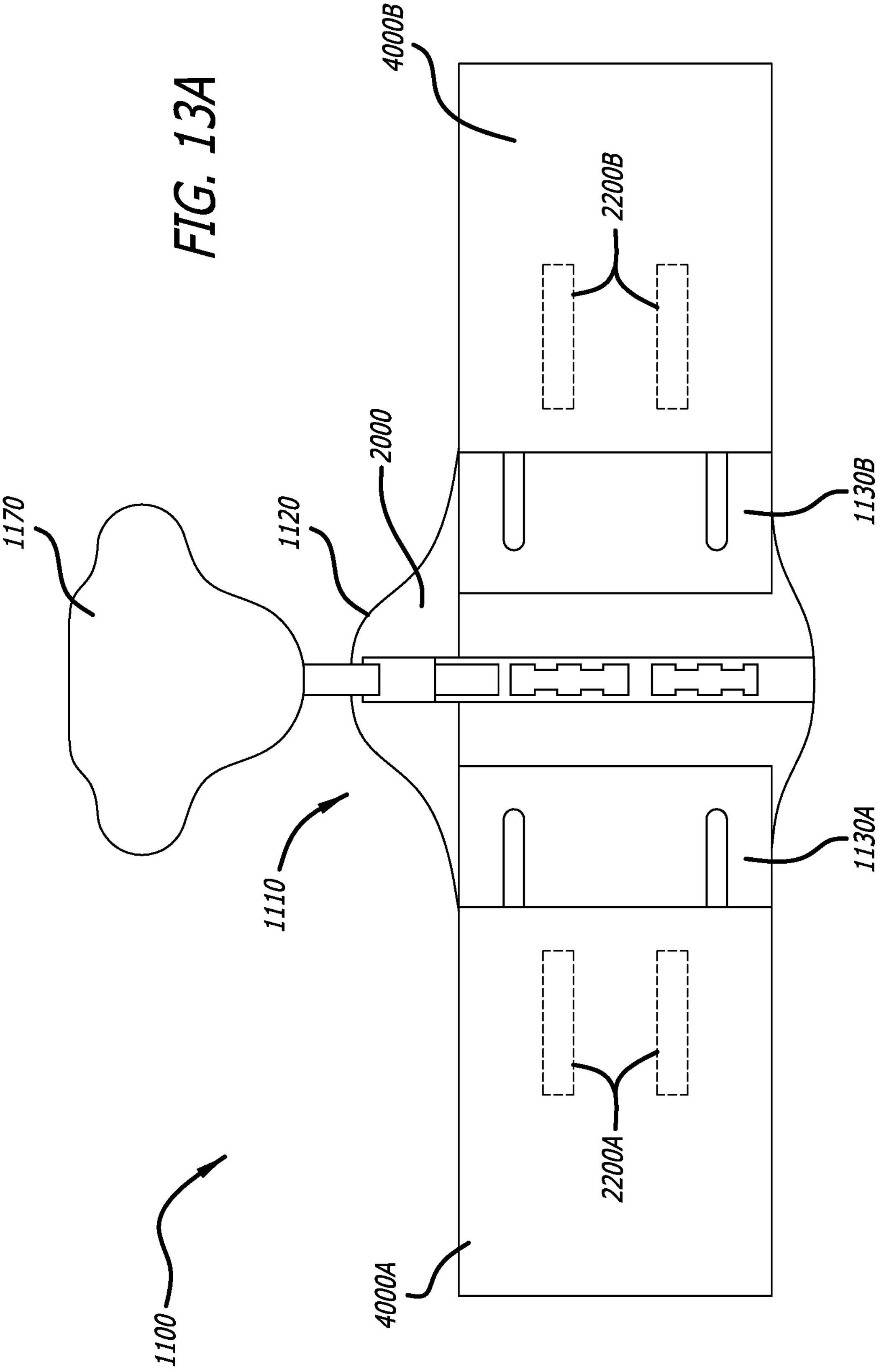
FIGS. 13A-13B are rear perspective views of the anterior panel of FIGS. 12A-12B including filler attached thereto.
Figure 13B:
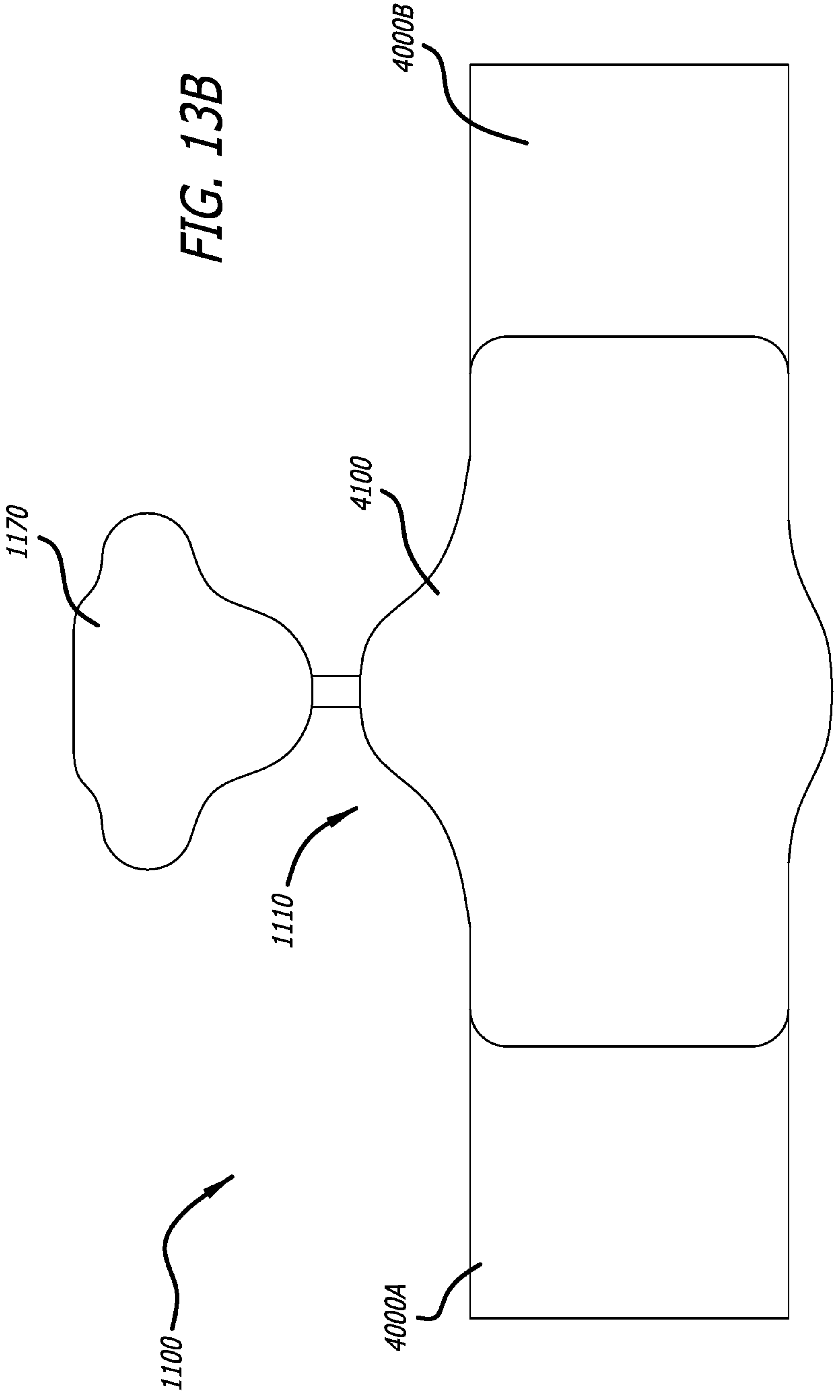

Referring to FIGS. 13A-13B, rear perspective views of the anterior panel of FIGS. 13A-13B including filler attached thereto are shown in accordance with some embodiments. FIG. 13A illustrates that filler (padding)

4000A, 4000B may be placed on an anterior side of the lateral panels 1130 and be configured to rest against the patient thereby providing cushioning between the lateral panels 1130 and the patient's body. The padding 4000A, 4000B may couple with the anterior side of the lateral panels 1130 via one or more strips of fastener material 2220A, 2220B. In some embodiments, the anterior side of the padding 4000A, 4000B includes complementary fastener material strips (not shown). In other embodiments, as shown, the posterior side of the padding 4000A, 4000B couples directly to the strips of fastener material 2220A, 2220B. In other embodiments, various fastener means may be utilized such as snap fasteners and/or buttons (wherein each of the anterior panel and the padding 4000A, 4000B would include a complementary component of a snap fastener and a button fastening mechanism (e.g., a button and a receptacle)). FIG. 13B illustrates that a center torso padding 4100 may also be placed between the patient's body and the anterior bracing system 1110. Although not shown, the padding 4100 may also be coupled to the anterior side of the anterior panel with one or more fastener material strips, snap fasteners and/or buttons.

Figure 14:
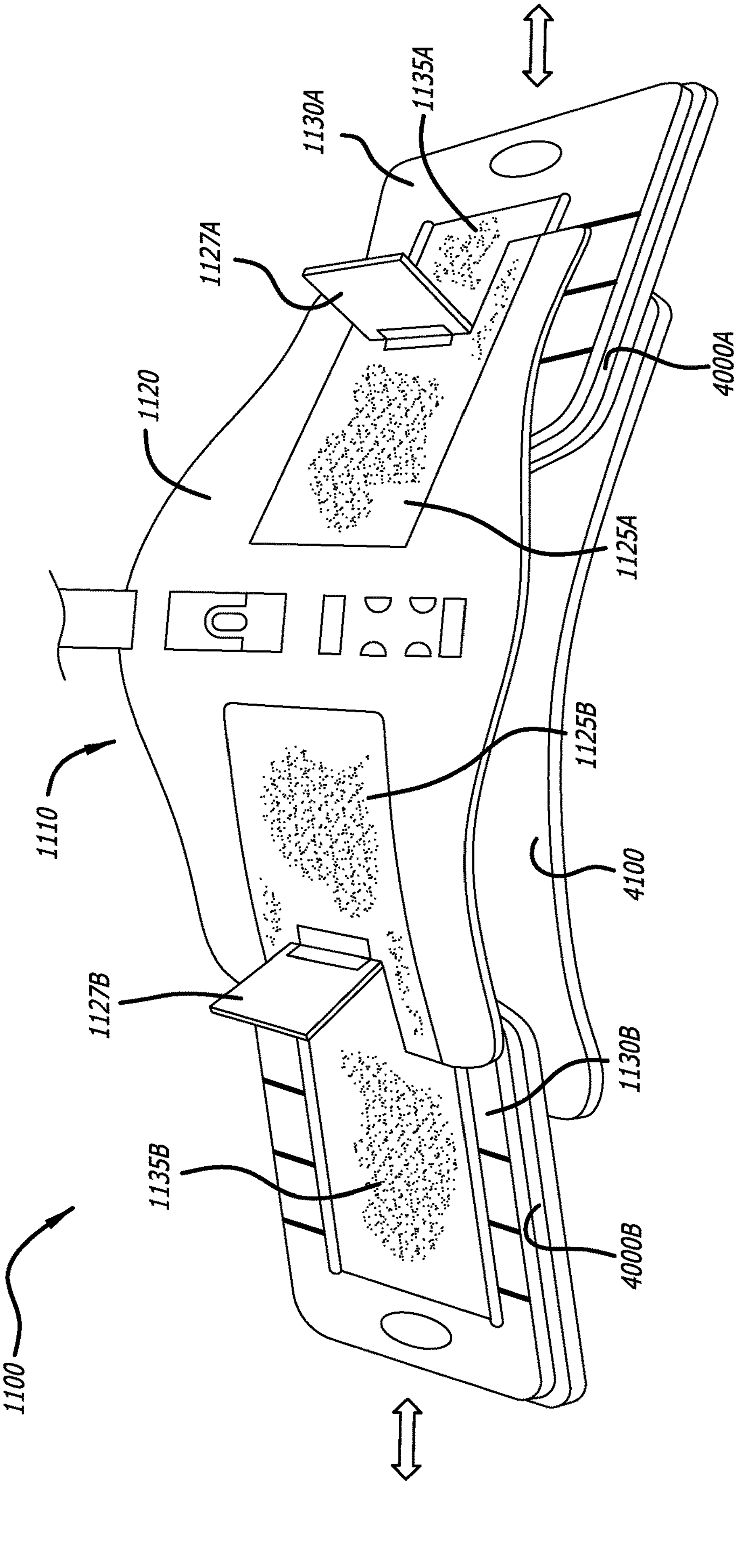
FIG. 14 is a bottom perspective view of the anterior bracing system of FIGS. 10A-10B.

Referring to FIG. 14, a bottom perspective view of the anterior bracing system of FIGS. 10A-10B is shown in accordance with some embodiments. In particular, FIG. 14 illustrates that the lateral panels 1130 may extend or retract such that movement occurs between the anterior panel 1120 and the padding 4100. Further, FIG. 14 provides a clear illustration of each of the locking members 1127, namely locking members 1127A and 1127B, placed in an open position. When in the open position, the locking members 1127 resemble flaps that extend outwardly from the anterior panel 1120.

Figure 15A:
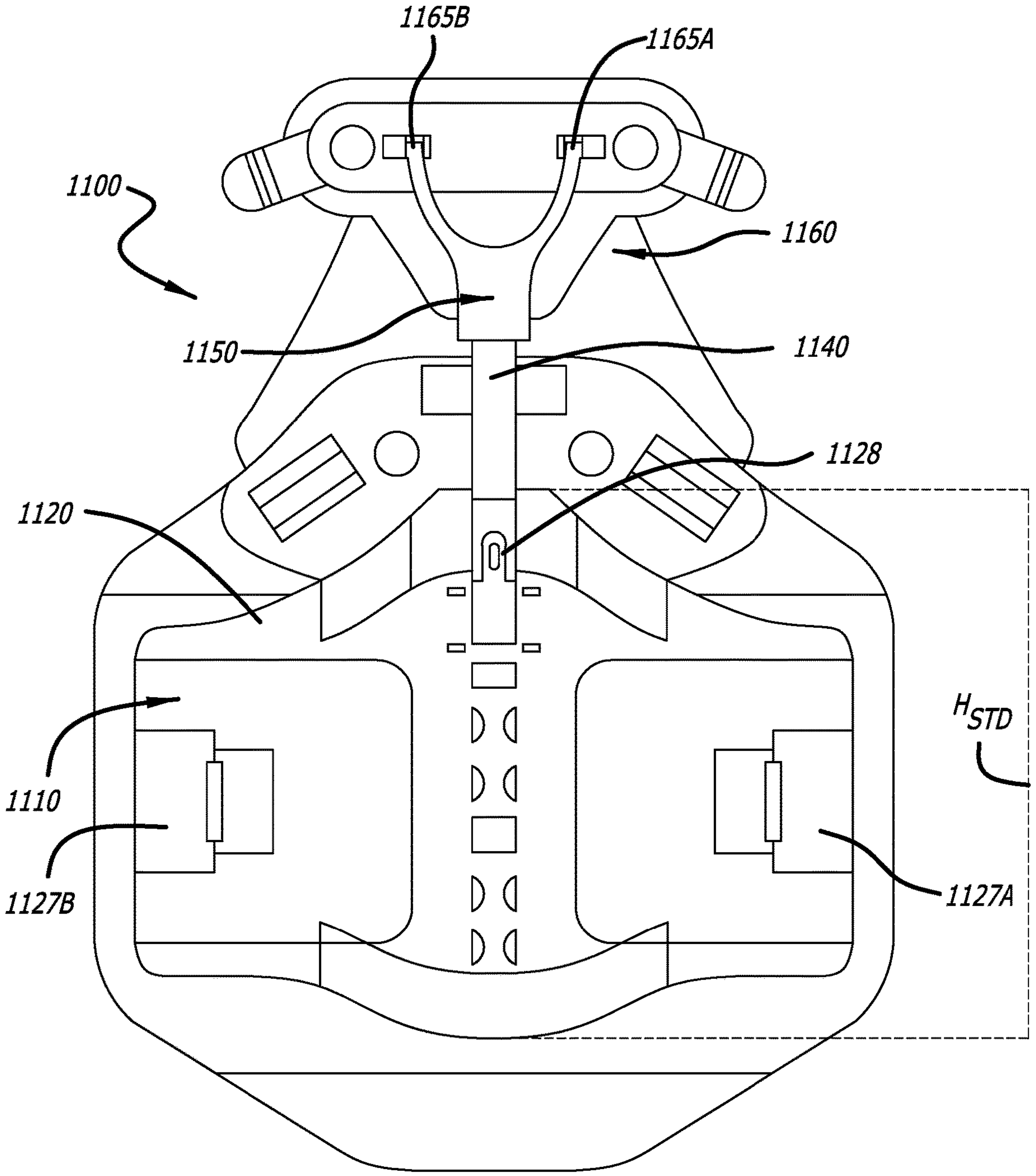
FIG. 15A-15C are additional front perspective views of various sized anterior panels for embodiments of the anterior bracing system of FIGS. 10A-10D.
Figure 15C:
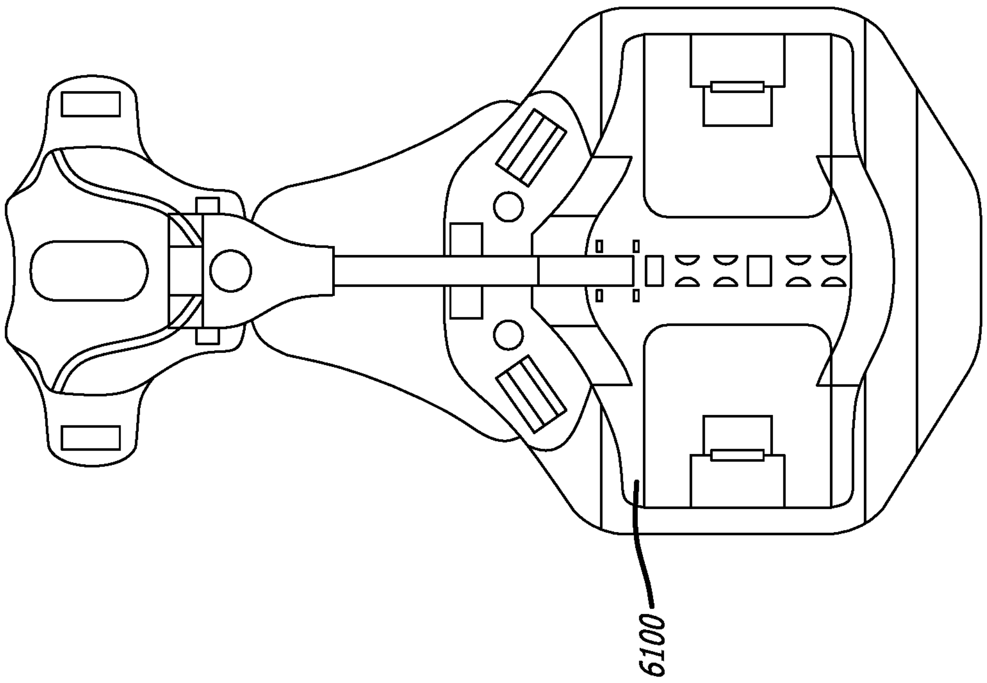
Figure 15B:
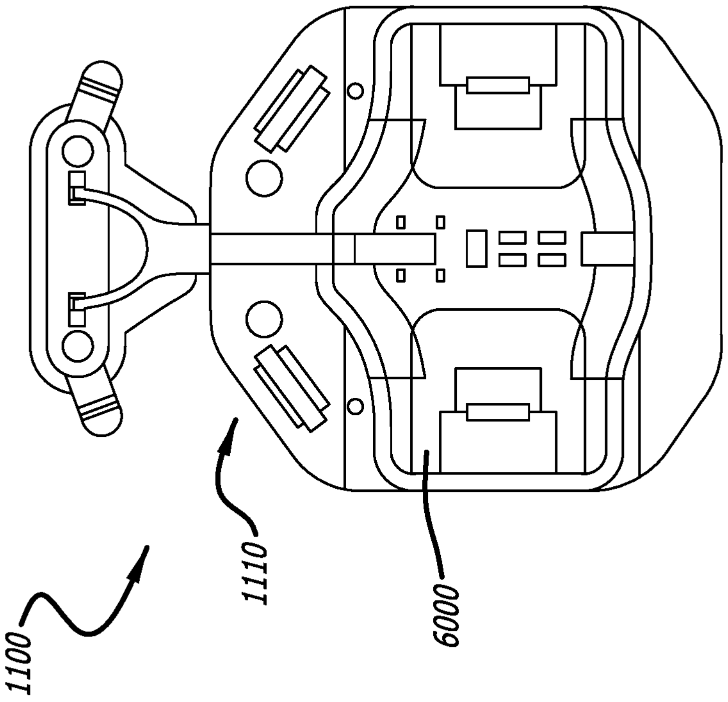

Referring to FIGS. 15A-15C, additional front perspective views of various sized anterior panels for embodiments of the anterior bracing system of FIGS. 10A-10D are shown in accordance with some embodiments. The variations in the sizing of the anterior panels of FIGS. 15A-15C highlight one aspect of the interoperability/interchangeability of the anterior bracing system 1100 disclosed herein. In particular, the anterior panel 1120 of FIG. 15A (and also illustrated in several of FIGS. 10A-14) may be referred to as a standard-sized anterior panel, which is indicated as having a first height ($H_{STD}$). In contrast, the anterior panel 6000 of FIG. 15B may be referred to as a petite-sized anterior panel having a second height that is less than $H_{STD}$ and the anterior panel 6100 of FIG. 15C may be referred to as a grande-sized anterior panel having a third height that is greater than $H_{STD}$.

Although the size of the anterior panels 1120, 6000, 6100 may differ, each maintains the same coupling with the lateral panels 1130 and the extension rod 1140. In some instances, a shortened extension rod may be used with the anterior panel 6000 as compared to the extension rod 1140. Both the extension rod 1140 and any shortened (or lengthened) version may couple with any of the anterior panels 1120, 6000, 6100 as well as with the wishbone coupler 1150.

Thus, a medical professional may easily swap out one anterior panel 1220, 6000, 6100 for another version depending on the size of the patient while utilizing the same components otherwise. In some instances, a shortened extension rod may be used in place of the extension rod 1140.

IV. Gen. Arch.—Wishbone Coupler and Cervical Thoracic Orthosis Clip

Figure 16A:
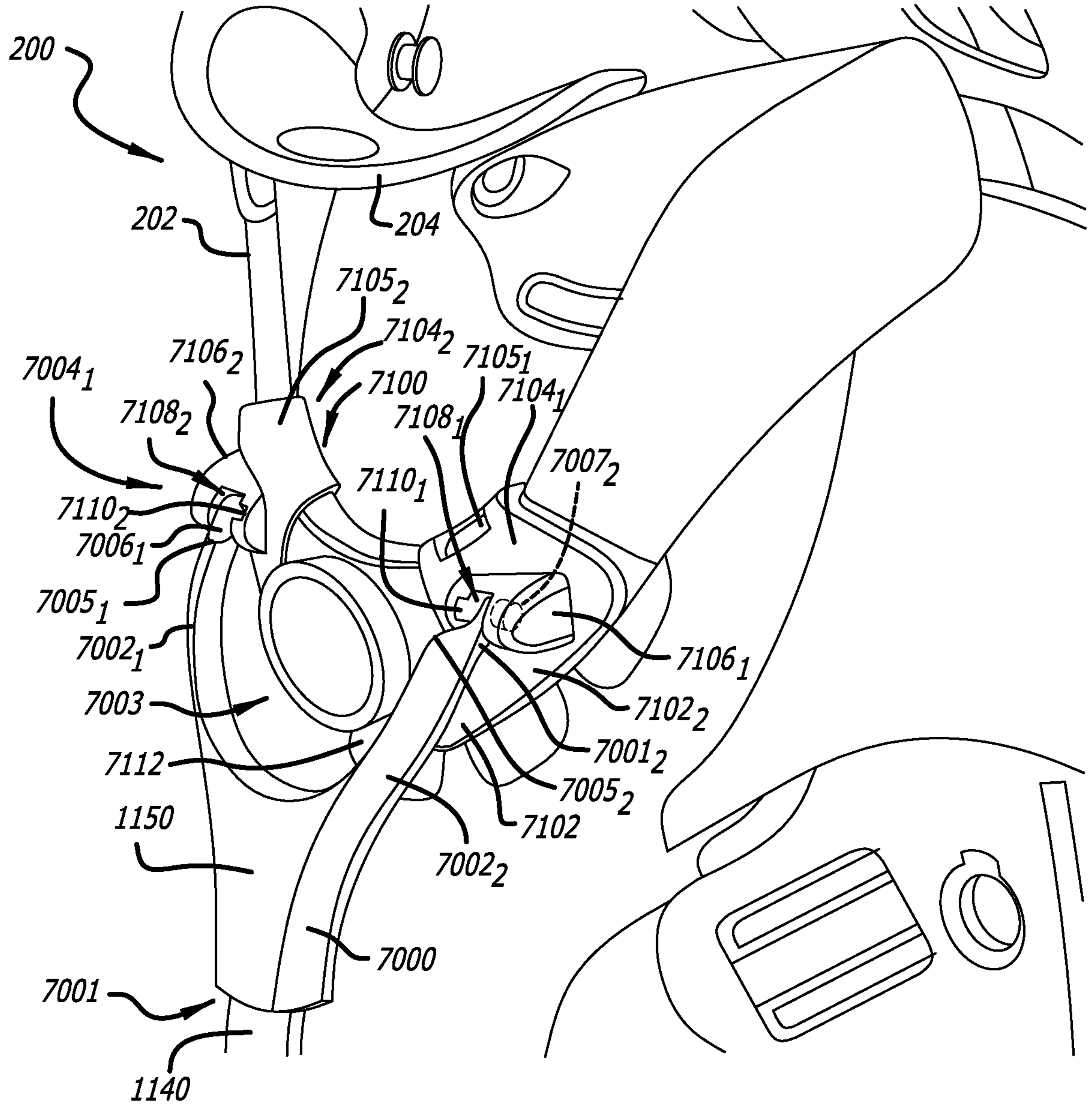
FIG. 16A is a front right side perspective view of a wishbone extension coupler coupling an extension rod and a cervical thoracic orthosis (CTO) clip coupled to a cervical brace.
Figure 16B:
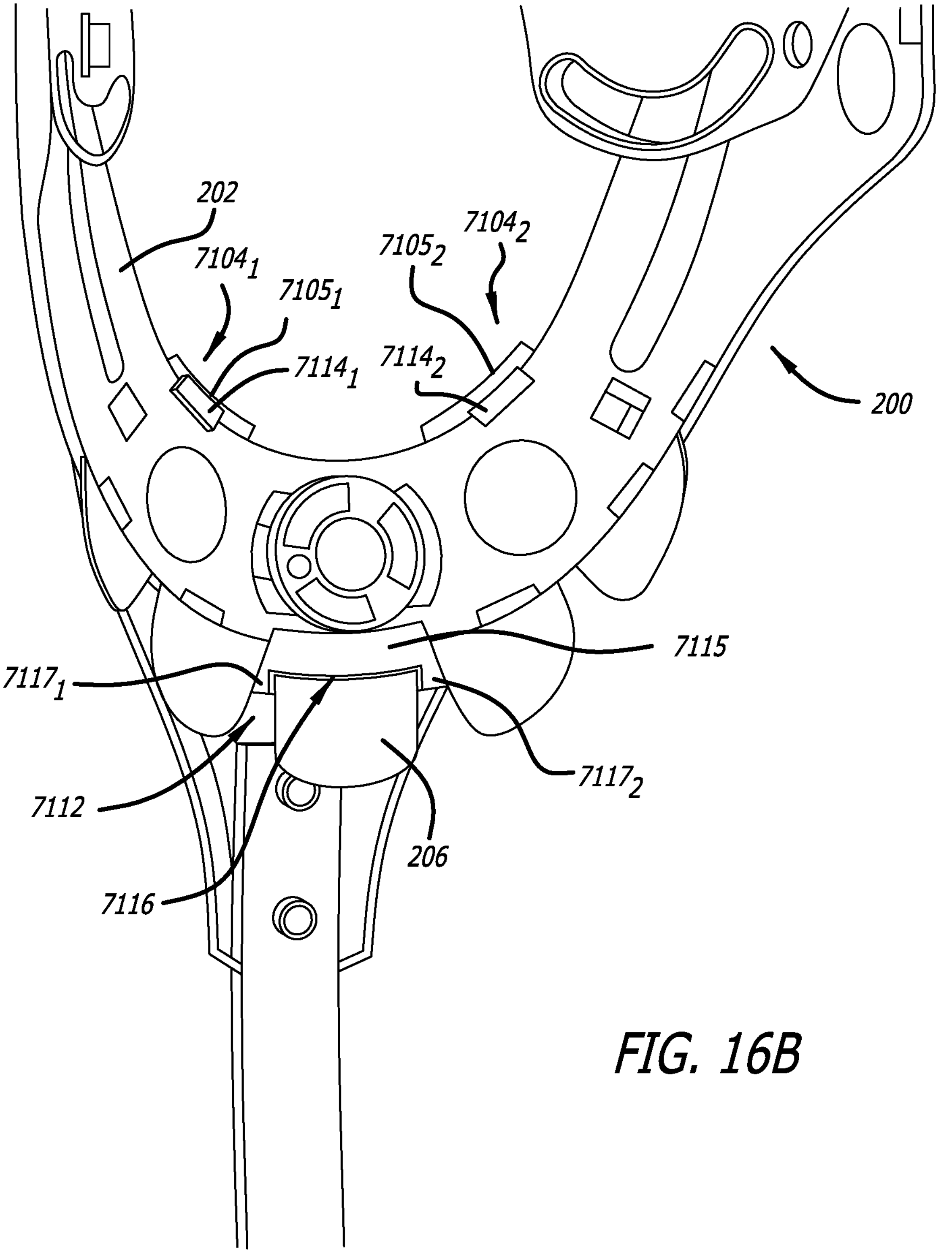
FIG. 16B is a rear perspective view of the wishbone extension coupler coupling the extension rod and the CTO clip coupled to the cervical brace of FIG. 16A.
Figure 16C:
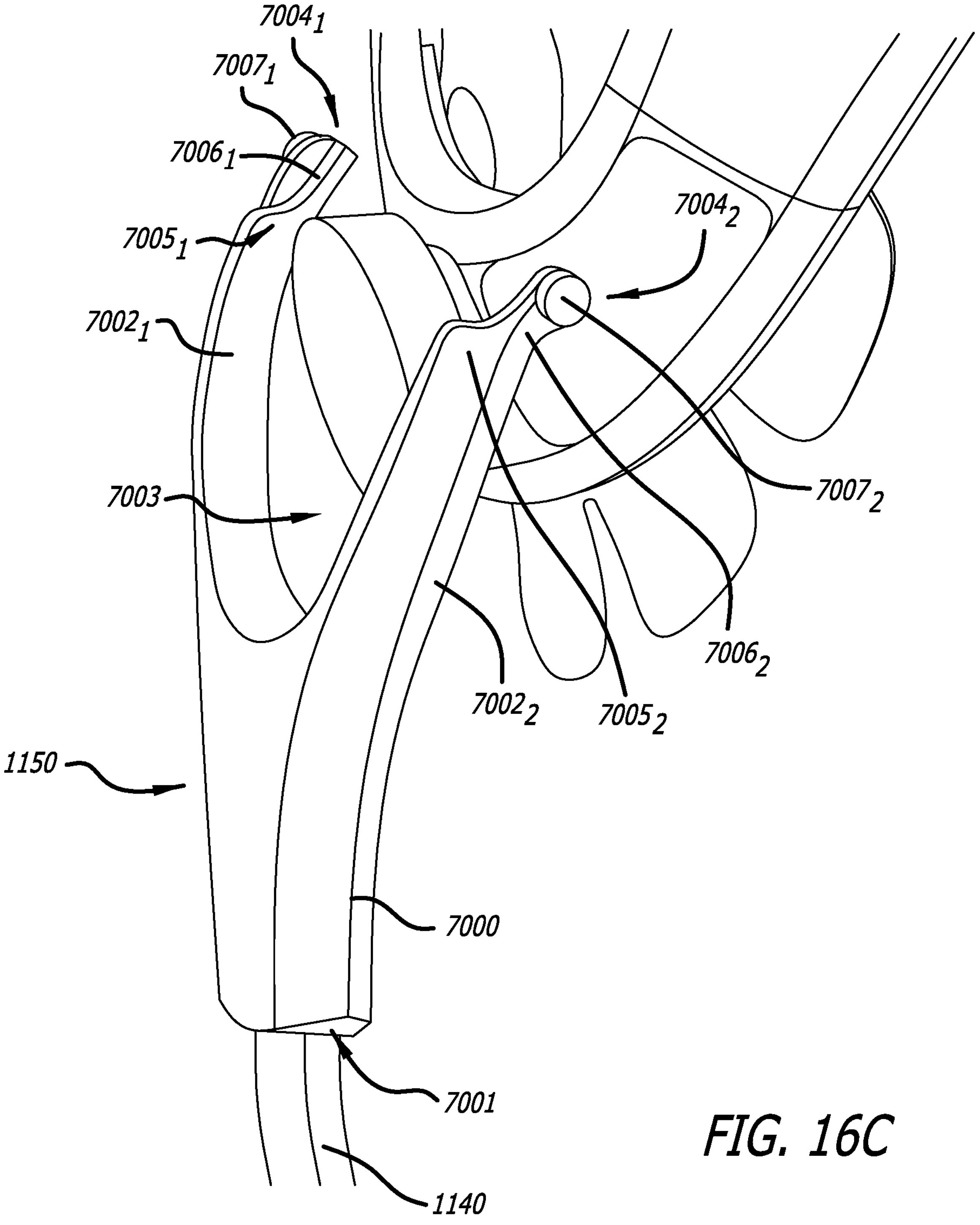
FIG. 16C is a side perspective view of the wishbone extension coupler coupling the extension rod and the CTO clip coupled to the cervical brace of FIG. 16A.

In FIGS. 10A-15C, an anterior bracing system 1100 was illustrated and described detailing the inclusion of an anterior panel and telescopic lateral panels as well as the operability of the telescopic lateral panels to extend or retract in a lateral or medial direction and be locked into place through the transitioning of locking mechanisms from an open state to a closed state. As a result, the telescopic lateral panels may be locked in a particular sizing configuration. Additionally, many of the FIGS. 10A-15C included an extension rod extending in a superior distal direction from the anterior panel where the distal end of the extension includes a wishbone coupler that was coupled to either a support chest plate or a cervical thoracic orthosis (CTO) clip. FIGS. 16A-16C and the ensuing description detail aspects of the wishbone coupler and the coupling to a CTO clip. However, the coupling of the wishbone coupler to the CTO clip operates in the same manner as coupling the wishbone coupler to a support chest plate (see FIGS. 10A-10D); thus, the discussion below pertaining to the coupling of the wishbone coupler to the CTO clip applies equally to the coupling of the wishbone coupler to the support chest plate.

Referring now to FIG. 16A, a front right side perspective view of a wishbone (extension) coupler 1150 coupling the extension rod 1140 and a cervical thoracic orthosis (CTO) clip 7100 coupled to a cervical brace is shown in accordance with some embodiments. A distal end of the extension rod 1140 is shown coupled with the wishbone coupler 1150, which is rotatably coupled to the CTO clip 7100. The CTO clip 7100 is in turn coupled to a cervical collar 200 (e.g., a cervical brace), and specifically to a chest support brace 202. The cervical collar 200 further comprises a front cervical collar portion 204.

The extension rod 1140 may be coupled to the wishbone coupler 1150 through insertion of a distal end of the extension rod 1140 into a receiving cavity 7001 positioned at a bottom (inferior) end of the wishbone coupler 1150. The extension rod 1140 may be retained within the receiving cavity 7001 through interconnections of one or more latches or notches (not shown).

The wishbone coupler 1150 includes a body portion 7000, the receiving cavity 7001, and extension arms $\mathbf{7002}_{1\text{-}2}$ (collectively, extension arms 7002) extending distally in a superior direction from the body portion 7000. As shown, the extension arms 7002 form a wishbone shape in which the extension arms 7002 each extend distally in the superior direction at slightly opposing angles relative to the midline of the wishbone coupler 1150. This architecture has the effect of creating an opening 7003 between the extension arms 7002. The extension arms 7002 terminate at distal ends $\mathbf{7004}_{1\text{-}2}$ (collectively, distal ends 7004) and also include distal ridges $\mathbf{7005}_{1\text{-}2}$ (collectively, distal ridges 7005) as well as distal connection limbs $\mathbf{7006}_{1\text{-}2}$ (collectively, connection limbs 7006), where connection knobs $\mathbf{7007}_{1\text{-}2}$ (collectively, connection knobs 7007) are disposed at the terminal end of the distal connection limbs $\mathbf{7006}_{1\text{-}2}$ (see FIG. 16C).

In coupling the wishbone coupler 1150 to the CTO clip 7100, the distal connection limbs 7006 extend into the receiving components $\mathbf{7106}_{1\text{-}2}$ of the CTO clip 7100. FIG. 16A illustrates an anterior side of the CTO clip 7100, which includes a body portion 7102 formed from first and second extensions $\mathbf{7104}_{1\text{-}2}$ (collectively, first and second extensions 7104) and a lower support portion 7112. The first and second extensions 7104 include the first and second receiving components $\mathbf{7106}_{1\text{-}2}$ (collectively, receiving components 7106), which are configured to receive the connection limbs 7006 and house the connection knobs 7007. The receiving components 7106 include cavities $\mathbf{7108}_{1\text{-}2}$ (collectively, cavities 7108) and slots $\mathbf{7110}_{1\text{-}2}$ (collectively, slots 7110).

The CTO clip 7100 also includes upper ridges 7105$_{1-2}$ (collectively, upper ridges 7105) which couple with an upper portion of the chest support brace 202 of the cervical collar 200, with is also shown in FIG. 16B. Referring to FIG. 16B, a rear perspective view of the wishbone extension coupler coupling the extension rod and the CTO clip coupled to the cervical brace of FIG. 16A is shown in accordance with some embodiments. Posterior notches 7114$_{1-2}$ extend from the upper ridges 7105 and grip a posterior side of the chest support brace 202. Additionally, a lower posterior clip 7115 of the CTO clip 7100 is shown where lower bridge portions 7117$_{1-2}$ couple the lower posterior clip 7715 to the anterior side 7113 of the CTO clip 7100 as shown in FIG. 16A. An aperture 7116 may be formed between the lower bridge portions 7117$_{1-2}$ and be configured to receive a tongue portion 206 of the CTO clip 7100.

Referring to FIG. 16C, a side perspective view of the wishbone extension coupler coupling the extension rod and the CTO clip coupled to the cervical brace of FIG. 16A is shown in accordance with some embodiments. FIG. 16C provides an illustration of the wishbone coupler 1150 adjacent to the cervical brace (cervical collar) 200. As noted above, FIG. 16C provides an illustration of the distal ends 7004 of the extension arms 7002, which include the distal ridges 7005, the connection limbs 7006, and the connection knobs 7007.

Figure 16D:
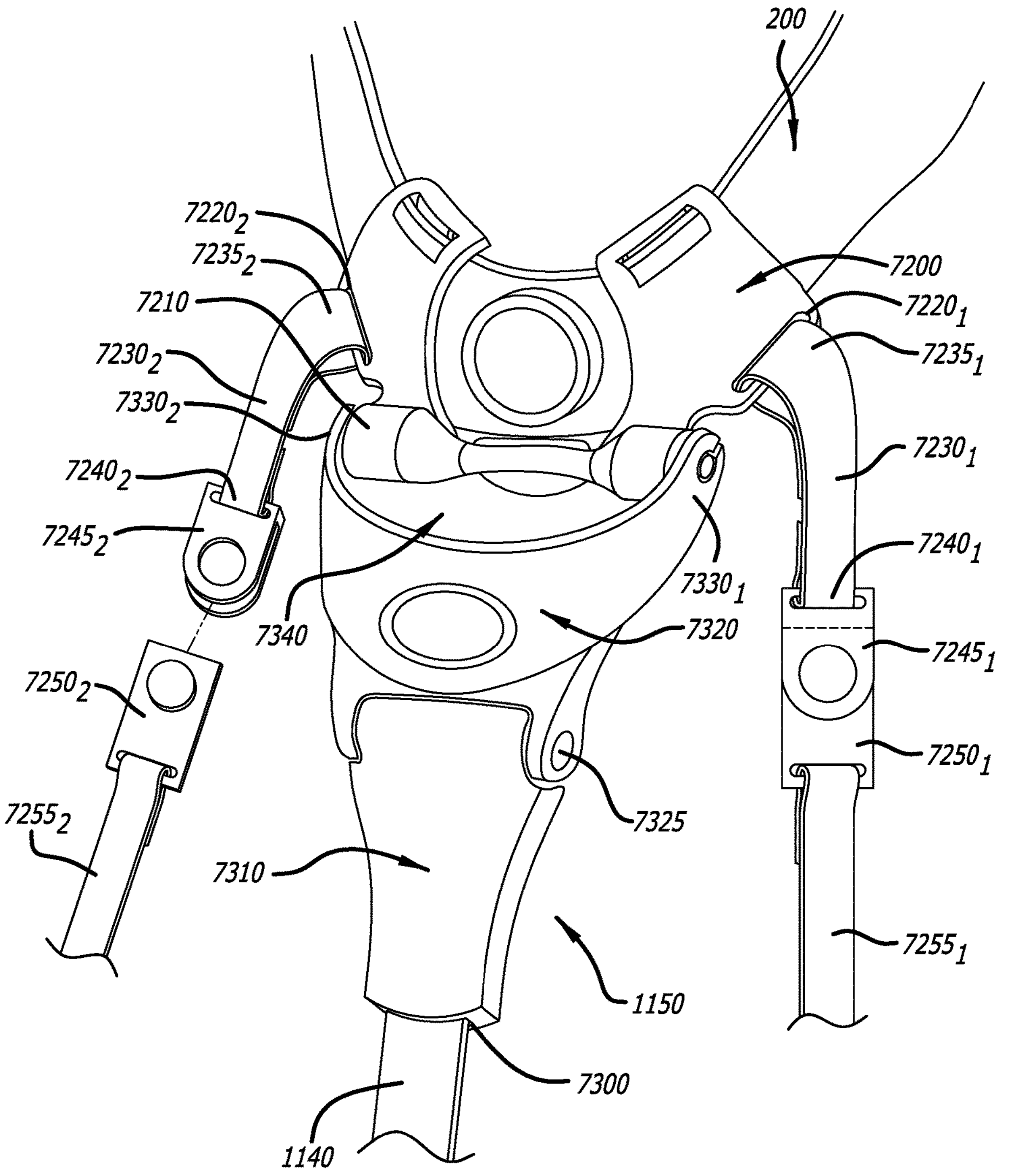
FIG. 16D is a front perspective view of a second embodiment of the wishbone extension coupler and its coupling to a CTO clip.

Referring now to FIG. 16D, a perspective view of a second embodiment of the wishbone coupler 1150 coupling the extension rod 1140 and a cervical thoracic orthosis (CTO) clip 7200 coupled to a cervical brace is shown in accordance with some embodiments. A distal end of the extension rod 1140 is shown coupled with the wishbone coupler 1150, which is rotatably coupled to the CTO clip 7200. The CTO clip 7200 is, in turn, coupled to a cervical collar 200 (e.g., a cervical brace).

The extension rod 1140 may be coupled to the wishbone coupler 1150 through insertion of a distal end of the extension rod 1140 into a receiving cavity 7300 positioned at a bottom (inferior) end of the wishbone coupler 1150. The extension rod 1140 may be retained within the receiving cavity 7300 through interconnections of one or more latches or notches (not shown).

The wishbone coupler 1150 includes a first body portion 7310, a second body portion 7320 rotationally coupled to the first body portion 7310 by hinge 7325 oriented with a substantially horizontal rotational axis, and extension arms 7330$_{1-2}$ (collectively, extension arms 7330) extending distally in a superior direction from the second body portion 7320. As shown, the extension arms 7330 form a wishbone shape in which the extension arms 7330 each extend distally in the superior direction at slightly opposing angles relative to the midline of the wishbone coupler 1150. This architecture has the effect of creating an opening 7340 between the extension arms 7330. The extension arms 7330 terminate at distal ends 7335$_{1-2}$ (collectively, distal ends 7335), which is adapted to be rotationally coupled to a coupling member 7210 of the CTO clip 7200.

For coupling the wishbone coupler 1150, the CTO clip 7200 also includes a first set of fastening members 7220$_{1-2}$ (collectively, fastening members 7220). As an illustrative example, the fastening members 7220 may constitute "D-ring" fasteners that are integrated as part of the CTO clip 7200. The D-ring fasteners 7220$_{1-2}$ are configured to receive first support straps 7230$_{1-2}$, where each of the first support straps 7230$_{1-2}$ includes a first end portion 7235$_{1-2}$ and a second end portion 7240$_{1-2}$. More specifically, the first end portion 7235$_1$ of the first support strap 7230$_1$ is securely attached to the D-ring fastener 7220$_1$. This attachment may be accomplished though complementary hook and loop fasteners (UBL material) positioned along opposite surfaces at the first end portion 7235$_1$ after insertion through the D-ring fastener 7220$_1$. A similar arrangement may occur between the D-ring fastener 7220$_2$ and the second end portion 7235$_2$ of the first support straps 7230$_2$.

As further shown in FIG. 16D, a distal part of each of the second end portions 7240$_{1-2}$ includes a bracket 7245$_{1-2}$, which is to be fastened to a complementary bracket 7250$_{1-2}$ oriented on a distal end of second support strap 7255$_{1-2}$, respectively. More specifically, the bracket 7245$_1$ of the first support strap 7230$_1$ is securely attached to the complementary bracket 7250$_1$ of the second support strap 7255$_1$. Similarly, the bracket 7245$_2$ of the second support strap 7230$_2$ is securely attached to the complementary bracket 7250$_2$ of the second support strap 7255$_2$. The support straps 7255$_{1-2}$ may extend under the axilla of the wearer.

V. Lateral Panel Lockout

Figure 17A:
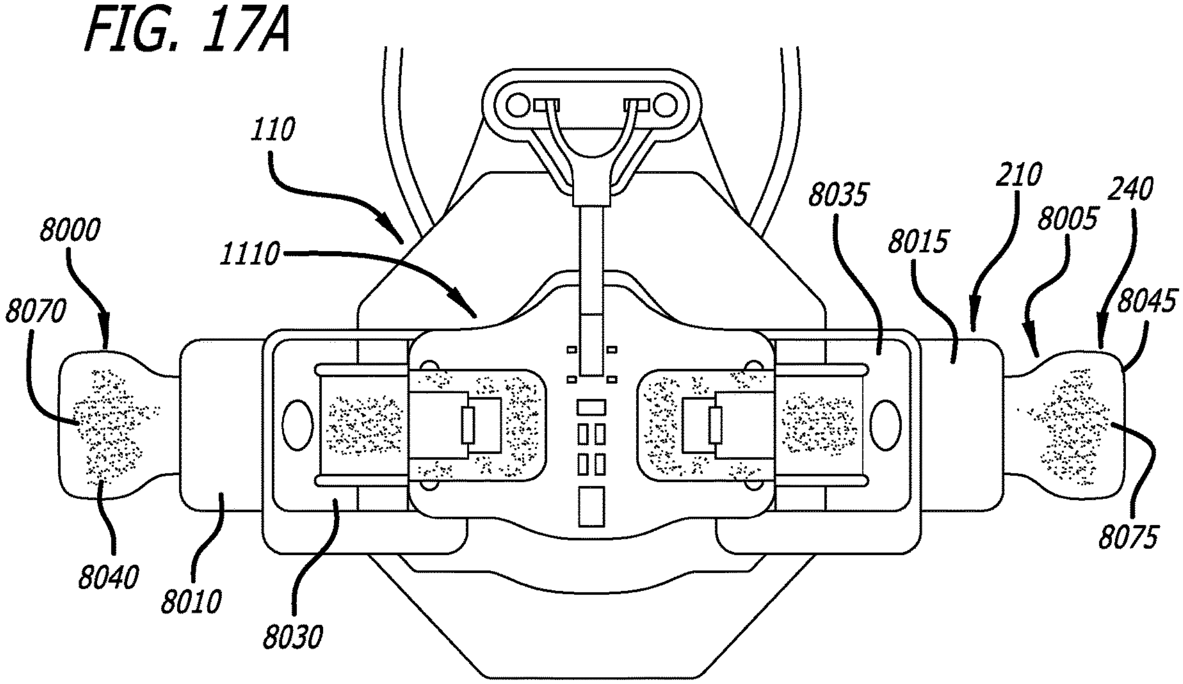
FIGS. 17A-17D are exemplary embodiments illustrating a lateral panel lockout process to restrict removal of the orthopedic brace to a selected side.

As shown in FIG. 17A, the connectivity between the posterior bracing system 110 and the anterior bracing system 1110 is partially accomplished through the belt members 240 (e.g., a first belt member 8000 and a second belt member 8005) attached to the telescopic lateral panels 210 (e.g., a first lateral panel 8010 and a second lateral panel 8015) and support straps 8020 extending between these bracing systems 110 and 1110. More specifically, as further shown in FIGS. 17A-17B, after extending the belt members 8000/8005 and telescopic lateral panels 8010/8015 of the posterior bracing system 110 to a desired length (sizing), the telescopic lateral panels 8010 and 8015 may be partially wrapped (normally around a waist area of the wearer) and at least partially overlay the extended lateral panels 8030 and 8035 of the anterior bracing system 1110. In particular, the telescopic lateral panels 8010 and 8015 would extend and bend with a curvature to remain adjacent to a side of the wearer after attachment of the anterior bracing system 1110. A first portion for each of the belt members 240 extends from the pulley subsystem and overlays its corresponding lateral panel as shown in FIG. 4C. A second portion 8040/8045 for each of the belt members 8000/8005 extends beyond to overlay the conformed lateral panels 8030 and 8045 of the anterior bracing system 1110 for attachment to a front surface 8050 of the anterior panel 1120. This attachment may be accomplished by a loop and hook fastener with unbroken loop (UBL) fabric 8060 placed on the front surface 8050 of the anterior panel 1120 and rear surfaces 8070/8075 of the second portions 8040/8045 for the belt members 8000/8005 include hooks for attachment to the UBL fabric 8060.

Figure 17B:
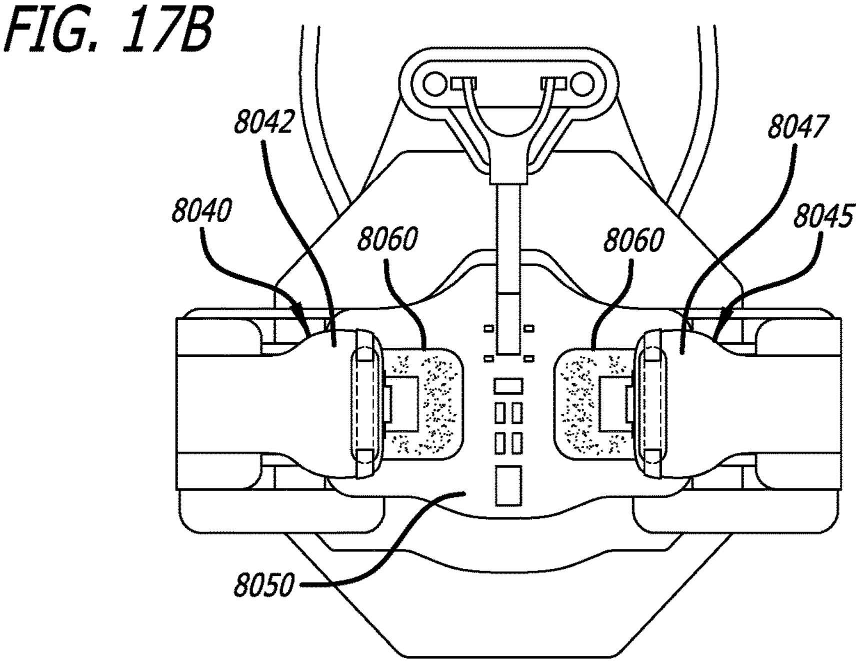
Figure 17C:
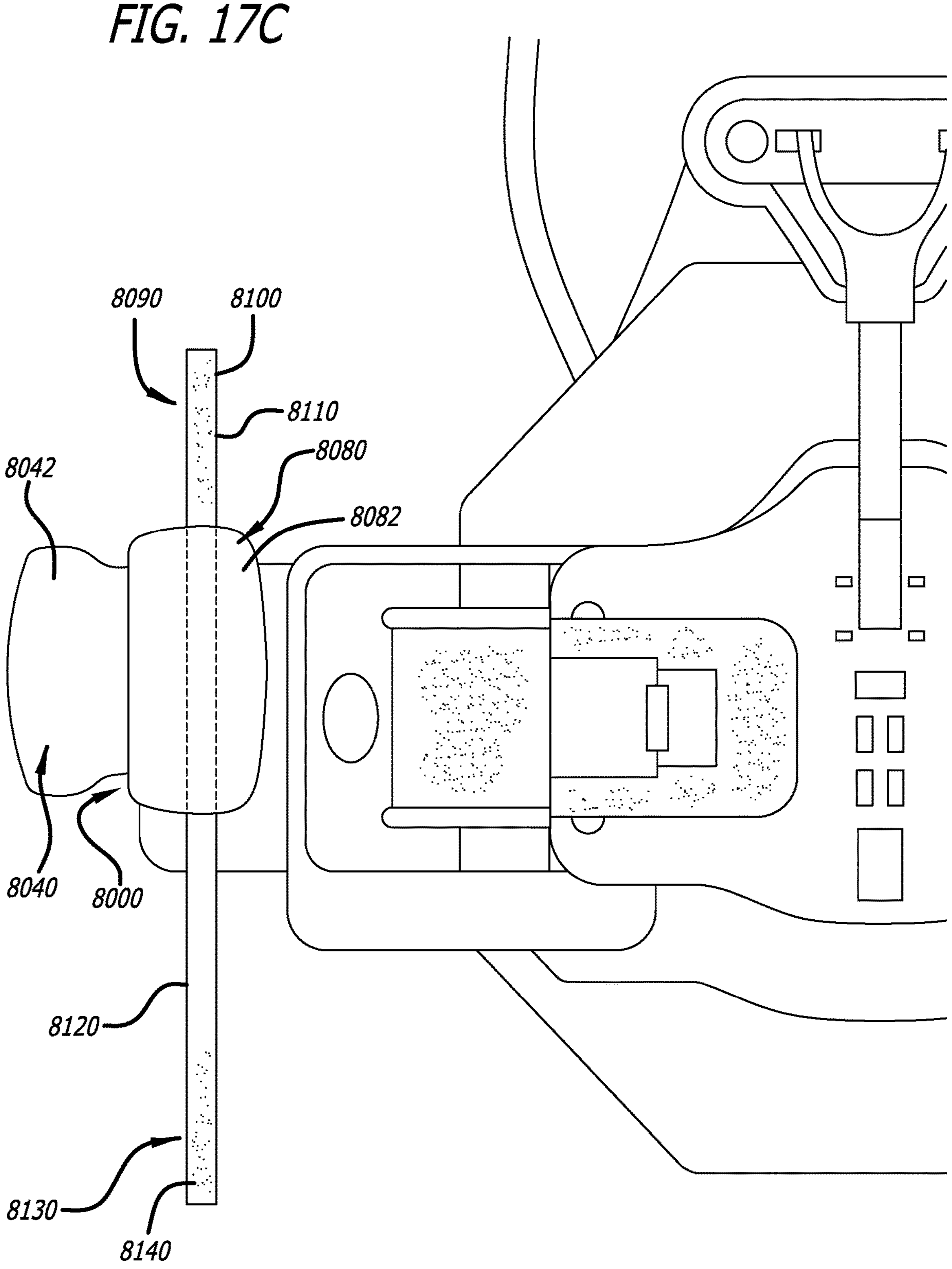

According to one embodiment of the disclosure, each of the second portions 8040/8045 of the belt members 8000/8005, notably distal ends 8042/8047 of the second portions 8040/8045 of the belt members 8000/8005, includes a rigid portion 8080 that is oriented widthwise (longitudinally). For example, as shown in FIG. 17C, a rigid portion 8080 are inserted under fabric 8082 covering the distal end 8042 of the second portion 8040. A first guide straps 8090 is integrated as part of the fabric 8082 at the distal end 8042 included as part of the second portion 8040 of the first belt member 8000. The first guide strap 8090 is oriented longitudinally from the integrated rigid portion 8080 to form a loop construction when the first guide strap 8090 is placed into a first operational state as shown in FIG. 17B. Although not shown in detail, the same construction is applied to the second belt member 8005 as shown in FIG. 17B.

Referring back to FIG. 17C, the first guide strap 8090 includes a hook fastener 8100 positioned on a first surface 8110 (rear-facing surface) for attachment to UBL fabric 8120 deployed over a first (front-facing) surface 8130 of a second guide strap 8140 to form a loop extending from the front surface 8050 of the anterior panel 1120.

Figure 17D:
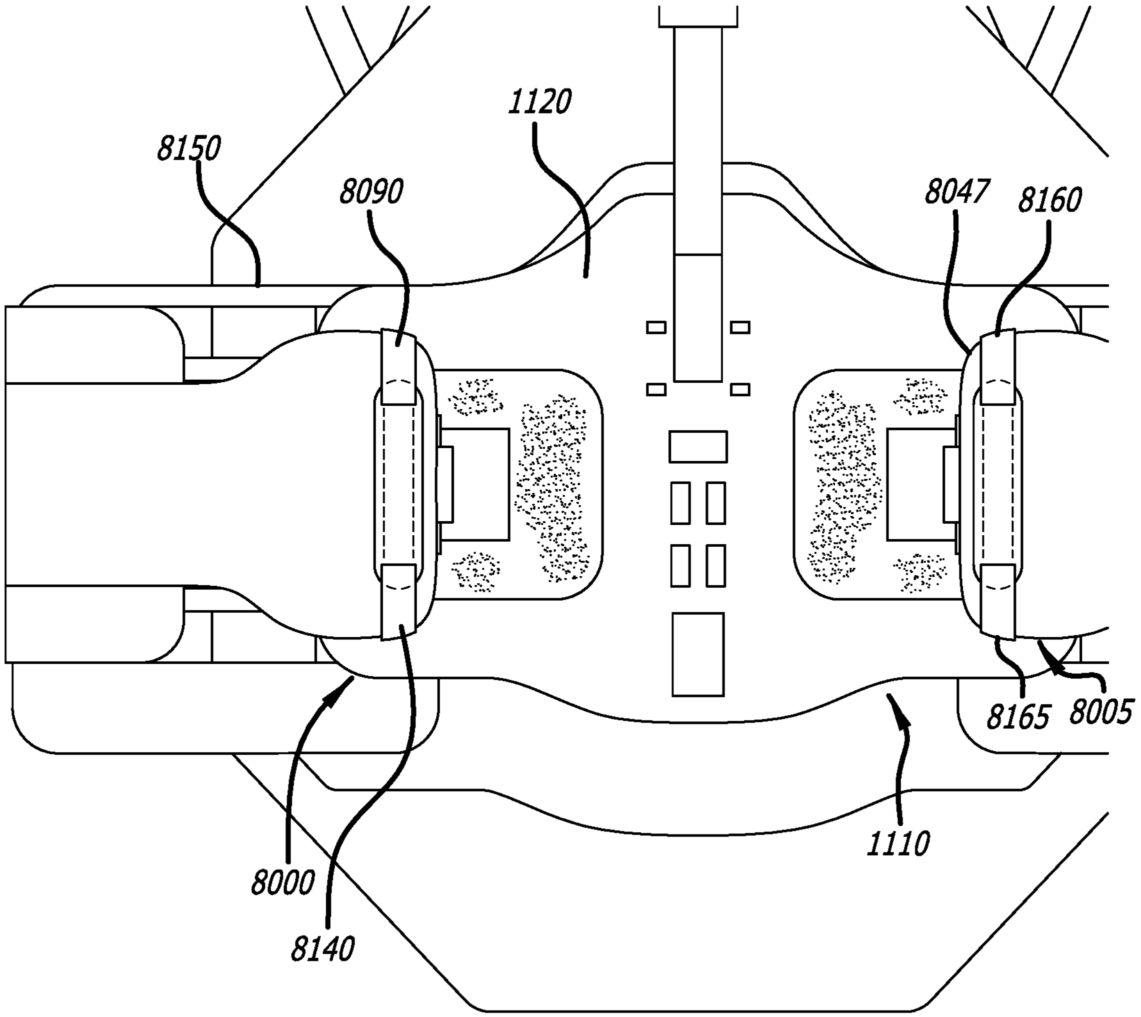

Herein, the first and second guide straps 8090/8140 may be disconnected and placed into a second operational state. In this state, in lieu of being connected together to form a loop accessible by the wearer (or a third party) and positioned on the front surface 8050 of the anterior panel 1120 as shown in FIG. 17D, the first and second guide straps 8090/8140 may be disconnected, wrapped around an edge portion 8150 of the anterior panel 1120 of the anterior bracing system 1110, and the hook fastener 8100 of the first guide strap 8090 is securely attached to the UBL fabric 8120 deployed on the second guide strap 8140 (not shown). As a result, the belt member 8000 is connected to the anterior panel 1120 and the wearer is prevented from existing the orthopedic brace by disengaging this belt member 8000 from the anterior panel 1120. Instead, the second belt member 8005 remains in the first operational state by being attached to the UBL fabric 8060 on the front surface 8050 of the anterior panel 1120. As a result, by grabbing a loop handle formed by guide straps 8160 and 8165 located on the distal end 8047 of the second belt member 8005, the wearer may be able to disengage the second belt member 8005 from the anterior panel 1120 to allow a side opening for the wearer to remove the orthopedic brace.

VI. Support Strap Configuration

Figure 18A:
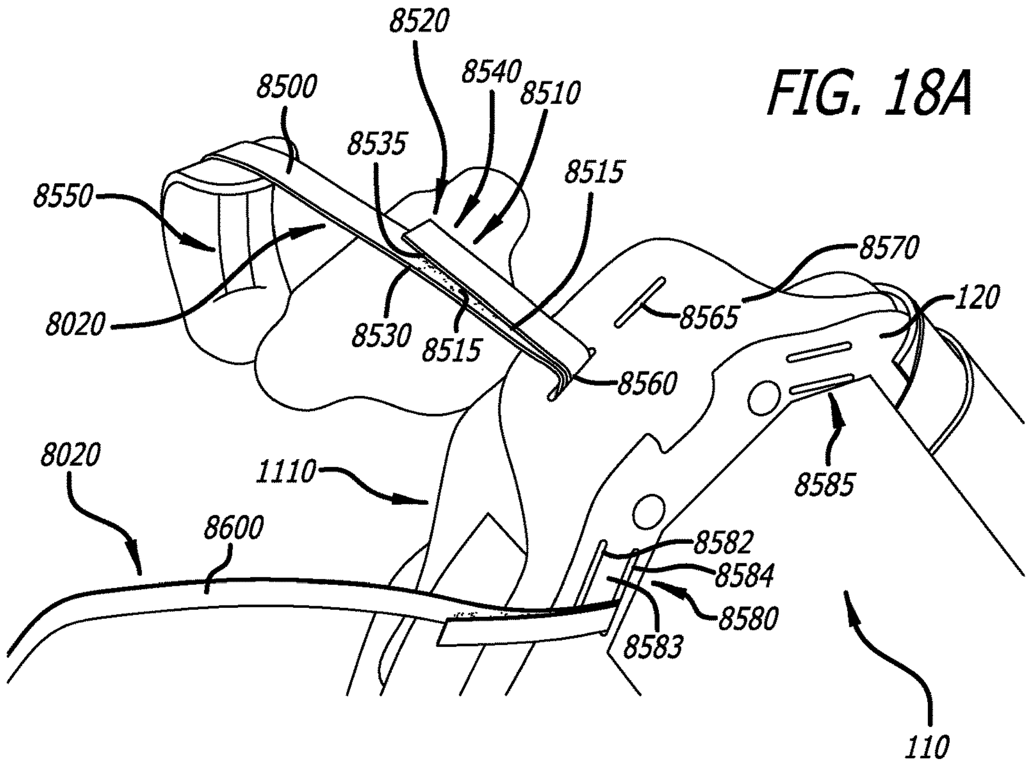
FIGS. 18A-18B are exemplary embodiments of a support strap configuration for interconnecting the posterior bracing system of FIGS. 1-9 to the anterior bracing system of FIGS. 10A-16C.
Figure 18B:
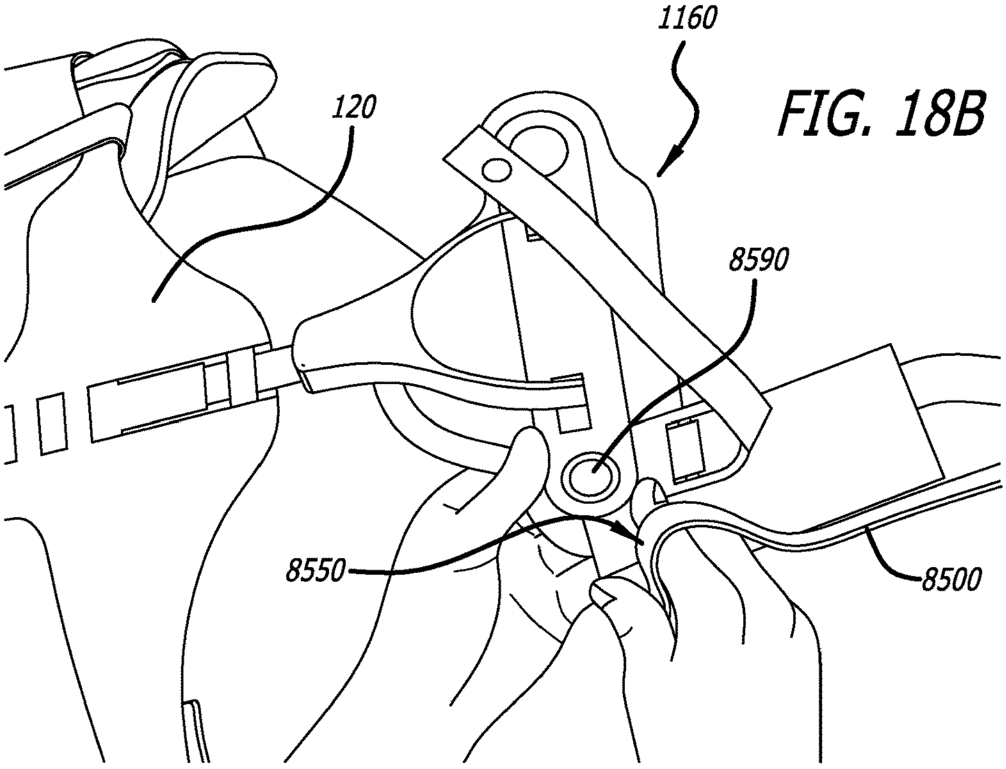

Referring to FIGS. 18A-18B, the connectivity between the posterior bracing system 110 and the anterior bracing system 1110 is also accomplished through the support straps 8020 such as a first set of support straps (e.g., first support strap 8500) and a second set of support straps (e.g., a second support strap 8600) as shown. The first support strap 8500 may be deployed over a shoulder of the wearer, where the first support strap 8500 illustrates a deployment utilizing a strap slot 8560 of an extension panel 8570, albeit the strap guide 8580 may be used as the anchoring point for the first support strap. Although not shown, another support strap belonging to the first set of support straps may be anchored by a strap slot 8565 or a strap guide 8585 as shown in FIG. 18A. Similarly, the second support strap 8600 may be deployed under an axilla of the wearer. Herein, the first support strap 8500 is illustrative of deployment of the first set of support straps and the second support strap 8600 is illustrative of deployment of the second set of support straps.

In particular, as shown in FIG. 18A, the first support strap 8500 includes a first end segment 8510 and a second end segment 8550. The first end segment 8510 may include a hook and loop fastening system 8520. For example, a loop fastener 8530 may be positioned on a first surface 8515 (e.g., upward facing surface) of the first end segment 8510 as shown in FIG. 18A, and a hook fastener 8535 may be positioned on the first surface 8515 at a distal end 8540 of the first end segment 8510. Hence, after the distal end 8540 of the first end segment 8510 is inserted through either (i) the strap slot 8560 (e.g., equivalent to strap slots 755/765 of FIG. 7A) positioned within the extension panel 8570 of the posterior bracing system 110 or (ii) one of the opening 8582/8584 of the strap guide 8580 (e.g., equivalent to strap guide 136 of FIG. 7A) in the posterior panel 120 and folded back, the hook fastener 8535 may be affixed to the loop fastener 8530. This connects the first support strap 8500 to the posterior bracing system 110. As shown in FIG. 18B, the second end segment 8550 includes a buckle 8590 positioned at a distal end of the second end segment 8550 for attachment to the support chest plate 1160 of FIG. 10A. Multiple buckles may be connected simultaneously to each snap connector 1167 on the support chest plate 1160.

More specifically, for connecting the first support strap 8500 between the posterior bracing system 110 and the anterior bracing system 1110, the first end segment 8515 is arranged to be secured by one or more strap holding members (e.g., the strap slot 8560 in the extension panel 8570 or the strap guide 8580 in the posterior panel 120) for positioned the first support strap 8500 over the wearer's shoulder. According to one embodiment of the disclosure, the strap holding member may include a single slot (e.g., the strap slot 8560) formed toward a top portion of the extension panel 8570 in which the distal end 8540 of the first end segment 8510 of the first support strap 8500 may be inserted from an anterior side to a posterior side of the strap slot 8560 and looped back over the top portion of the extension panel 8570 as shown. The distal end 8540 of the first end segment 8510 is attached to another portion of the first end segment 8510 to create a looped end fastened to the extension panel 8570.

Alternatively, although not shown, the first support strap 8500 may be coupled to the strap guide 8580 formed within a top portion of the posterior panel 110 with a member 8583 positioned to span across an opening to create the first opening 8582 and the second opening 8584. The first and second openings 8582/8584 are aligned with a strap slot (not shown) located toward a bottom portion of the extension panel, where the strap slot has an opening of an area that would allow the first support strap 8500 to be inserted into and returned from the strap slot, if desired. As an illustrated example, as illustrated with the second support strap 8600, a distal end of that support strap may be inserted through the second opening 8584 of the strap guide 8580 and attached to a loop fastener directly or looped back through the first opening 8582 of the strap guide 8580. As a result, the member 8583 is configured as a termination point for a first end segment of a support strap, where a single opening 8582 or 8584 may be used as the attachment point for the support strap (where multiple openings are provided for sizing) or both openings 8582 and 8584 may be used with the member 8583 operating as the attachment point.

As shown in FIGS. 18A-18B, where a first set of support straps (e.g., first support strap 8500 and a complementary support strap (not shown) are coupled to the strap slots 8560 and 8562 formed towards the top portion of the extension panel 8570, one or more support straps (e.g., second support strap 8600) may be coupled to the above-described strap guides 8580 and/or 8585 to extend between the posterior bracing system 110 and the anterior bracing system 1110 under the axilla of the wearer. This provides additional immobility of the orthopedic brace.

VII. Donning Method for Orthopedic Brace—Sizing

Referring to FIGS. 19A-19I, a first illustrative embodiment of the donning process for placement of the orthopedic brace onto a wearer is shown. Herein, as shown in FIGS. 19A-19D, each of the belt members (e.g., the second belt member 8005 of FIG. 17A) may be sized in accordance with an internal (or optionally external) sizing process as described in FIGS. 6A-6D. This sizing process (FIGS. 19A-19E) may be optional, as the posterior bracing system 110 may be sized prior to the orthotist commencing the donning process or the posterior bracing system 110 may be manufactured and sized to fit a majority of the patients without adjustment of the posterior belt where the sizing differences of the patients may be accommodated through the anterior bracing system 1110.

Herein, according to one embodiment of the disclosure, in accordance with the internal sizing process, a first portion 9000 for each of the belt members (e.g., the second belt member 8005 of FIG. 17A) includes an end portion 9005 that is threaded through the belt slot $\mathbf{156_2}$ of a pulley base $\mathbf{154_2}$ of the pulley subsystem and is folded back onto prescribed area on an interior surface 9010 of the belt member 8005. As a result, the end portion 9005 is in direct contact with the telescopic lateral panel 8015. Herein, the end 9005 includes a hook fastener 9020 and the prescribed area features UBL fabric 9025 situated on the interior surface 9020, and the belt member 8005 may be sized through indicia as described above and illustrated in FIGS. 6A-6B.

As shown in FIGS. 19C-19D, according to one embodiment of the disclosure and in accordance with the external sizing process, a first portion 9030 for each of the belt members (e.g., the first belt member 8000 of FIG. 17A) includes an end portion 9035 that is threaded through the belt slot $\mathbf{156_1}$ of a pulley base $\mathbf{154_1}$ of the pulley subsystem. The first portion 9030 is folded back onto prescribed area on an outer surface 9040 of the belt member 8000. As a result, the end portion 9035 is facing away with the telescopic lateral panel 8010 so that, according to one embodiment, the end portion 9035 is positioned immediately posterior to the telescopic lateral panel 8010. The end portion 9035 may be folded on or under the outer surface 9040 of the belt member 8000. This may be accomplished by UBL placed on a substantial portion of the top/bottom surfaces of the belt member 8000.

As shown in FIG. 19E, as an illustrative embodiment, the lateral panels (e.g., lateral panel 8015) may be sized in accordance with indicia (markings) representing sizing of the belt member 8005. As a result, the lateral panel 8015 is removably connected to the belt member 8005. Therefore, upon pulling a handle 9045 attached to both the belt member 8005 and the lateral panel 8015 as show in FIG. 19F, the belt/panel combination 8005/8015 is extended from to its prescribed sizing. Alternatively, a webbing sewn onto the inside of each belt member 8000 or 8005, which is configured to hook into its corresponding lateral panel 8010 or 8015, respectively. Hence, when upon pulling on the end of the belt member (e.g., belt member 8000), the lateral panel (e.g., lateral panel 8010) is pulled with it.

Referring to FIG. 19G, the orthotist adjusts the first and second telescopic lateral panels 1130A, 1130B of the anterior bracing system 1110, where the adjustment may correspond to the sizing selected for the belt members. However, it is contemplated that the sizing selected for the lateral panels 1130A, 1130B may be independent to adjust the tightness of the orthopedic brace to the wearer. The sizing of the lateral panels 1130A, 1130B may be based on the indicia 1137 provided on the lateral panels 1130A, 1130B aligned to a side edge 9050 of the anterior panel 1120.

Figure 19A:
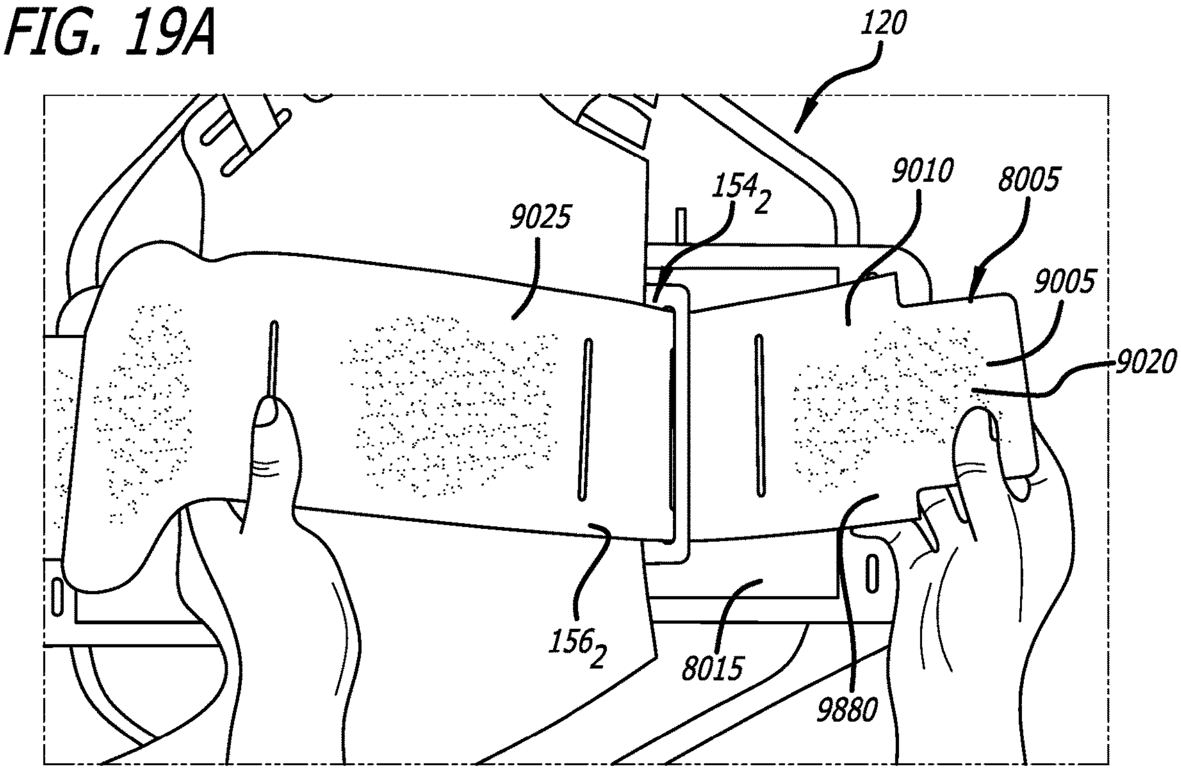
Figure 19B:
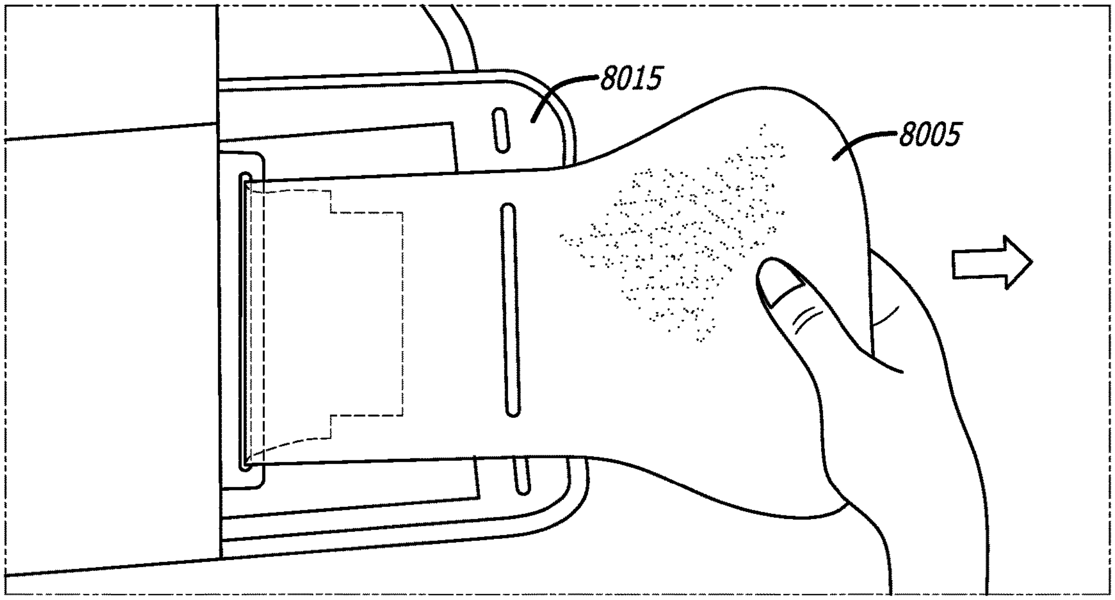
Figure 19H:
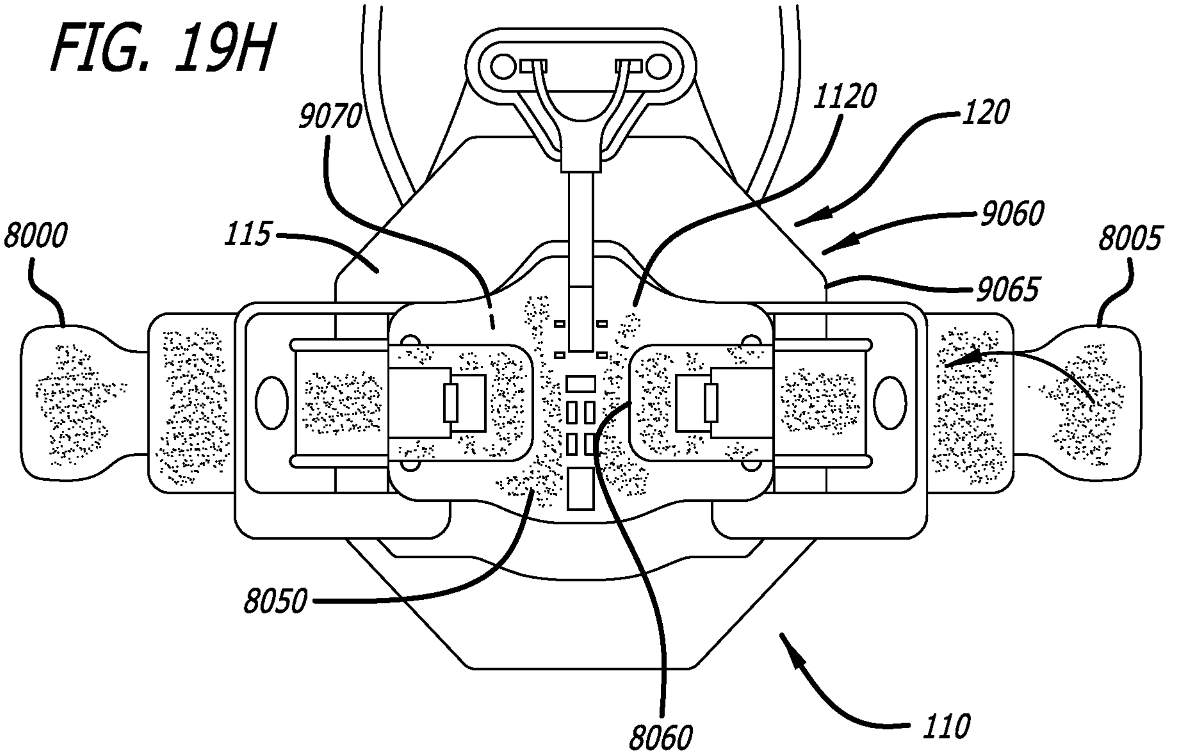
Figure 19I:
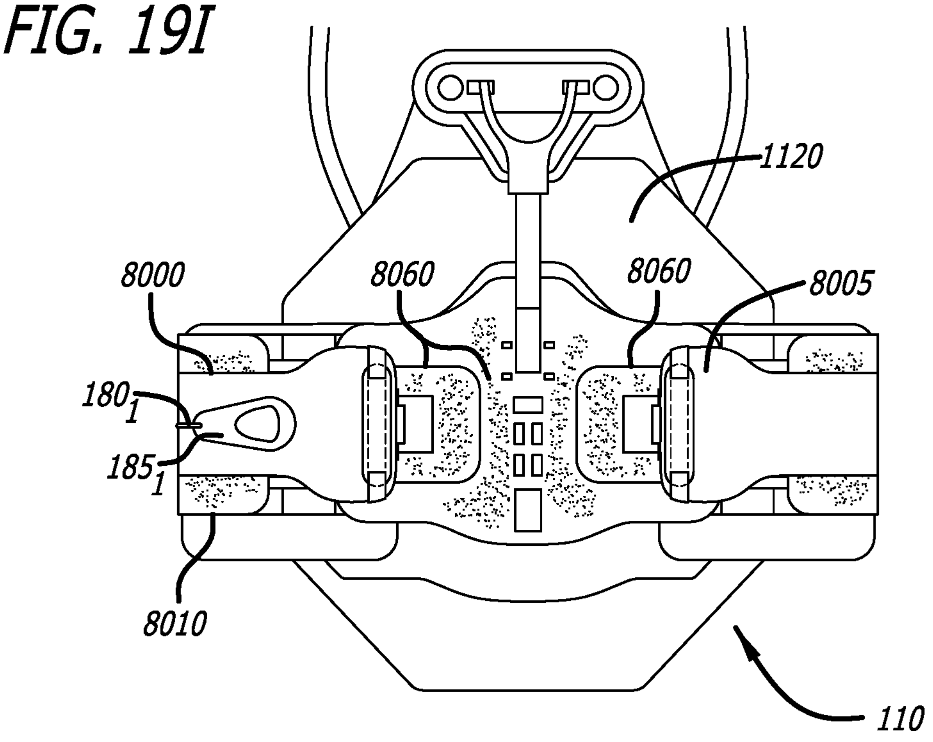

Referring now to FIGS. 19H-19I, the posterior bracing system 110 is arranged with a posterior surface 9060 of the posterior panel 120 rests on a surface (e.g., table, ground, etc.) with the filler 115 (padding) positioned on an anterior surface 9065 of the posterior panel 120. A posterior side 9070 of the anterior bracing system 1110 is positioned to rest on a chest of the wear and facing the anterior surface 9065 of the posterior panel 120. The belt members 8000 and 8005 are moved toward the anterior (front) surface 8050 of the anterior panel 1120 for attachment to the UBL fabric 8060 placed on the front surface 8050 of the anterior panel 1120. Additionally, the handles (e.g., handle $\mathbf{185_1}$) coupled to the pulley subsystem via designated pulley cord (e.g., cord $\mathbf{180_1}$) may be adjusted and attached to the UBL fabric 8060.

VIII. Donning Method for Orthopedic Brace—Fitting

Figure 20A:
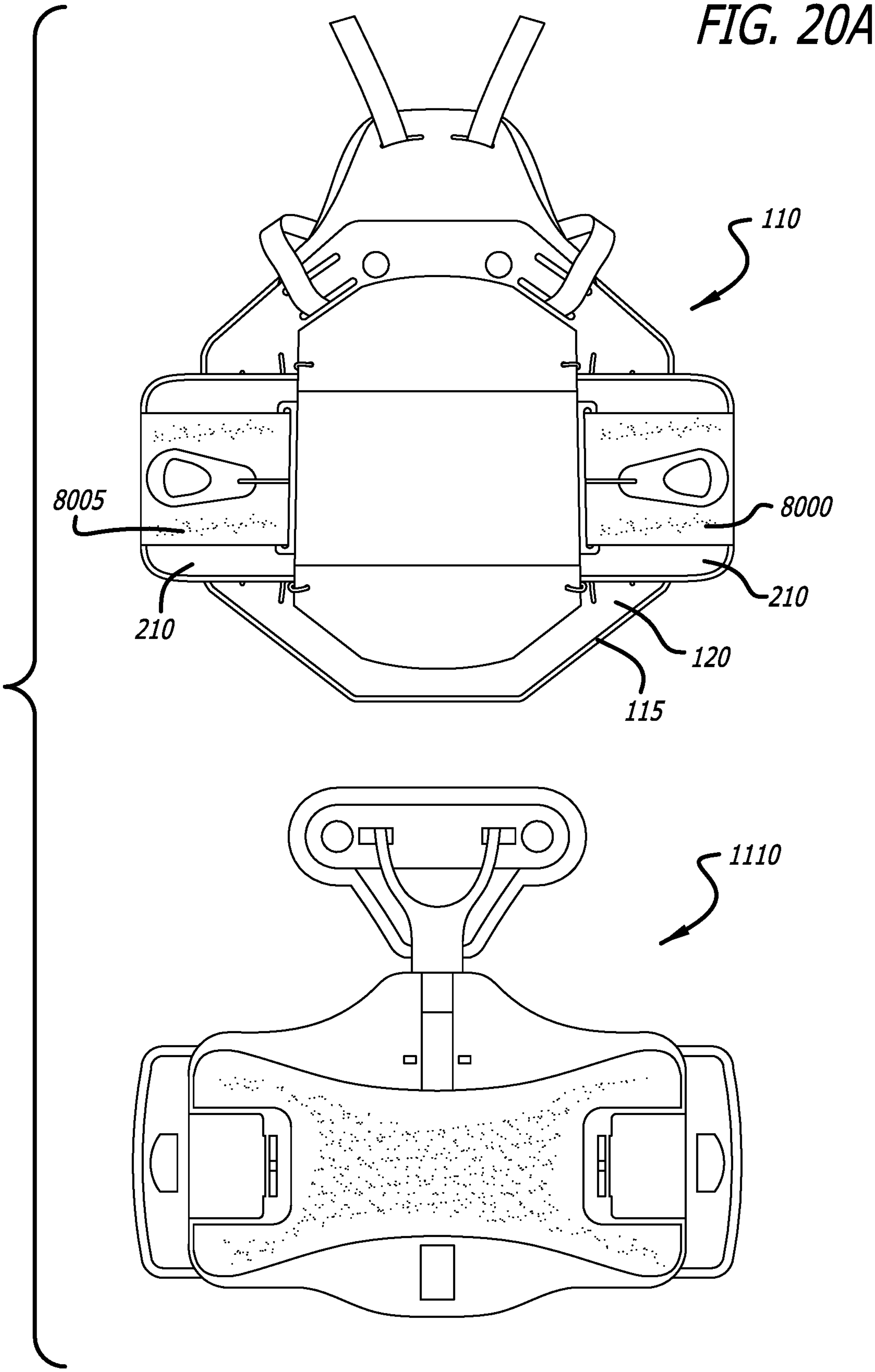
Figure 20B:
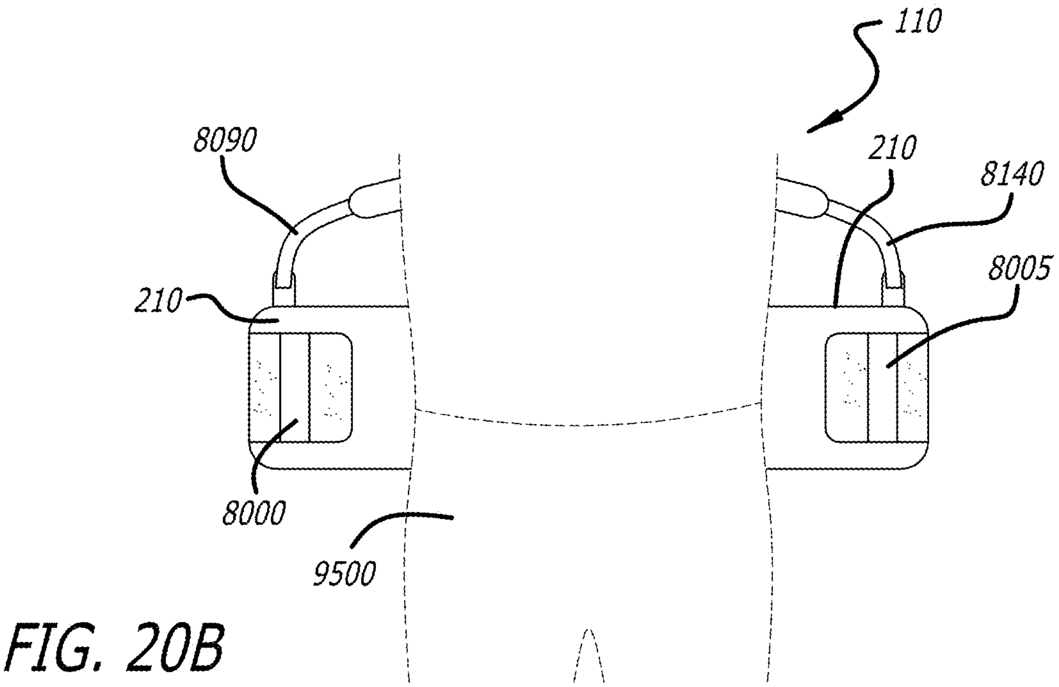
Figure 20C:
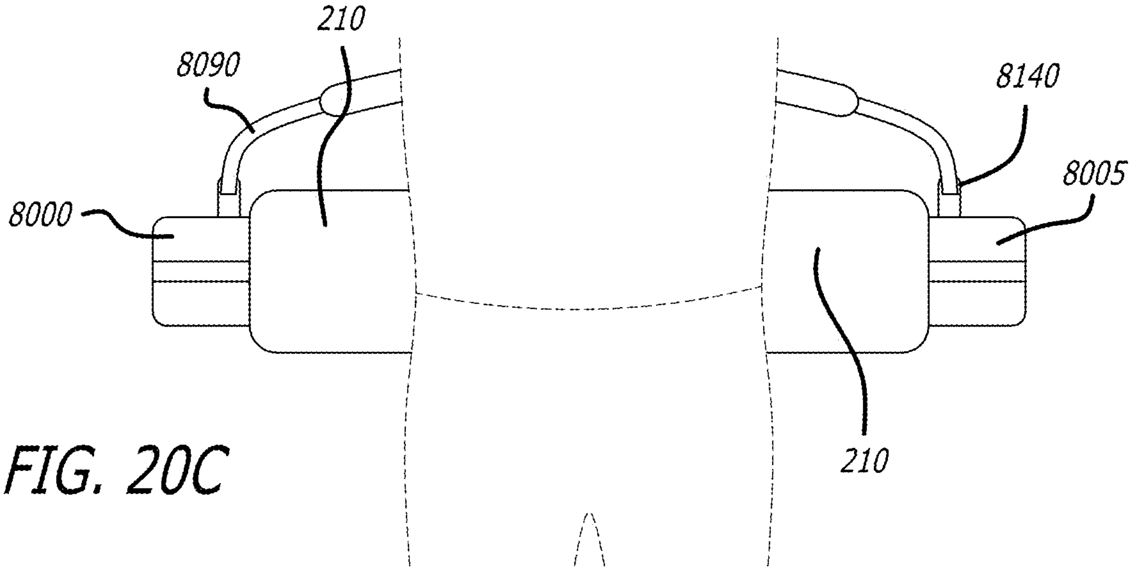
Figure 20D:
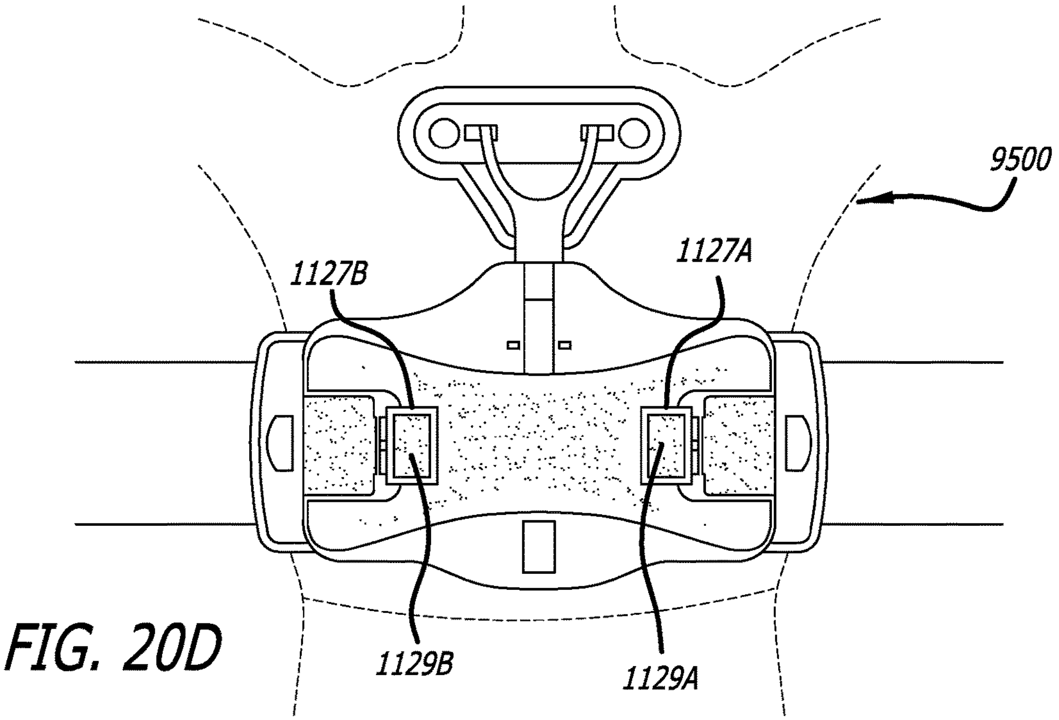
Figure 20E:
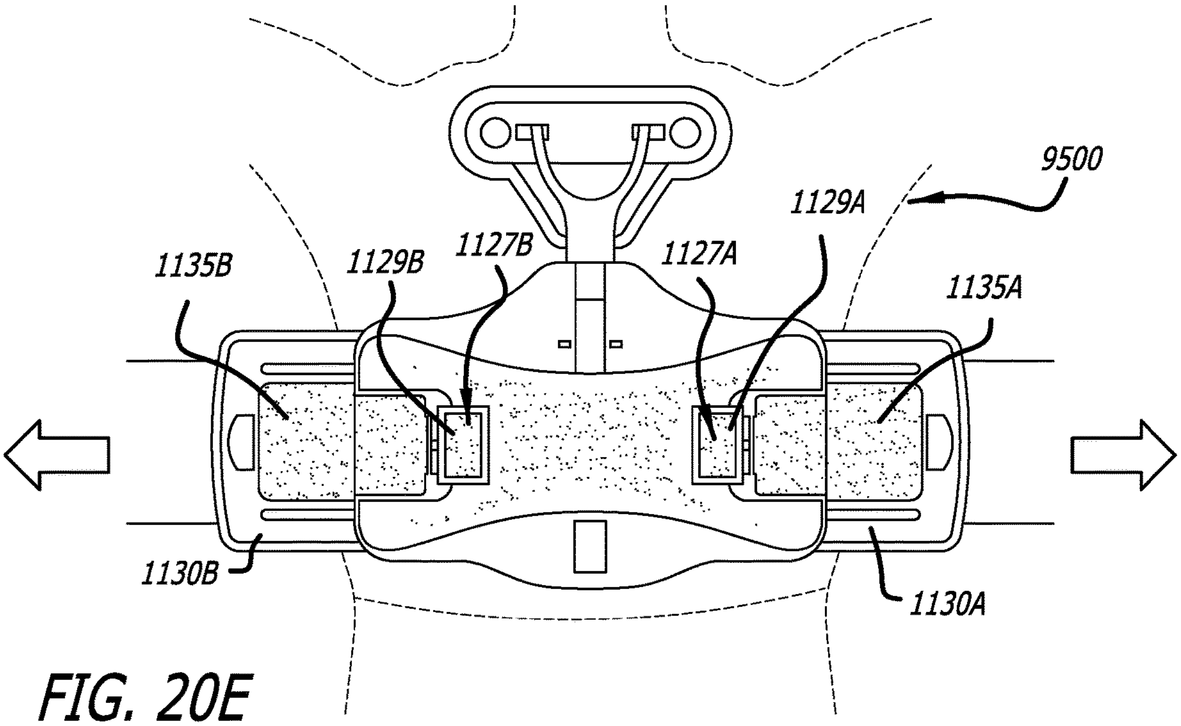
Figure 20H:
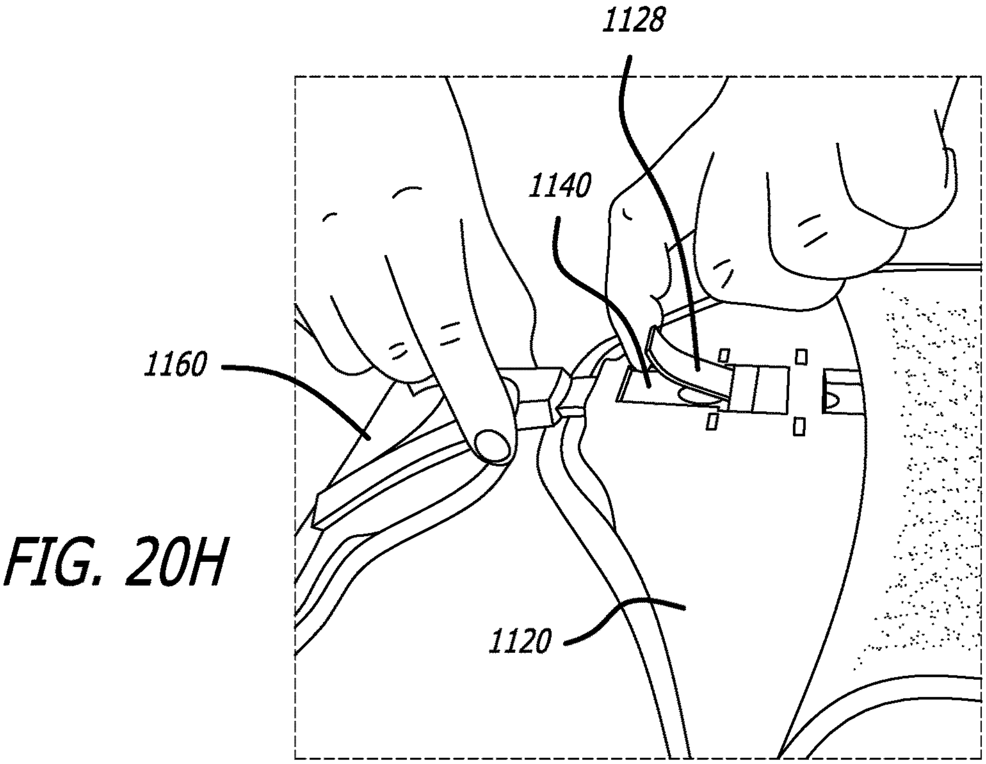
Figure 20I:
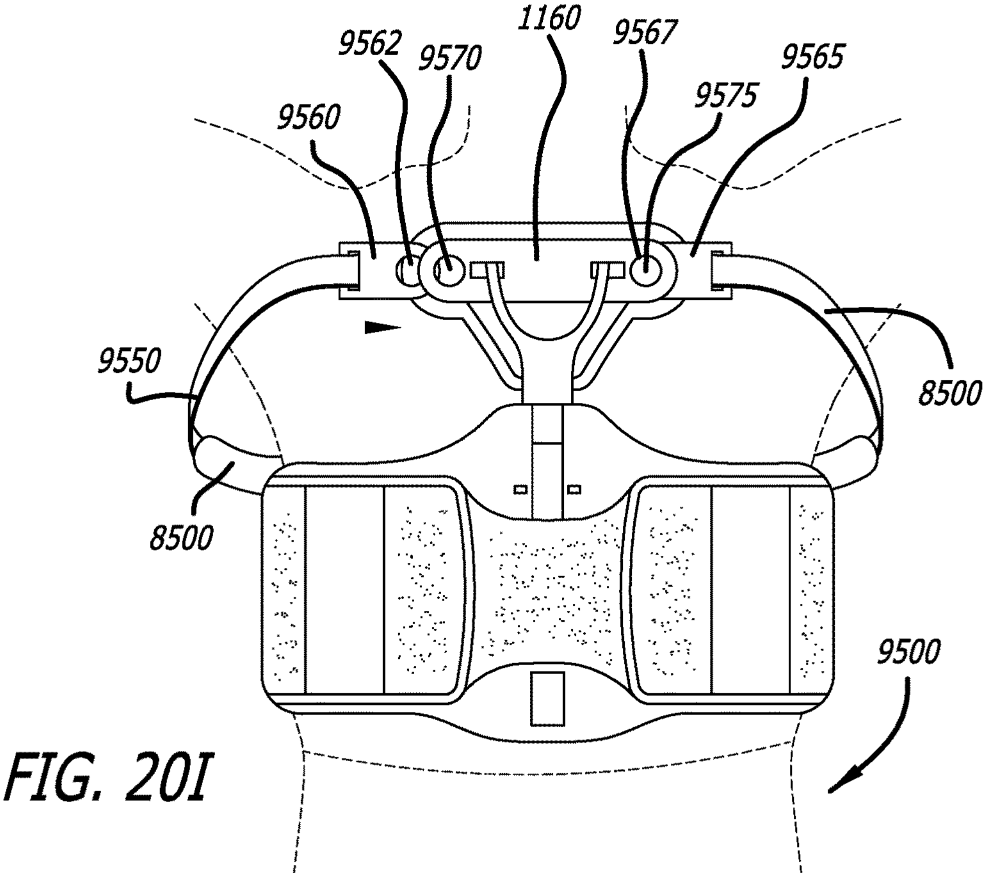
Figure 20J:
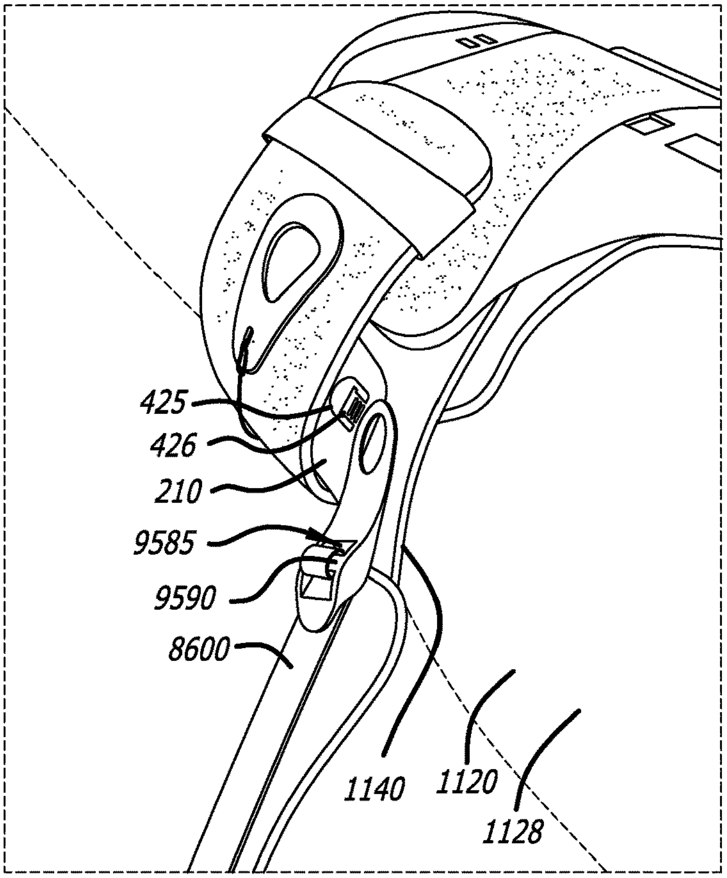
Figure 20K:
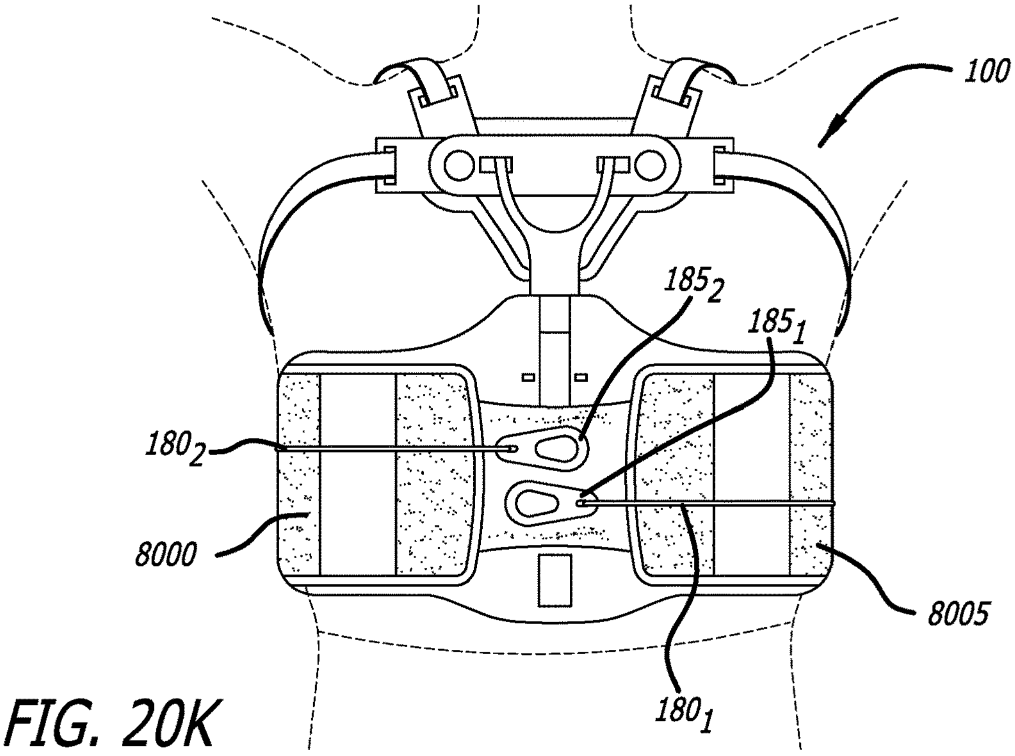

Referring to FIGS. 20A-20K, a second illustrative embodiment of the donning process for placement of the orthopedic brace onto a wearer is shown. Herein, as shown in FIGS. 19A-19I, each of the belt members (e.g., the second belt member 8005 of FIG. 17A) may be sized prior to the orthotist commencing the donning process. As a result, as shown in FIG. 20A, both the posterior bracing system 110 and the anterior bracing system 1110 are available for placement on the wearer.

As shown in FIG. 20B, the wearer 9500 is positioned with her thoracic and lumbar back regions resting on padding 115 placed on an anterior-facing portion of the posterior bracing system 110. The lateral telescopic panels 210 and belt members 8000/8005 of the posterior bracing system 110 are extended from the posterior panel 120 and away from the wearer 9500. This extension may be accomplished by pulling the guide straps 8090/8140 laterally away from the posterior panel 120, where distal ends of the belt members are unfastened from coupling to an anterior side of the lateral telescopic panels 210 (e.g., padding attached to the anterior side of the lateral telescopic panels 210) as shown in FIG. 20C.

Referring now to FIG. 20D, the anterior bracing system 1110 is positioned over an abdomen of the wearer 9500. The fastener 1129A/1129B associated with the locking members 1127A/1127B are detached from complementary fasteners 1135A/1135B positioned on the anterior side of each lateral panel 1130A/1130B. As shown, according to one embodiment of the disclosure, hook fasteners 1129A/1129B are detached from UBL material operating as fasteners 1135A/1135B to place the locking members 1127A/1127B into an unlocked state. In this state, the lateral panel 1130A/1130B may be laterally adjusted.

More specifically, as shown in FIGS. 20E-20F, the first and second telescopic lateral panels 1130A/1130B may be extend laterally and bent to cover a side of the wearer 9500. Once the lateral panels 1130A/1130B have extended a suitable coverage distance, the locking members 1127A/1127B are placed into a locked state by rotation of the locking members 1127A/1127B so that the fastener 1129A/1129B are re-attached to a different region of the complementary fasteners 1135A/1135B positioned on the anterior side of each lateral panel 1130A/1130B. At that time, the lateral panel 1130A/1130B of the anterior bracing system 1110 are positioned under the lateral panels 210 of the posterior bracing system 110 as shown in FIG. 20G.

Referring to FIG. 20H, the extension rod 1140, which is coupled to the anterior panel 1120 extending in a superior direction therefrom, may be adjusted in order to a positioning of the support chest plate 1160. In the alternative, although not shown, where the orthopedic brace operates as a CTLSO, the adjustment of the extension rod 1140 may be to adjust the positioning of the CTO neck brace. As shown, the extension rod locking member 1128 is configured to rotate between open and closed positions to lock (or retain) the extension rod 1140 in a particular position, where the position of the extension rod 1140 refers to an amount that the extension rod 1140 extends in the superior direction. This is conducted to properly place the support chest plate 1160 on the wearer, As shown in FIG. 20I, after the posterior bracing system 110 and the anterior bracing system 1110 are positioned on the wearer to collectively operate as the orthopedic brace, the first set of support straps (e.g., first support strap 8500 and support strap 9550) may be deployed over a shoulder of the wearer 9500 or under the axilla of the wearer. Each of the support straps 8500/9550 includes a locking bracket 9560/9565, each snaps into a locking position when prescribed apertures 9562/9567 in a distal end of the locking bracket 9560/9565 engages corresponding snap lock 9570/9575 of the support chest plate 1160.

Additionally, as shown in FIG. 20J, after the posterior bracing system 110 and the anterior bracing system 1110 are positioned on the wearer to collectively operate as the orthopedic brace, the second set of support straps (e.g., second support strap 8600) may be deployed under an axilla of the wearer 9500 or over the shoulder. Each of the telescopic lateral panel for the posterior bracing system 110 (e.g., telescopic lateral panel 210) includes the buckle attachment aperture 425 that is sized to receive a buckle 9580 associated with the second support strap 8600. As shown, the buckle 9580 is inserted into the buckle attachment aperture 425, causing the buckle retention appendage 426 to engage and become inserted into an opening 9585 formed by a raised bar 9590 of the buckle attachment aperture 425.

Herein, the buckle attachment aperture 425 assists in the donning process. As an illustrative example, when the patient or clinician pulls the posterior lateral panels out, the buckle attachment aperture 425 pulls the support strap 8600 outwardly. As a result, the orthopedic brace 100 is easily accessible. The other end of the support strap may be fastened onto the posterior back panel or the extension panel.

Lastly, as shown in FIGS. 20I & 20K, the first and second sets of support straps may be tightened and each of the designated pulley cord $\mathbf{180}_1$ and/or $\mathbf{180}_2$ may be tightened by pulling the handle $\mathbf{185}_1$ and/or $\mathbf{185}_2$ toward the midline. This adjustment causes the lateral panels 520/620 extending from the posterior panel 120 to slide over the lateral panels 1130 extending from the anterior panel 1120. This increases the amount of overlap realized by the panels 520 & 1130A and 620 & 1130B symmetrically on both lateral sides, thereby tightening the orthopedic brace 100 to the wearer. The intact orthopedic brace 100 is shown in FIG. 20K.

In the foregoing description, the invention is described with reference to specific exemplary embodiments thereof. For example, the telescopic lateral panels and adjustable belt member combination, operating with a pulley subsystem, may be deployed within an LSO orthopedic brace with an architecture different than the orthopedic brace described above. Hence, it will be evident that certain components may be deployed within different types of orthopedic braces and various modifications and changes may be made thereto without departing from the broader spirit and scope of the invention.

What is claimed is:

1. An orthopedic brace comprising:

a posterior bracing system including a first plurality of telescopic lateral panels with a first telescopic lateral panel separate from and positioned anterior to a first belt member and a second telescopic lateral panel separate from and positioned anterior to a second belt member, wherein the first telescopic lateral panel is configured for coupling to the first belt member and the second telescopic lateral panel is configured for coupling to the second belt member;

an anterior bracing system including a second plurality of telescopic lateral panels, the second plurality of telescopic lateral panels includes a third telescopic lateral panel and a fourth telescopic lateral panel, wherein the first telescopic lateral panel and the first belt member are positioned into a curved form to enable the first belt member to attach to the third telescopic lateral panel of the anterior bracing system and the second telescopic lateral panel and the second belt member are positioned into a curved form to enable the second belt member to attach to the fourth telescopic lateral panel of the anterior bracing system.

2. The orthopedic brace of claim 1, wherein the posterior bracing system comprises:

a posterior panel;

a posterior cover coupled to the posterior panel, the posterior cover being configured to create a first chamber partially formed by an anterior facing surface of the posterior cover and a posterior facing surface of the posterior panel; and a pulley cover coupled to the posterior cover to create a second chamber partially formed by an anterior facing surface of the pulley cover and a posterior facing surface of the posterior cover, wherein the first chamber is configured to partially house the first plurality of telescopic lateral panels with each of the first telescopic lateral panel and the second telescopic lateral panel being arranged to extend laterally outward of the first chamber and the second chamber is configured to house a pulley subsystem including a plurality of pulley bases.

3. The orthopedic brace of claim 2, wherein the posterior facing surface of the posterior cover comprises a guide channel formed on the posterior facing surface of the posterior cover, the guide channel enabling lateral movement of (i) a first pulley base of the plurality of pulley bases between a first opening within the second chamber and a central area of the second chamber and (ii) a second pulley base of the plurality of pulley bases between a second opening within the second chamber and the central area of the second chamber.

4. The orthopedic brace of claim 3, wherein the first opening of the second chamber being positioned on an opposite side of the second chamber as the second opening.

5. The orthopedic brace of claim 3, wherein the first belt member is attached to the first pulley base and the second belt member is attached to the second pulley base.

6. The orthopedic brace of claim 3, wherein the first pulley base of the plurality of pulley bases includes a first flange extending toward a first edge of the guide channel, the first edge of the guide channel including at least a first stop that, upon the first flange coming into contact with the first stop, prevents further lateral movement of the first pulley base towards the first opening.

7. The orthopedic brace of claim 2, wherein each of the first plurality of telescopic panels includes a main panel region and a retention panel region, the main panel region of the first telescopic panel corresponding to a first portion of the first telescopic panel removable from the first chamber and the retention panel region correspond to a second portion of the first telescopic panel remaining within the first chamber.

8. The orthopedic brace of claim 7, wherein the retention panel region of the first telescopic panel includes a first tab portion and a second tab portion that contact posts of the posterior cover operating as stops to prevent complete removal of the first telescopic panel from the first chamber.

9. The orthopedic brace of claim 1, wherein the posterior bracing system comprises:

a posterior panel; and a posterior cover positioned over a portion of a posterior surface of the posterior panel and coupled to the posterior panel, the posterior cover being configured to create a first chamber partially formed between an anterior facing surface of the posterior cover and the posterior facing surface of the posterior panel, wherein the first chamber is configured to house the first plurality of telescopic panels each arranged to partially extend laterally outward of the first chamber and bend in a concave manner towards a front of the orthopedic brace to provide lateral support for a wearer of the orthopedic brace.

10. The orthopedic brace of claim 1, wherein the posterior bracing system further comprises an extension panel that includes a planar panel and a plurality of locking protrusions placed within the planar panel, the plurality of locking protrusions are configured for secure attachment to a plurality of locking slots positioned within a posterior panel so that a portion of the extension panel extends upwardly from a top edge of the posterior panel.

11. The orthopedic brace of claim 1, wherein the anterior bracing system comprises:

an anterior panel including a plurality of rotatable locking members each disposed on an opposing side of the anterior panel; and the second plurality of telescopic lateral panels configured to extend in a lateral direction or retract in a medial direction, wherein the second plurality of telescopic lateral panels are disposed on a posterior side of the anterior panel, wherein the plurality of rotatable locking members are configured to rotate between an open position and a closed position such that (i) when in the open position, the second plurality of telescopic lateral panels are able to extend or retract, and (ii) when in the closed position, the second plurality of telescopic lateral panels are locked in a current position.

12. The orthopedic brace of claim 11, wherein at least the third telescopic lateral panel of the second plurality of telescopic lateral panels includes an anterior surface with a first fastener disposed thereon, the first fastener is complementary to a second fastener disposed on a posterior side of a first rotatable locking member of the plurality of rotatable locking members.

13. The orthopedic brace of claim 11, wherein the anterior panel of the anterior bracing system further comprises (i) an opening receptacle adapted to receive an extension rod and (ii) an extension rod locking member adapted to rotate between an open position that allows for a release or insertion of the extension rod and a closed position to lock and retain the extension rod in a particular position.

14. The orthopedic brace of claim 13, wherein a first distal end of the extension rod includes a wishbone coupler, the wishbone coupler includes a body portion and a pair of extension arms extends in a superior direction and at slightly opposing angles relative to a midline of the wishbone coupler.

15. The orthopedic brace of claim 14, wherein the pair of extension arms of the wishbone coupler are coupled to either (i) a cervical thoracic orthosis (CTO) clip securely fastened to a cervical collar brace or (ii) a support chest plate.

16. The orthopedic brace of claim 10, wherein the first telescopic lateral panel includes a buckle attachment aperture to retain a buckle of a first support strap configured to be positioned under an axilla of a wearer, the first support strap assists in retention of the orthopedic brace on the wearer.

17. The orthopedic brace of claim 16 further comprising a second support strap inserted through and retained by a strap slot formed within the extension panel, wherein the second support strap is configured to be positioned over a shoulder of the wearer.

18. An orthopedic brace comprising:

a posterior bracing system including a posterior panel, a first plurality of telescopic lateral panels being a component separate from the posterior panel and laterally extendable from the posterior panel, a plurality of pulley bases, a plurality of belt members coupled to the plurality of pulley bases, and an extension panel coupled to the posterior panel and extending upward beyond an upper edge of the posterior panel;

an anterior bracing system including an anterior panel and a second plurality of telescopic lateral panels extendable from the anterior panel, wherein the anterior bracing system operates as a front portion of the orthopedic brace while the posterior bracing system operates as a rear portion of the orthopedic brace, wherein during a donning process, the first plurality of telescopic lateral panels are positioned anterior to and coupled to the plurality of belt members and both the first plurality of telescopic lateral panels and the plurality of belt members are positioned to overlay a portion of the second plurality of telescopic lateral panels when the second plurality of telescopic lateral panels are moved toward the posterior panel and the first plurality of telescopic lateral panels are moved toward the anterior panel.

19. A method of donning an orthopedic brace including a posterior bracing system and an anterior bracing system, comprising:

sizing belt members being part of the posterior bracing system;

placing a wearer with thoracic and lumbar back regions resting on an anterior-facing portion of a posterior panel of the posterior bracing system;

extending a first plurality of telescopic lateral telescopic panels associated with the posterior bracing system and the belt members attached to and posteriorly located from the first plurality of telescopic lateral telescopic panels away from the posterior panel;

positioning the anterior bracing system over an abdomen of the wearer;

disengaging locking members to permit adjustment of a second plurality of telescopic lateral telescopic panels associated with the anterior bracing system; and adjusting positioning of the first plurality of telescopic lateral telescopic panels towards an anterior panel so that the first plurality of telescopic lateral telescopic panels overlay the second plurality of telescopic lateral telescopic panels; and adjusting positioning of the belt members towards the anterior panel for coupling to one or more fasteners located on an anterior surface of the anterior panel and anterior surface of one of the second plurality of telescopic lateral telescopic panels.

* * * * *